United States Patent
Singh et al.

(10) Patent No.: US 10,238,516 B1
(45) Date of Patent: Mar. 26, 2019

(54) SIMPLIFIED IMPLANTABLE GASTRIC BALLOON SYSTEM WITH SELF DEFLATING TIMER

(71) Applicant: Barix Medical Corp., a Delaware Corporation, Charleston, WV (US)

(72) Inventors: Shailendra Singh, Charleston, WV (US); Irwan Shah Mohd Moideen, Singapore (SG)

(73) Assignee: BARIX MEDICAL CORP., Charleston, WV (US)

( * ) Notice: Subject to any disclaimer, the term of this patent is extended or adjusted under 35 U.S.C. 154(b) by 0 days.

(21) Appl. No.: 16/025,927

(22) Filed: Jul. 2, 2018

Related U.S. Application Data

(60) Provisional application No. 62/580,040, filed on Nov. 1, 2017, provisional application No. 62/614,356, filed on Jan. 6, 2018.

(51) Int. Cl.
*A61F 5/00* (2006.01)

(52) U.S. Cl.
CPC ............ *A61F 5/003* (2013.01); *A61F 5/0036* (2013.01)

(58) Field of Classification Search
CPC . A61F 5/003; A61F 5/0036; A61M 25/10185; A61M 25/10186; Y10T 137/7889; Y10T 137/87153; Y10T 137/3331; Y10T 137/7842; Y10T 137/87177; B65D 47/205

See application file for complete search history.

(56) References Cited

U.S. PATENT DOCUMENTS

| | | | | |
|---|---|---|---|---|
| 1,630,040 A | * | 5/1927 | Vogt | F16K 15/202 137/223 |
| 4,416,267 A | * | 11/1983 | Garren | A61F 5/0036 128/898 |
| 6,733,512 B2 | * | 5/2004 | McGhan | A61F 5/003 604/99.02 |
| 7,243,682 B2 | * | 7/2007 | Brandes | F16K 15/142 137/512.15 |
| 7,749,254 B2 | * | 7/2010 | Sobelman | A61F 5/003 606/256 |
| 8,292,911 B2 | | 10/2012 | Brister et al. | |
| 2004/0186502 A1 | * | 9/2004 | Sampson | A61F 5/003 606/191 |
| 2006/0058829 A1 | * | 3/2006 | Sampson | A61F 5/003 606/192 |

(Continued)

*Primary Examiner* — Kathleen S Holwerda
(74) *Attorney, Agent, or Firm* — Stephen E. Zweig

(57) ABSTRACT

An implantable inflatable gastric balloon device and system comprising a combination flow regulator and timing regulator, useful for inducing satiety and managing obesity. The balloon is administered into the patient's stomach in a deflated state, and then inflated by gas or liquid. The flow portion of the regulator usually acts as a one-way valve allowing gas or liquid to enter but not exit the balloon. The timing portion of the regulator has a degradable plug that gradually degrades over time, eventually allowing this gas or fluid to escape, thus allowing the balloon to escape. The dimensions of the device are configured so that in a deflated state, the balloon can pass by natural physiological processes through the pyloric sphincter and out of the patient through the intestines. Diagnostic methods, and methods for administering and managing the device, are also taught.

20 Claims, 54 Drawing Sheets

(56) References Cited

U.S. PATENT DOCUMENTS

| | | | |
|---|---|---|---|
| 2007/0078476 A1* | 4/2007 | Hull, Sr. | A61F 5/003 606/191 |
| 2007/0104755 A1* | 5/2007 | Sterling | A61F 2/04 424/423 |
| 2007/0178160 A1* | 8/2007 | Burnett | A61B 5/14539 424/484 |
| 2008/0051823 A1* | 2/2008 | Makower | A61B 17/1285 606/192 |
| 2013/0289604 A1* | 10/2013 | Brister | A61F 5/0036 606/192 |
| 2016/0029998 A1* | 2/2016 | Brister | A61B 5/6853 600/424 |
| 2017/0290693 A1 | 10/2017 | Nelson et al. | |

* cited by examiner

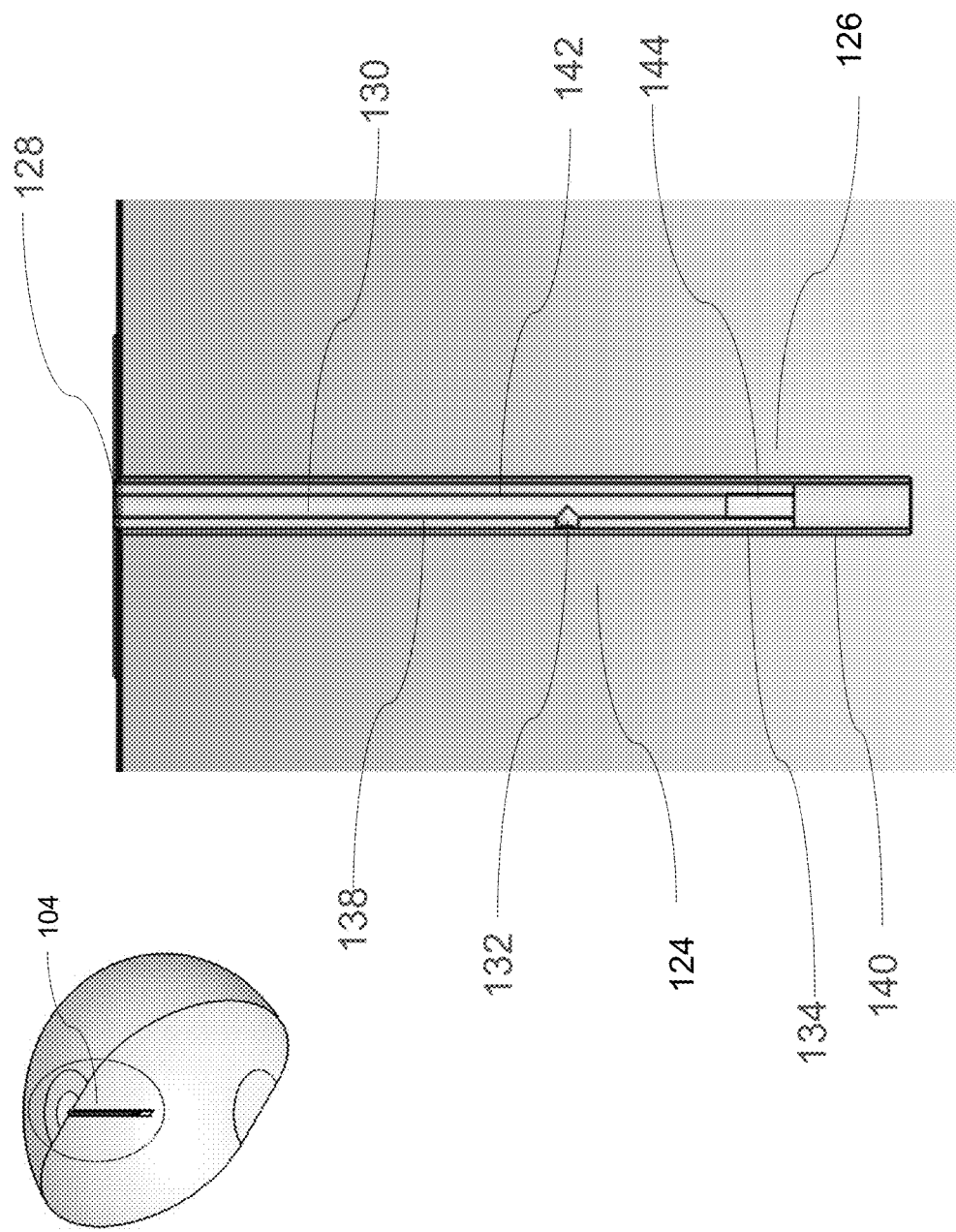

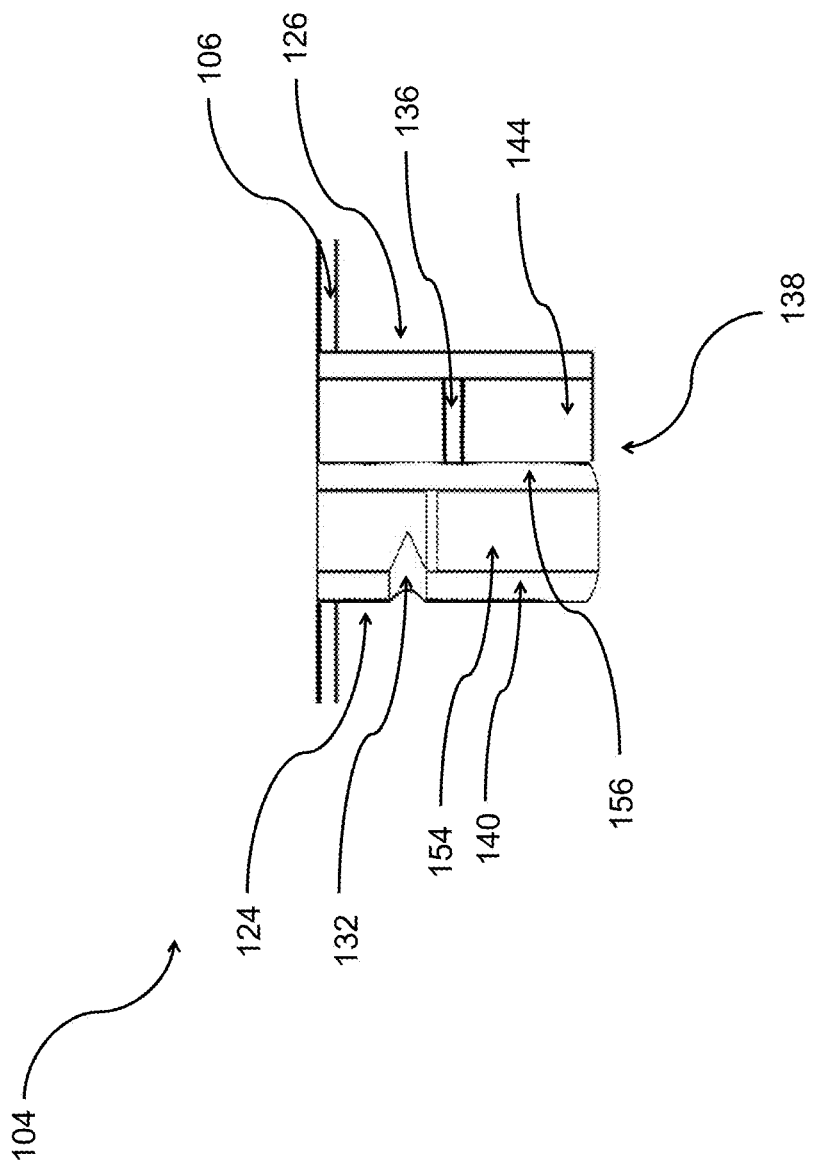

104

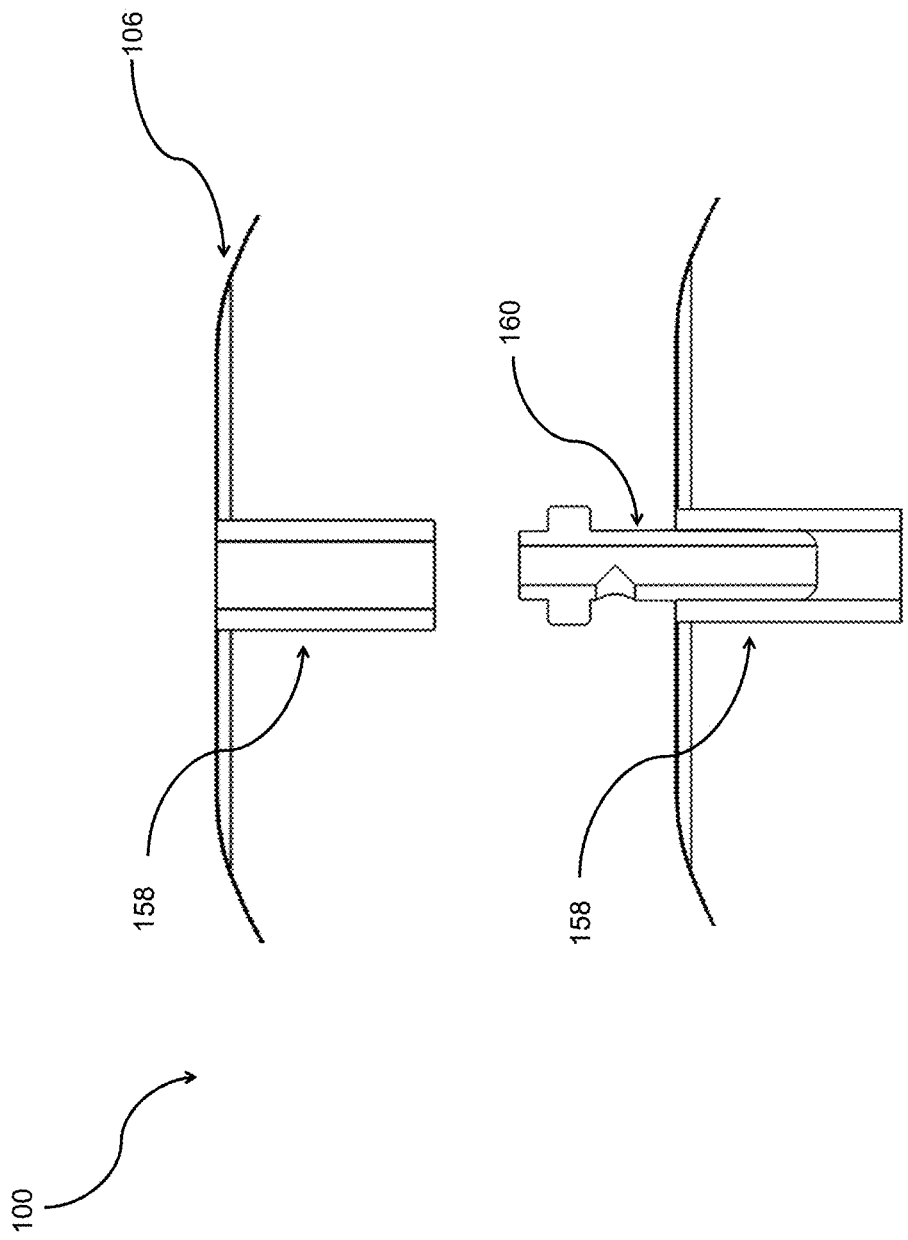

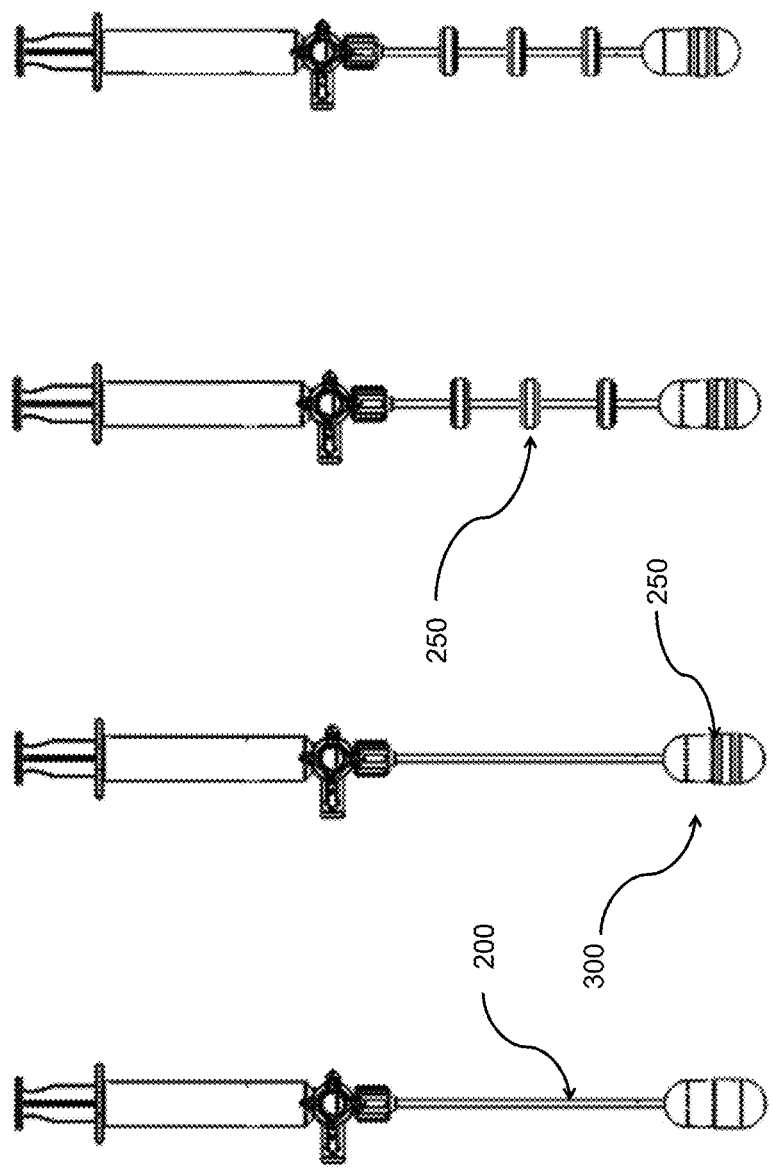

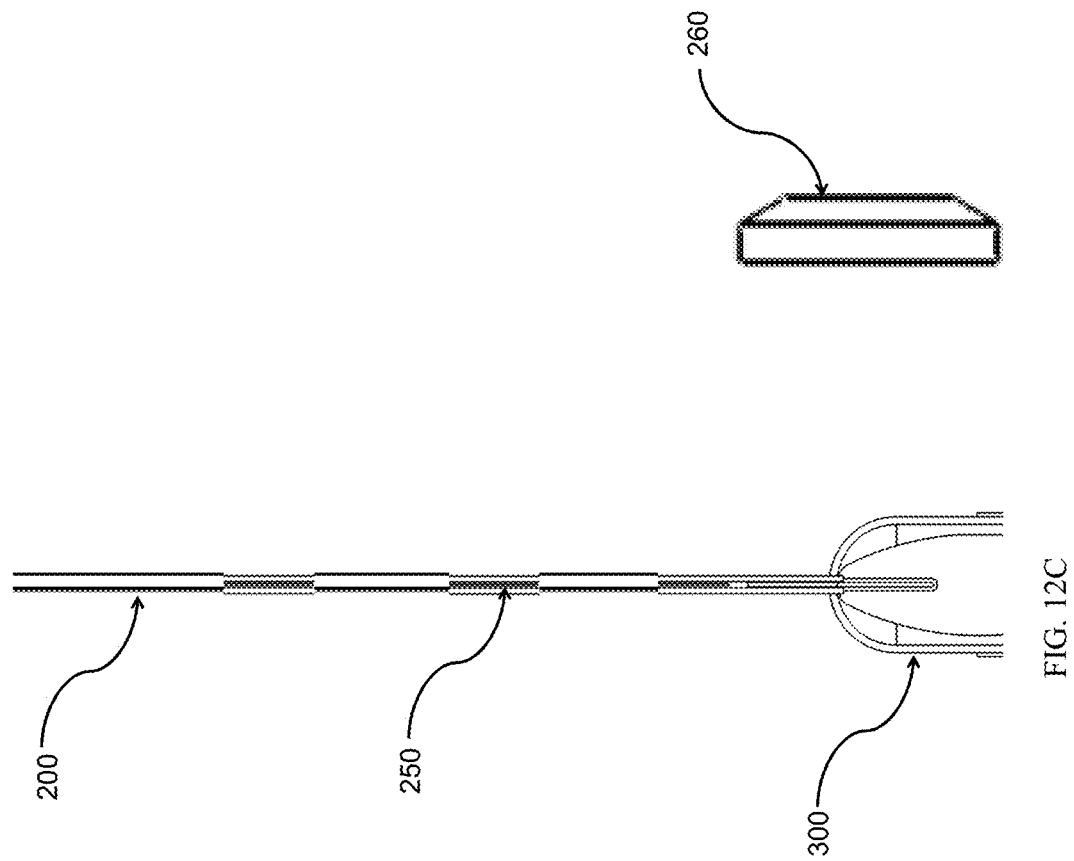

SIMPLIFIED IMPLANTABLE GASTRIC BALLOON SYSTEM WITH SELF DEFLATING TIMER

CROSS REFERENCE TO RELATED APPLICATIONS

This application claims the priority benefit of U.S. provisional patent application 62/580,040, filed Nov. 1, 2017, and U.S. provisional patent application 62/614,356, filed Jan. 6, 2018, the entire contents of both applications are incorporated herein by reference.

BACKGROUND OF THE INVENTION

Field of the Invention

The invention is in the field of implantable medical devices, specifically implantable inflatable gastric balloons for the treatment of obesity.

DESCRIPTION OF THE RELATED ART

Obesity is a significant health problem confronting the general public and healthcare industry today. According to WHO, the problem of worldwide obesity has more than doubled since 1980. In 2014, more than 1.9 billion adults, 18 years and older, were overweight. Of these, over 600 million were obese. On a percentage basis, 39% of adults aged 18 years and over were overweight in 2014, and 13% were obese. Obesity is a significant risk factor for many diseases such as heart disease, stroke, diabetes, high cholesterol, musculoskeletal disorders (osteoarthritis), as well as certain cancers such as endometrial cancer, breast cancer, ovarian cancer, prostate cancer, liver cancer, gallbladder cancer, kidney cancer, and colon cancer.

Historically, medical options to assist weight loss have included lifestyle modifications, drugs, and surgical methods. Lifestyle modification is generally ineffective to produce sustainable weight loss due to non-compliance. Weight loss medications have limited effectiveness due to patient non-compliance, and also carry significant safety risks and adverse side effects. Gastric bypass is a surgery which results in a substantial amount of weight loss, along with a permanent change in anatomy. Surgery is associated with significant potential complications and high overall costs. Most of the patients who might need weight loss surgery are not actually candidates for surgery because of the high risk high chances of complications. Only 1 to 2 percent of people who are eligible for weight loss surgery decide to have it. For the other 99 percent, the idea of permanently changing their bodies, and the risk of life-threatening complications, make surgery undesirable.

People generally prefer a non-surgical and minimally invasive treatment such as gastric or stomach balloons for obesity treatment. The FDA has approved stomach balloons for treatment of obesity. These gastric or stomach balloons provide a less invasive, safe and cheaper weight loss devices.

Prior art gastric balloons are inserted into the stomach with endoscopy, left in place for six months to about a year, and then removed by endoscopy.

This is not a simple task. Endoscopy equipment and facilities for placement of these devices is often not readily available and is also associated with high cost. Anesthesia is also required for endoscopic placement. Although a low risk, patients do not prefer invasive procedures. Currently, there is a shortage of trained gastroenterologists or surgeons (especially in rural areas and in developing countries) in comparison to the sizeable obese population.

Another problem is that most of the prior art gastric balloons are thick and bulky, which makes placement and removal challenging and uncomfortable to the patient. Although some newer devices, such as the Obalon® swallowable balloon, produced by Obalon Therapeutics, Inc., San Diego, Calif., are now smaller, often the patient needs to swallow multiple such balloons, and thus requiring multiple visits. This system is described in various US patents, including Brister, U.S. Pat. No. 8,292,911; Sampson, US patent publication 2006/0058829; Nelson, US patent publication 2017/0290693, and others.

Such newer devices still tend to require specialized X-rays/fluoroscopy or ultrasound to confirm placement in the stomach. This therefore requires special facility, trained personnel, additional costs and (for imaging purposes) exposure to harmful radiation.

These devices should ideally remain in the stomach for the appropriate long duration to result in effective and longer lasting weight loss. One of the other limitations of newer balloons is the short duration (<4 months) of action for weight loss. Newer balloons have fixed duration of action, and the duration of the treatment cannot be changed according to patient's desire or needs. Also, most of these devices are not covered by insurance; are very expensive (costs often vary from $4,000 to $9,000 US dollars) and not readily available in most developing countries such as India. These devices have only therapeutic applications for weight loss and generally have no other diagnostic or other therapeutic applications.

BRIEF SUMMARY OF THE INVENTION

The invention is based, in part, on the insight that there is a need for a system and method that utilizes an improved gastric balloon system for treating obesity. Ideally, an improved gastric balloon system that can be swallowed by the patient quickly, and does not require the use of endoscopy for insertion and removal.

Ideally, such an improved gastric balloon system would include biodegradable or bioabsorbable components so that the balloon would automatically pass into the toilet or otherwise safely get absorbed after at least six months use in the patient. Thus a biodegradable or bioabsorbable system would reduce or eliminate the need for endoscopy specialist, and instead might be placed by any physician or trained professional.

The invention is also based, in part, on the insight that there is a need for a gastric balloon system where the duration of such treatment can be changed and controlled according to patient need or desire. Furthermore, there is a need for a gastric balloon system that can utilize safer, cheaper and simpler technology (relative to endoscopy) to help monitor balloon placement, such as electromagnetic or electronic technology or cameras. This would avoid costs and harmful radiation.

There is also a need for a system and method to provide a simple cost-effective and efficient gastric device to serve more patients in rural areas and developing countries. Additionally, there is need to add diagnostic capabilities, minimize complications and use these methods for other therapeutic indications.

Thus in some embodiments, the invention may comprise an inflatable gastric balloon gastrointestinal device. This gastric balloon may comprise a thin flexible polymeric skin enclosing an interior volume. This balloon will be configured to be capable of transitioning between a contracted state and an expanded state. To do this, the balloon will further comprise an expansion valve (also called a flow regulator) embedded in the balloon's skin. This expansion valve/flow regulator will be configured to spanning from the balloon's interior to the balloon's exterior. This expansion valve is an adjustable one-way valve configured to:

a) In a first open mode, permit outside pressurized gas or fluid to enter the balloon (often by way of a catheter, to be discussed) and cause the balloon to transition from a contracted state an expanded state.

b) In a second closed mode, prevent any internal pressurized gas or fluid from inside the balloon from exiting the balloon by way of this expansion valve.

In the expanded state, this balloon will typically have interior volume expanded state dimensions greater than 50 milliliters. However, in the contracted state, this balloon will have much smaller contracted state dimensions of less than 2 centimeters in diameter and less than 5 centimeters in length. In particular, the balloon is configured so that in the contracted state, the balloon can naturally (i.e. by the normal action of the digestive system) pass out of the human patient's stomach and completely through the human patient's gastrointestinal tract.

In a preferred embodiment, the invention's balloon device will further comprise a timing valve (also called a timing regulator). This timing valve will also be embedded in the balloon's skin, and will also span from the balloon's interior to the balloon's exterior. This timing valve will typically comprise a gas and fluid impermeable degradable element that is embedded in a hollow sheath. The timing valve configured so that:

c) While the timing valve's degradable element is intact, prevent any internal pressurized gas or fluid from inside the balloon from exiting the balloon by way of the timing valve.

d) However, after the timing valve's degradable element has degraded, the timing valve will allow any internal pressurized gas or fluid exit the balloon by way of the timing valve.

Although the timing valve (timing regulator) may be separate from the expansion valve (flow regulator), in a preferred embodiment, the expansion valve (flow regulator) and the timing valve (timing regulator) will comprise a single regulator. This single (e.g. combined) regulator will comprise a combination expansion valve (flow regulator) and timing valve (time regulator) device, often based on a common hollow tube structure. This regulator will be embedded in the balloon's skin and span from the balloon's interior to the balloon's exterior.

Thus to summarize, in some embodiments, the invention may be an implantable inflatable gastric balloon device and system comprising a combination flow regulator and timing regulator. Although this device may be useful for inducing satiety and managing obesity, the device may also be used for other applications, such as various medical diagnostic applications.

In use, the balloon device is administered into the patient's stomach in a deflated state, and then inflated by gas or liquid. The flow portion of the regulator usually acts as a one-way valve allowing gas or liquid to enter but not exit the balloon. The timing portion of the regulator has a degradable plug that gradually degrades over time, eventually allowing this gas or fluid to escape, thus allowing the balloon to escape. The dimensions of the device are configured so that in a deflated state, the balloon can pass by natural physiological processes through the pyloric sphincter and out of the patient through the intestines.

BRIEF DESCRIPTION OF THE DRAWINGS

FIG. 3B illustrates an example of a hollow cylindrical regulator 104, in accordance with at least one embodiment.

FIG. 3K illustrates an example of the regulator 104 in which the expansion valve 124 and timing valve 126 are separate valves but attached together to form one unit embedded in a same location in skin.

FIG. 4B illustrates an example wherein the degradable band 158 attached to the skin 106 and the valve 160 is embedded in the band 158.

FIG. 12A illustrates an exemplary view of capsule 300 and the intermedium catheter 200 with sensors 250.

FIG. 12C illustrates multiple sensors 250 on the distal and or medial intermedium catheter 200 and a coupled guiding system 260 to enable the capsule 300 and intermedium catheter 200 advancements.

DETAILED DESCRIPTION OF THE INVENTION

Figure 1A:
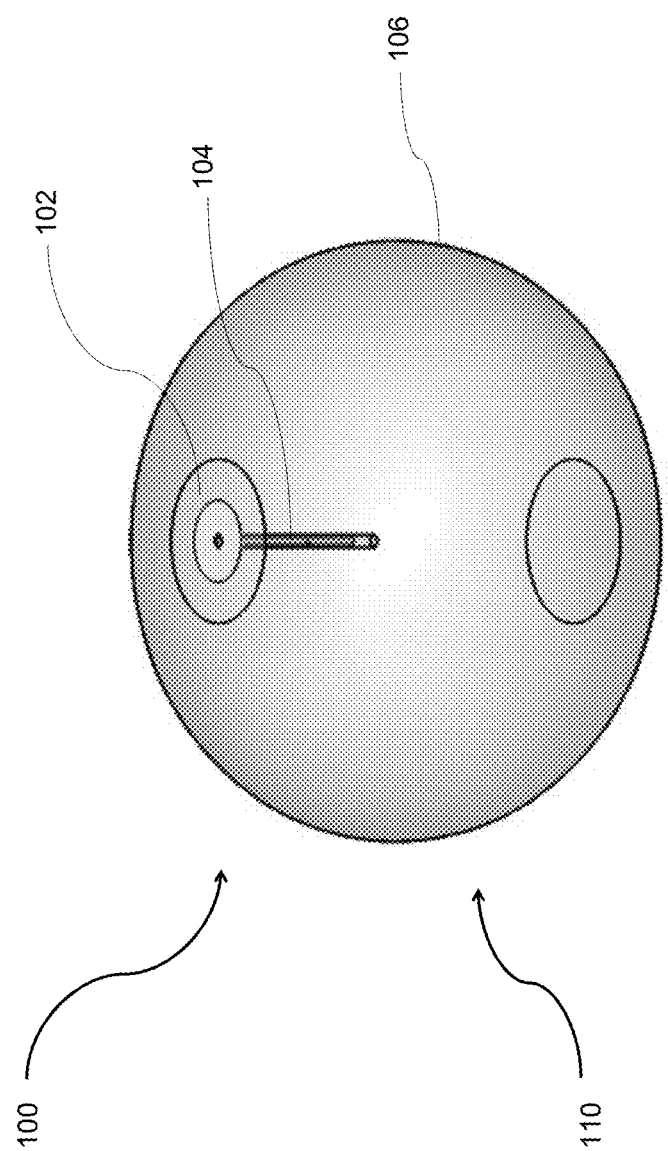
FIG. 1A illustrates an expanded state 110 of the balloon 100 comprising of skin 106 with an embedded regulator 104 at the neck 102, in accordance with at least one embodiment.

According to embodiments illustrated herein, there may be provided a device, system, and method for ingestion, tracking, expansion, contraction, and passage of a gastrointestinal device. In particular, the devices, system, and methods can be used in the gastric lumen for treatment of obesity and other diagnostic and therapeutic applications. However, the methods, devices, and tools can be used in any part of the gastrointestinal tract.

In some embodiments, the invention's gastrointestinal device may comprise an inflatable polymeric balloon, a dual flow and timing regulator embedded in the balloon, a capsule containing the folded balloon, an intermedium catheter (200) with proximal and distal ends, an expansion pin, various sensors, and tracking systems (electromagnetic tracking system, etc.) within the intermedium catheter and or the regulator.

In some embodiments, the balloon (inflatable gastric balloon) can comprise a thin flexible polymeric skin enclosing an interior volume. This balloon can be configured to be capable of easily transitioning between a contracted state and an expanded state. In the first contracted state, the balloon is contracted and can be folded into a capsule for ingestion, in the second expanded state, the balloon is expanded and resides in a patient's gastrointestinal system. In a later third state, the balloon then contracts again for passage through the patient's gastrointestinal system.

In the expanded state, the balloon will often have an interior volume (expanded state dimensions) equal to or greater than 50 milliliters. In the third state, the balloon typically has contracted state dimensions of less than 2 centimeters diameter. and less than 5 centimeters in length. The balloon is configured so that when it is in its contracted state, the balloon can pass by natural action of the digestive system out from a stomach of a human patient, and then completely through the patient's gastrointestinal tract and out of the patient.

In an another embodiment, here termed a "grape" design, the gastric balloon can comprise a plurality of attached balloons. This "grape design" plurality of attached balloons will typically have expanded state dimensions so that a sum of the interior volume of this plurality of attached balloons is also equal to or greater than 50 milliliters. The dimensions of this plurality of attached balloons are also typically less than 2 centimeters in diameter and less than 5 centimeters in length. Thus, in the alternative "grape" design, this plurality of attached balloons is also configured so that when the plurality of balloons are in a contracted state, the "grape" configured plurality of attached balloons can also pass by natural digestive processes from out of a stomach of a human patient, and completely through the patient's gastrointestinal tract as well.

An important aspect of the invention is its combination flow regulator and timing device, here often referred to as the "regulator". This regulator is embedded in the gastric balloon's flexible polymeric skin. This regulator spans the thickness of the skin, and thus extends between the balloon's interior and the balloon's exterior. This regulator can be a combination of a gas or fluid regulating expansion valve (also called the "flow regulator unit") and a timing valve (also called the "timing regulator unit"). At earlier times, before the timer expires, the regulator can act as an adjustable one-way valve. The expansion valve portion of the regulator can be configured to, in a first open mode, permit any of outside pressurized gas or fluid to enter the balloon, thus causing the balloon to transition from a contracted state to an expanded state. A second closed mode of the regulator can be configured to then prevent any this internal pressurized gas or fluid from then exiting the balloon by way of this expansion valve. So it acts like a one-way valve, at least before the valve's built in timer expires.

The One-Way Valve (Flow Control) Portion of the Regulator Valve:

Typically, in the first open mode of operation, the expansion valve is configured so that the only gas and/or fluids that the valve allows to enter the balloon are those gas and/or fluids that are injected specifically in the outer portion of the regulator, at a pressure higher than any intragastric pressure inside the patient's stomach. The expansion valve can also be configured so that it allows only a desired volume of pressurized gas and fluids to enter the balloon. Note that at all times and all modes of operation, at least before the timer expires, the expansion valve is typically configured to not allow (e.g. prevent) entry of the patient's gastric contents into the interior of the balloon.

In some embodiments the regulator can be a modified hollow tube, which may be a cylindrical hollow tube, which spans across the balloon's skin from an interior to an exterior of the balloon. This hollow tube (sometimes called, in the alternative, a "cylindrical tube") is closed towards the interior of the balloon and open towards the exterior of the balloon. The exterior part of the regulator forms the opening of the regulator. Here the portion of the hollow tube that is in the interior of the balloon is called the "interior balloon side end", and the portion of the hollow tube located on the exterior of the balloon is called the "exterior balloon side end".

The expansion valve (flow control valve) portion of the regulator comprises one or more inner openings in this hollow tube. These openings are positioned around the circumference (see FIG. 3A, 132) of the hollow tube. An elastic polymeric sheath (140) completely covers the circumference of the hollow tube, at least over the region of the hollow tube containing the various inner openings (132). The space between the outer surface of the cylindrical tube and the inner surface of the sheath (inner sheath surface) is dynamic.

This sheath is chosen to be somewhat elastic, and with dimensions so that in the absence of any pressure, the elastic properties of the sheath cause it to press with enough force on the inner openings (132) of the hollow tube so as to seal the opening. However if there is enough pressure force coming from the inner opening (132) to press back against the sheath, the sheath, being somewhat elastic, will be displaced away from these openings (132), creating a small space or "gap" though which gas or liquid from the opening might then slip through the small space or gap and enter the inside of the balloon.

This small space (a gap between the outer circumference of the hollow tube, and the inner sheath surface) thus opens and closes based on the differential pressure between the pressure applied on the inner sheath surface by the injection of gas or fluid, and the pressure exerted on the outer surface of the sheath (outer sheath surface) by the pressure of the gas and fluid in the interior of the balloon pressing back.

In a first "open mode", sometimes called the first mode of the expansion valve, this small space or gap is open and permits pressurized gas and fluid, when injected at the inner opening through the "gap" opening of the regulator, to enter the balloon. After the complete expansion of the balloon or when the injection of pressurized gases and fluid are stopped, the expansion valve switches to the second "closed" mode, sometimes called the second mode of the expansion valve. In the second closed mode, this space is closed by the elastic polymeric sheath, which closely binds to the inner openings, and prevents the internal pressurized gas and fluid from using the inner opening to exit the balloon (through the regulator openings). Thus the hollow tube, the openings distributed along the circumference of the tube, and the elastic polymeric sheath, work together to form a one-way valve system that allows passage of fluid or gases injected into the opening of the expansion valve to enter the balloon, but which prevents leakage of the balloon's contents out of the balloon.

The Timing Portion of the Regulator Valve

The regulator (again based upon a hollow tube structure) further comprises a timing valve portion. This timing valve portion is based on a gas and fluid impermeable degradable element (degradable retainer plug), shown in FIG. 3A 144, and elsewhere. While this degradable element (degradable retainer plug) of the timing valve is intact, the plug prevents the balloon's internal pressurized gas or fluid from exiting the balloon by way of the regulator. This plug is based on a degradable material that will generally degrade according to a predetermined schedule, usually over a period of several months to a year.

While the balloon is inflated, and the degradable plug is intact, the degradable plug (144) maintains the balloon in the inflated expanded state. The degradable plug (144) can, for example, act to seal a timing opening (often oriented along the main axis of a cylindrical hollow tube structure). Once the degradable plug degrades, the regulator is configured so that the internal pressurized gas or fluid inside the inflated balloon can then exit the balloon via the tining opening, though the regulator plug's hollow tube structure, and outside into the patient's stomach. As a result, the balloon will start to deflate. Assuming that the balloon's polymeric skin itself has some elastic properties, like a real balloon, the elastic force of the balloon's skin can cause the balloon to deflate in size to an appreciable extent. When this happens, the balloon will transition back to a contracted state again.

The time for which balloon remains in the extended state (with extended state dimensions) and after which the balloon contracts (to contracted state dimensions) can be a function of the material properties of the degradation element (degradable retainer plug). This can include the actual material used in the plug, the physical dimensions, nature and processing of the degradable material, and also the properties of the environment (e.g. the gastric environment) in which the degradable retainer plug is exposed.

Figure 3A:
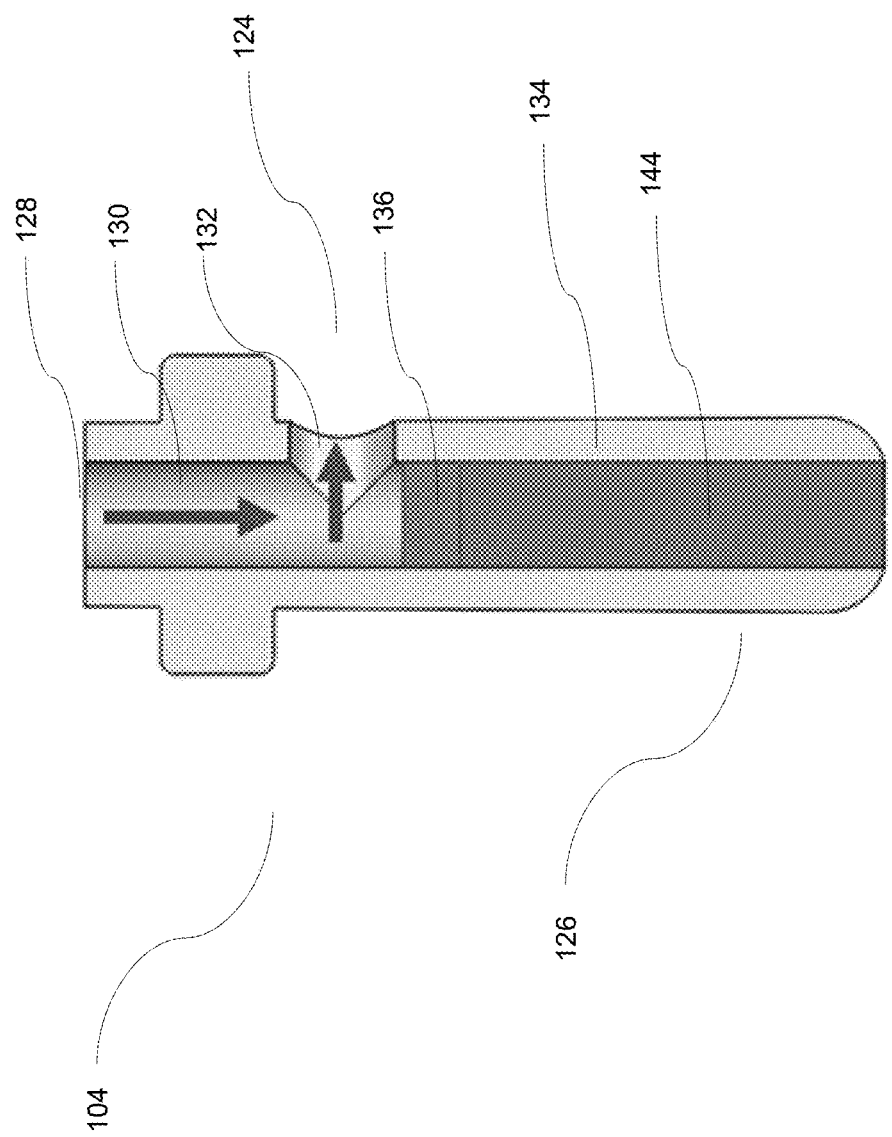
FIG. 3A illustrates a view of the regulator 104 comprising the expansion valve and timing valve, in accordance with at least one embodiment.

Thus in the example of the cylindrical regulator described above, the interior end of the hollow cylindrical tube can be filled with a substantially cylindrical degradable retainer plug previously shown in FIG. 3A 144, and elsewhere.

Put alternatively, the timing portion of the regulator valve is typically configured such that while the degradable retainer plug 144 is intact, the plug prevents any of internal pressurized gas and fluid from using the hollow cylindrical regulator to exit the balloon. After the degradable element (plug 144) has degraded, however, the timing portion of the regulator allows the balloon's internal pressurized gas and/or fluid to use the regulator's hollow cylindrical tube to exit the balloon.

The degradable retainer plug 144 often has a cylindrical structure, with typical cylindrical height and diameter dimensions. The time that this degradable retainer plug 144 remains intact can be at least partially determined by dimensions of the degradable retainer plug 144. In some embodiments, the degradable plug acts somewhat like a slowly degrading fuse, gradually dissolving upon contact with gastric fluids. Here the length of the retainer plug can help determine the timing, with longer plugs generally lasting longer than shorter plugs.

Put alternatively, in general, the timing or lifetime of the degradable retainer plug can be directly proportional to the time required for degradation of the retainer plug material, for any given set of degradable retainer plug 144 material and gastric environment. In principle, the lifetime of the expanded state of the balloon can be controlled by simply changing the length of the retaining plug. Thus, depending on materials chosen, length of the pug, and the patient's gastric environment, retaining plug lifetimes between hours and years may be chosen.

In some embodiments, the cylindrical degradable retainer plug 144 of the timing valve may be additionally covered with other materials. For example, one end of the retaining plug may be covered on the plug side facing towards the exterior of the balloon with a non-permeable nondegradable thin polymeric sheath. This end of the retaining plug may also be covered with an alternative thin one-way valve system, such as diaphragm valve, or slit membrane valve.

This retainer plug covering can be used to keep the degradable plug material from having direct exposure with the patient's gastrointestinal contents and fluids. In this embodiment, the lifetime of the plug will tend to not be affected by changes in the patient's digestive status, and instead the degradable plug can degrade in a more controlled environment. Here, only the environment within the interior of the balloon may affect the degradation rate of the plug. This can have the advantage of allowing the plug's degradation rate and timing to be more easily controlled and predicted. As before, the plug's covering can be configured such that while the degradable retainer plug 144 is intact, the patient's gastrointestinal contents do not contact the degradable retainer plug 144. However after the degradable retainer plug has degraded, the system will allow the balloon's internal pressurized gas and fluid to exit the balloon by way of the regulator'.

Alternative variations of this type of combination expansion (flow control) valve and timing valve design are also possible. In one alternative embodiment, the expansion valve and the timing valve may be separate from each other (i.e. may be based on different hollow tubes structures). That is, the flow control regulator may be different from the timing regulator, and may be embedded in different locations in the balloon's skin.

However in a preferred embodiment, the expansion (flow control) valve and the timing valve are different portions of a same regulator (i.e. occupy different parts of the same hollow tube structure), thus producing a dual-function regulator. This dual function regulator thus embeds both the flow control valve and the timing valve in roughly the same location in the balloon's skin.

The regulator can have several different design features depending on the needs. For example, the regulator can have a duckbill design, umbrella design, combination duck umbrella valve, duck bill valve, diaphragm design, slit valve design or another type of design.

As another alternative, if the retainer plug 144 is instead made of a non-degradable non-permeable material, the timer function of the regulator is removed, because the non-degradable material will never remain. Instead the regulator will act permanently prevent the balloon's internal pressurized gas or fluid from exiting. To keep the balloon from lasting forever, the balloon skin itself can be configured to degrade with time.

Embodiments where the Balloon's Skin Degrades with Time:

In some embodiments, the interior of the balloon can further comprise a biocompatible chemical or enzymatic material configured to degrade the degradable plug, or other degradable balloon component. The time frame of this degradation can be over a time range between hours to years when the balloon is stored inside the patient's stomach at the standard human body temperature of approximately 37 degrees centigrade.

In some embodiments, either some or all of the balloon's skin can further comprise a degradable material. As before, this degradable skin material can be configured to dissolve, causing the balloon to burst, over a time range between hours and year (when the balloon is in contact with a patient's gastrointestinal digestive fluids). In another embodiment, the entire regulator or other components of the regulator may also be configured to be degradable. Again, the balloon/regulator system may be configured so that degradation of these parts will cause the balloon to burst.

Attaching and Detaching the Balloon from Intermedium Catheters:

In some embodiments, the balloon may be temporarily attached to an intermedium catheter (200) by a detachable link. The intermedium catheter is a hollow tubular thin structure which facilitates placement and then the expansion of the balloon. The catheter has a proximal end, a medial portion and a distal end. The catheter has a detachable link that connects the distal end of the intermedium catheter with a proximal end of the expansion valve (flow regulator) portion of the regulator.

The intermedium catheter can be configured so that when it is attached to the expansion valve portion of the regulator, the catheter can be used to deliver outside pressurized gas or fluid to inflate the balloon. The proximal end of the catheter, which remains outside of the patient's mouth, can optionally be configured with a three-way stopcock.

The medial portion of the intermedium catheter will typically have a length that is longer than that of the patient's upper gastrointestinal tract (mouth to the distal end of the stomach), so that the proximal end of the catheter remains outside of the patient's mouth, the medial portion extends down the patient's upper gastrointestinal tract from at least the mouth to the stomach, and the distal portion of the distal end of the intermedium catheter, along with the attached balloon, can extend into the patient's stomach.

The intermedium catheter is further configured to apply mechanical force to the expansion valve portion of the regulator to detach the intermedium catheter from the balloon. In another aspect, the intermedium catheter can further comprise a freely movable outer catheter sheath, and use this catheter sheath to apply a forward force towards the balloon. At the same time, a reverse force can be applied to the intermedium catheter by pulling it towards the catheter's proximal end. After the balloon has been inflated, this catheter sheath can then be used to break the balloon off of the distal end of the catheter, so that the inflated balloon remains in the patient's stomach, and the rest of the catheter can then be withdrawn from the patient.

To do this, typically there will be a suitably configured breakable junction created between the distal portion of the catheter, and the top of the balloon. The moveable catheter sheath can then apply enough force to break this breakable junction between the distal portion of the catheter and the top of the balloon.

Alternatively, the intermedium catheter can be attached to the regulator or balloon with a suture. When separation between the balloon and the catheter is desired, this suture can be untied or detached from outside by pulling the intermedium catheter or sheath.

Figure 7A:
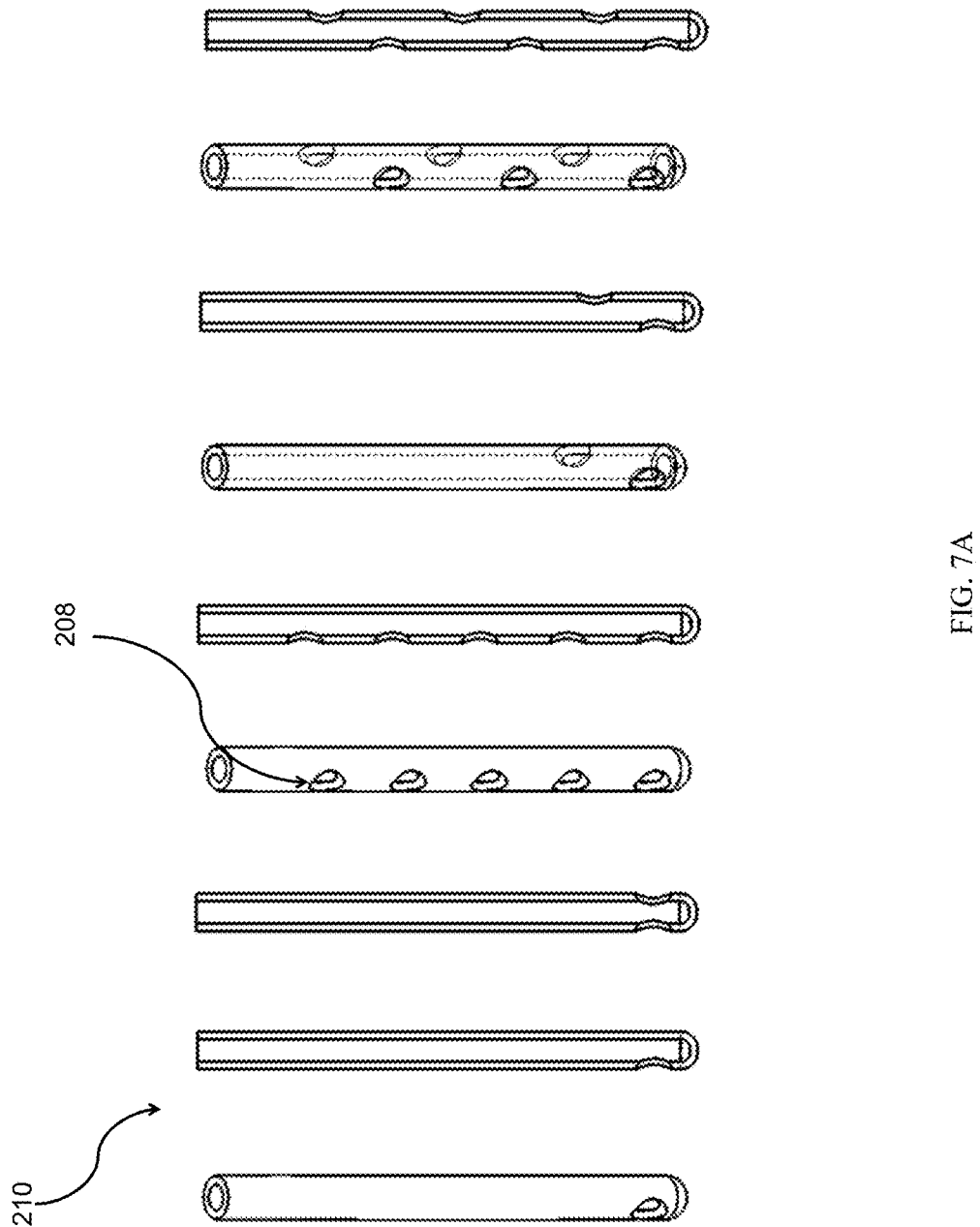
FIG. 7A illustrates a schematic view of the expansion pin 210 with or without side holes 208, in accordance with at least one embodiment.
Figure 7B:
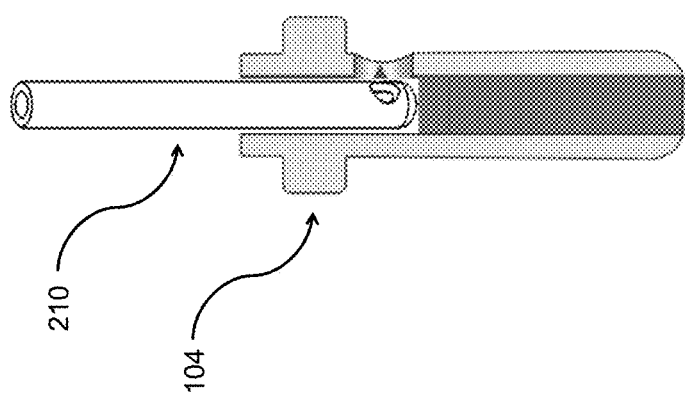
FIG. 7B illustrates the regulator 104 comprising of opening 128 in the expansion valve to accommodate a hollow expansion pin 210.
Figure 7B:
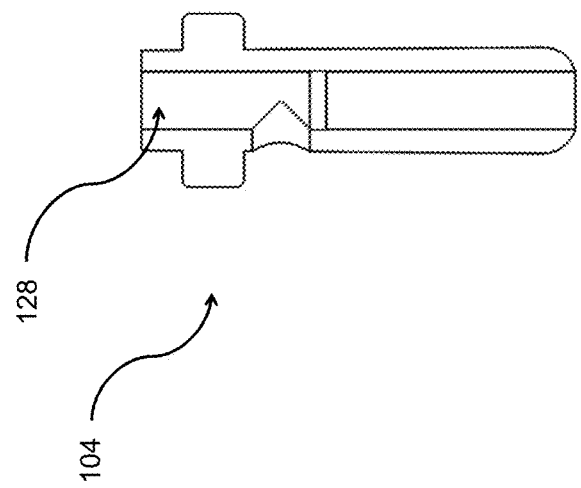
Figure 7C:
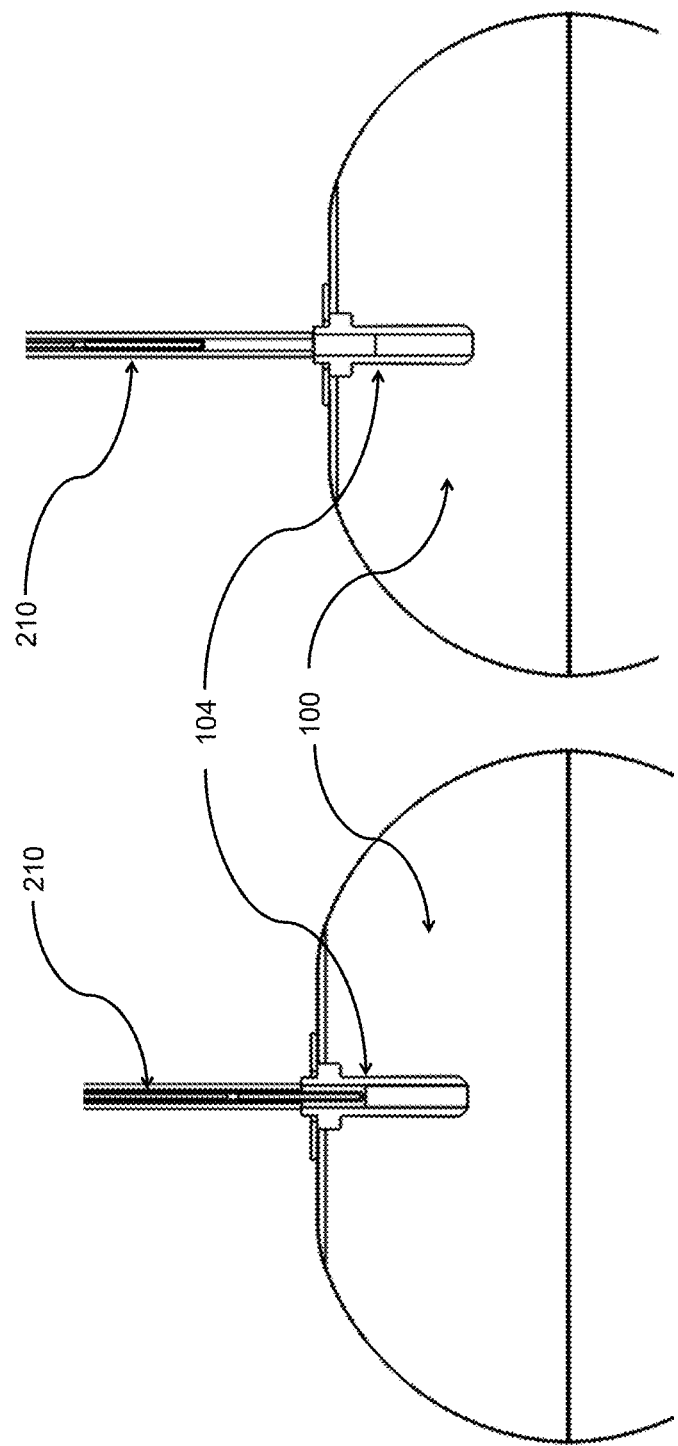
FIG. 7C illustrates the expansion pin 210 detachably attached to the regulator 104, in accordance with at least one embodiment.

In some embodiments, as shown in FIG. 7A-7C, the expansion valve portion of the regulator can further compare an outside opening (128) configured to accommodate a hollow expansion pin (210) with at least one side hole (208). This expansion pin can be configured to fit inside the outside opening in the expansion valve. The expansion pin can be used to place the expansion valve portion of the regulator in a first open mode, thus permitting passage of any fluid or gas into the balloon from the distal end of the intermedium catheter.

Here, the distal end of the intermedium catheter is attached to the hollow expansion pin, which in turn is connected to the expansion valve portion of the regulator, and places the expansion valve portion of the regulator into the first open mode. Thus when the intermedium catheter is attached to the expansion valve portion of the regulator, pressurized gas and fluid can be applied to the proximal end of the catheter, pass through the hollow expansion pin, and be delivered to the balloon. The intermedium catheter, expansion pin and expansion valve portion can be further configured so that when the expansion pin is at least partially withdrawn from the outside opening of the regulator, the expansion valve portion of the regulator now operates in the second closed mode, now preventing passage fluid or gas out of the balloon.

In some embodiments, at least a portion of the proximal end of the expansion valve portion of the regulator is exterior to balloon, and can be is detachably connected to distal end of the intermedium catheter. The timing valve portion of the regulator is attached to expansion valve portion (often they share the same hollow tube), and at least a portion of the distal end of the timing valve portion of the regulator is located on an interior of the balloon.

In some embodiments, the expansion pin itself serves as the detachable link. Here, for example, the expansion pin can be permanently attached to the distal end of the intermedium catheter. This expansion pin is also temporarily attached to the expansion valve portion of the regulator (usually the proximal end of the regulator that sticks somewhat outside of the balloon). When the expansion pin is inserted into the expansion valve portion of the regulator, this also puts the expansion valve portion of the regulator into the first open mode.

In this first open mode, the regulator and catheter are configured so that outside pressurized gas and fluid can be delivered, through the hollow expansion pin, to the balloon. The expansion pin is typically configured to be detachable from the outside of the expansion valve portion of the regulator, and the expansion pin and expansion valve portion of the regulator are configured so that removal of the expansion pin switches the expansion valve portion of the regulator from a first open mode to a second closed mode. This second closed mode is designed prevent pressurized gas and fluid inside the balloon from using the expansion valve to then exiting the balloon. As previously discussed, the intermedium catheter, here with the permanently attached expansion pin, can be further configured to apply mechanical force to the expansion valve portion (for example by using the previously described catheter sheath) to detach the expansion pin and intermedium catheter from the balloon (usually after the balloon has been placed in the patient's stomach and inflated).

Figure 9A:
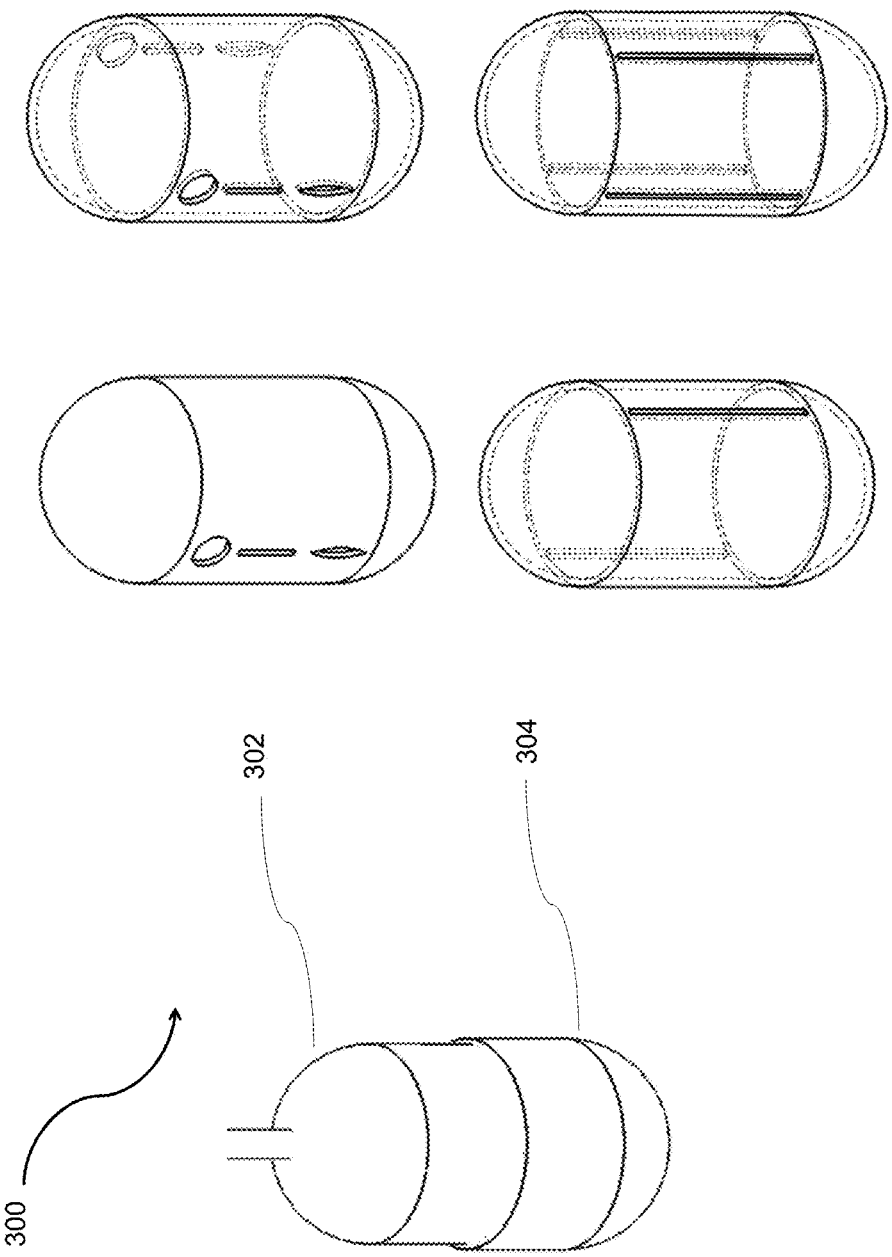
FIG. 9A illustrates a perspective view of the capsule 300, in accordance with at least one embodiment. The capsule 300 includes a top unit 302, and bottom unit 304.
Figure 9B:
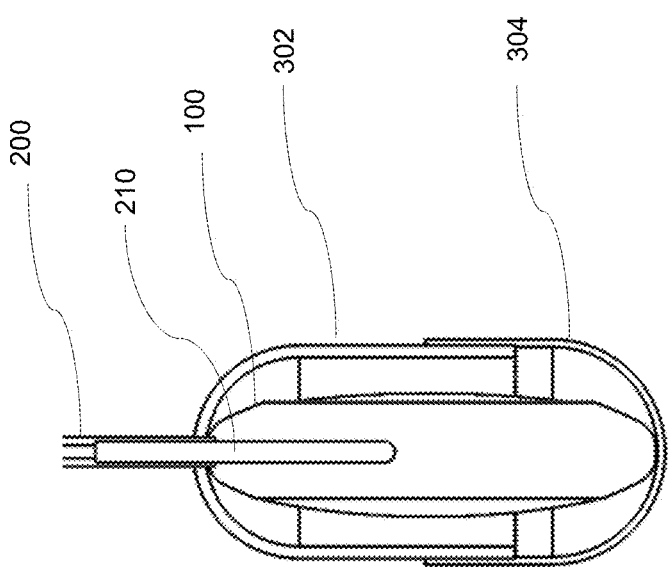
FIG. 9B illustrates a perspective view of the capsule sub-system, in accordance with at least one embodiment.
Figure 9C:
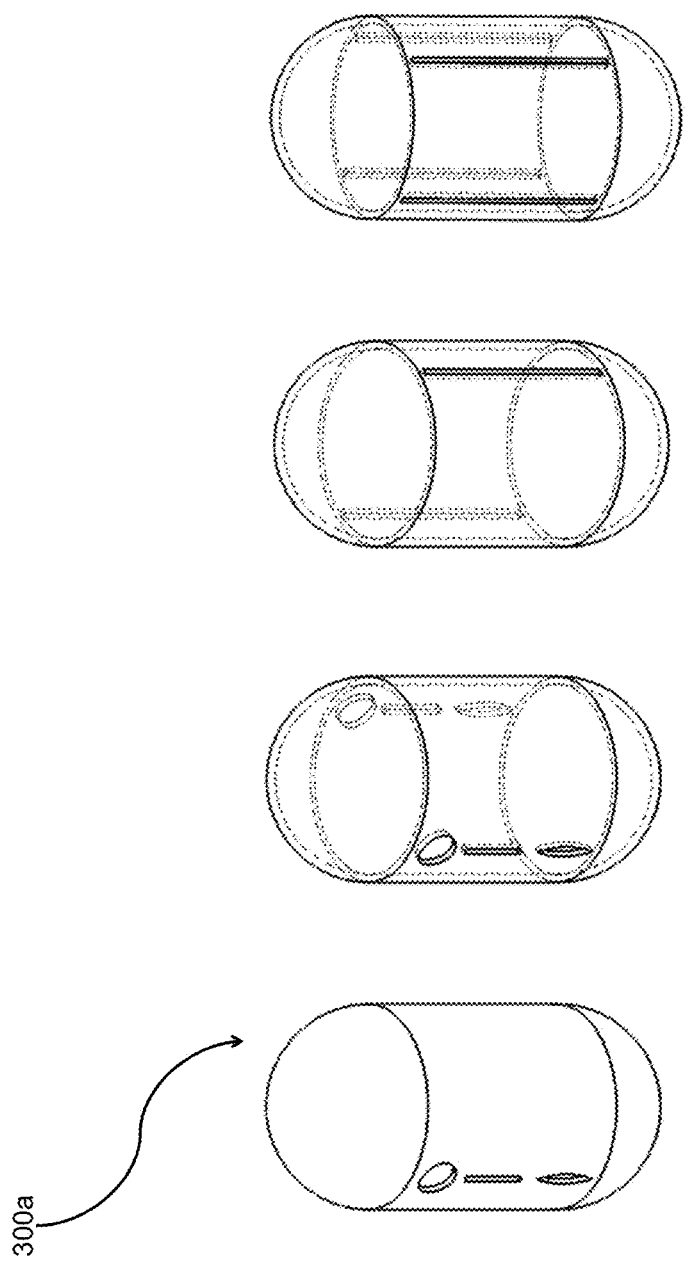
FIG. 9C illustrates another perspective view of the capsule sub-system, in accordance with at least one embodiment.

Balloon Packaging Prior to Inflation:

In order to facilitate delivery of the balloon to the stomach, the gastric balloon, in a deflated and compacted state, is often further disposed within a smooth capsule (300). This capsule can comprise a top capsule unit (302) and a bottom capsule unit (304). This is shown in FIG. 9A and FIGS. 9B and 9C.

The top capsule unit and the bottom capsule unit can be configured to enclose the contracted balloon while it traverses the patient's esophagus. This helps the patient orally ingest the balloon with improved ease and safely. More specifically, the capsule can be configured to traverse the patient's esophagus from mouth to stomach, and then release the balloon into the stomach (usually upon application of either mechanical force to separate the balloon from the catheter, or alternatively by chemical action of stomach digestive fluids).

In some embodiments, the bottom capsule unit (304) can be configured to be biodegradable, whereas the top capsule unit can be configured to be both nondegradable, and attached permanently to the distal end of the intermedium catheter.

The top non-degradable capsule unit can be further configured with a shape and material designed to protect the patient's gastroesophageal junction from trauma, which is a risk when mechanical force is applied to the intermedium catheter and balloon to detach the intermedium catheter from the expansion valve portion of the balloon's regulator. In this embodiment, the top unit may be made from a soft and easily deformable, or other non-traumatic non-degradable material, so that it does not injure the gastroesophageal junction at this step.

Sensing Technology:

In order to properly manage implantation and management of the gastric balloon device, it is useful to employ various types of sensing technology that provides information to the physician regarding the status of the various components.

In some embodiments, the intermedium catheter (in particular the distal end of this catheter), expansion valve and timing valve, or other components of the system may further comprise one or more sensors or transmitters. These sensors or transmitters can be configured to help provide information pertaining to the present location of the distal end of the catheter relative to its position in the patient's gastrointestinal system.

In some embodiments, the balloon system may further comprise electromagnetic tracking system. This balloon based electromagnetic system can comprise any of sensors and transmitters which emit an electromagnetic field, sensors coupled to an external electromagnetic unit, or recorder connected to the outside world by a wireless or sonic transmitter, optical fiber, or a wire connector. In some embodiments, the sensor can be located within either the regulator and/or in the intermedium catheter.

As previously discussed, these sensors can be wireless, or can be connected with a wire which runs along the length of the intermedium catheter and emerges from the proximal end of the catheter, and there be connected to an external display, computer system, recording device, and the like. This sensor and the associated wire system (if any) will typically have a diameter less than the intermedium catheter, and in some embodiments can be and are located within the hollow portion of the catheter. These sensors can, for example, track the movement of the catheter and capsule by monitoring the position and orientation in the three-dimensional gastrointestinal space inside the patient.

In some embodiments, sensors can be located within the regulator, can be configured track the position and orientation of the regulator (and the attached balloon), and report this wirelessly. Using such methods, the movement and location of the regulator and attached components (e.g. the balloon, the catheter if still attached) can be tracked throughout the patient's gastrointestinal system.

Such tracking is useful, because one possible complication of gastric balloon implantation can be obstruction and/or perforation of the patient's gastrointestinal tract. Here, tracking of the balloon (here usually in the deflated state) can detect the balloon's passage in through the patient's small intestine and large intestine, detect potential obstruction, and can help prevent perforation.

In some embodiments, these sensors can comprise any of pH sensors, pressure or force sensors, chemical sensors, temperature sensors, proximity sensors, infrared or radiofrequency sensors connected readout devices (e.g. outside readout devices) by any of a wired or wireless link. The transmitters can comprise radiofrequency transmitters, light transmitters, infrared transmitters, and sonic or ultrasonic transducers. In another embodiment, optical fiber imagers or video camera (e.g. video sensors), optionally with video image analytics can also be included on the intermedium catheter or the capsule. Such imaging systems can help provide direct visualization of the location of the capsule or the balloon.

Use Example

To administer the balloon, the deflated balloon is encased in the capsule as previously described, and this capsule is attached to the distal end of the previously described intermedium catheter. The capsule, here attached to the catheter, is ingested by the patient. The process of esophageal peristalsis helps the capsule travel to the patient's stomach. While this is happening, various sensors and tracking systems can help monitor this progress in real time.

To monitor this progress, as previously discussed, the sensors or the electromagnetic tracking system can facilitate navigation and positioning in the stomach without the requirement of a clear sight. Alternatively, correct positioning in the stomach can be directly visualized by a small camera located on the intermedium catheter. As yet another alternative, the acidic pH in the stomach can be detected by pH sensors, and this information can be used to confirm placement of the capsule in the stomach. As another alternative, pressure sensors can be used to take pressure measurements of the esophagus, lower esophageal sphincter and stomach, and this information can also be used to verify that the capsule has been correctly positioned in the stomach. Additionally, prior art medical imaging methods, such as direct visualization by endoscopy, X-ray, fluoroscopy, ultrasound medical imaging techniques can also be utilized to confirm proper capsule placement in the stomach.

Once the capsule is positioned inside the patient's stomach, in some embodiments, the capsule will then degrade when the capsule encounters the acidic environment/digestive fluids in the patient's stomach, releasing the balloon.

The balloon can then be expanded with pressurized gas (such as air or nitrogen) or fluid (such as water and normal saline). This pressurized gas or liquid can be delivered using a port that is positioned on the proximal end of the intermedium catheter. This gas or fluid causes expansion of the balloon, and causes the expanded balloon to in turn occupy a significant volume inside the stomach, and creating a dead space in the stomach, and helping to induce satiety.

Various electromagnetic sensors, positioned at various places such as within the regulator, or at the distal tip of the intermedium catheter, can also track the enlargement of the balloon as it inflates, providing real-time feedback on the balloon's expansion. In some embodiments, these sensors can also be used to measure the volume of the expanded balloon. Alternatively or addition, the volume of the expanded balloon can also be estimated by measuring the amount of gas or fluid delivered to the balloon, and/or by measuring the pressure inside the balloon.

Once the balloon has expanded to the desired volume, the balloon can be separated from the catheter, completing the installation of the balloon in the stomach, by detaching the intermedium catheter and the expansion pin from the expansion valve portion of the regulator, as previously described.

In its expanded state, the balloon will typically occupy a comparatively large-sized three-dimensional volume in the expandable stomach lumen. Note that in the expanded state, the balloon is designed and intended to reside exclusively in the patient's stomach.

In some embodiments, the expanded polymeric balloon can be removed from the stomach (either at the end of the predetermined period, or at some earlier time) using standard endoscopy methods. Here, for example, the polymeric balloon may be punctured with injection needles or other methods, and the deflated balloon can then be removed using standard endoscopic equipment.

However, as previously discussed, in a preferred embodiment, once the balloon deflates (often by way of the timing portion of the regulator), the balloon is configured so that it can pass by natural peristaltic action through the patient's gastrointestinal system; stomach, small and large intestine. Here, the deflated balloon leaves the patient's body by spontaneous contraction of the balloon and then the natural passage of contracted balloon from the stomach to the anus and into the toilet. This in vivo, spontaneous contraction of the balloon in the stomach, results after the degradable element in the timing valve portion of the regulator has degraded, thus allowing the balloon's internal pressurized gas or fluid to exit the balloon.

Other Applications:

The device and system described herein can additionally, in some embodiments, be used for sustained delivery of drugs, medications, or other therapeutic material, Here, for example, such therapeutic material can be delivered on the skin of the balloon, or alternatively or filled within the balloon. Here, the rate and timing of the release of the therapeutic agent from the interior of the balloon in the gastrointestinal tract can be controlled by controlling the degradation of the degradation element within the timing valve of the regulator.

In addition to helping assist in balloon placement, the previously described sensors can also be used for other purposes as well. For example, such sensors can be used to detect temperature changes ingestion; decreases in stomach pH, and other types of data for time periods ranging from hours to months.

Examples

As previously discussed, the system includes a balloon 100 (shown and explained in conjunction with FIG. 1), regulator 104 embedded in the balloon (shown and explained in conjunction with FIG. 1 and FIG. 3), a capsule 300 containing the folded balloon (shown and explained in conjunction with FIG. 9), a intermedium catheter 200 with proximal and distal ends (shown and explained in conjunction with FIG. 6), an expansion pin 210 (shown and explained in conjunction with FIG. 7), sensors and tracking system located within the intermedium catheter and or the regulator (shown and explained in conjunction with FIGS. 11 and 12), and a three-way stopcock 212 (shown and explained in conjunction with FIG. 8).

Figure 1B:
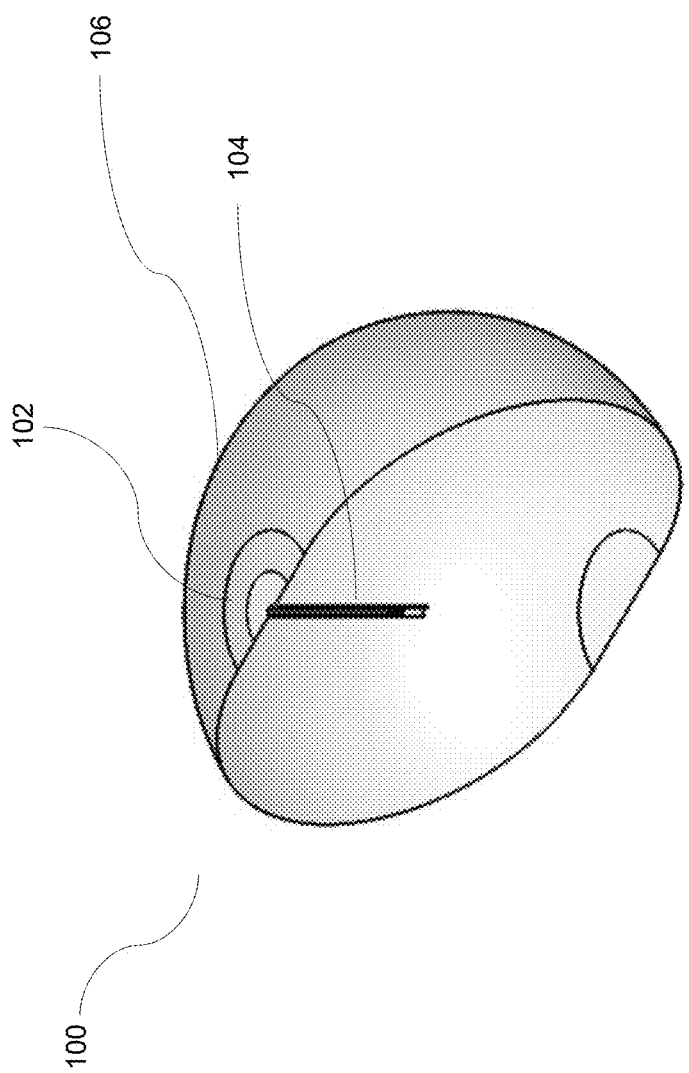
FIG. 1B illustrates a cross-sectional view of the expanded balloon 100, in accordance with at least one embodiment.
Figure 1C:
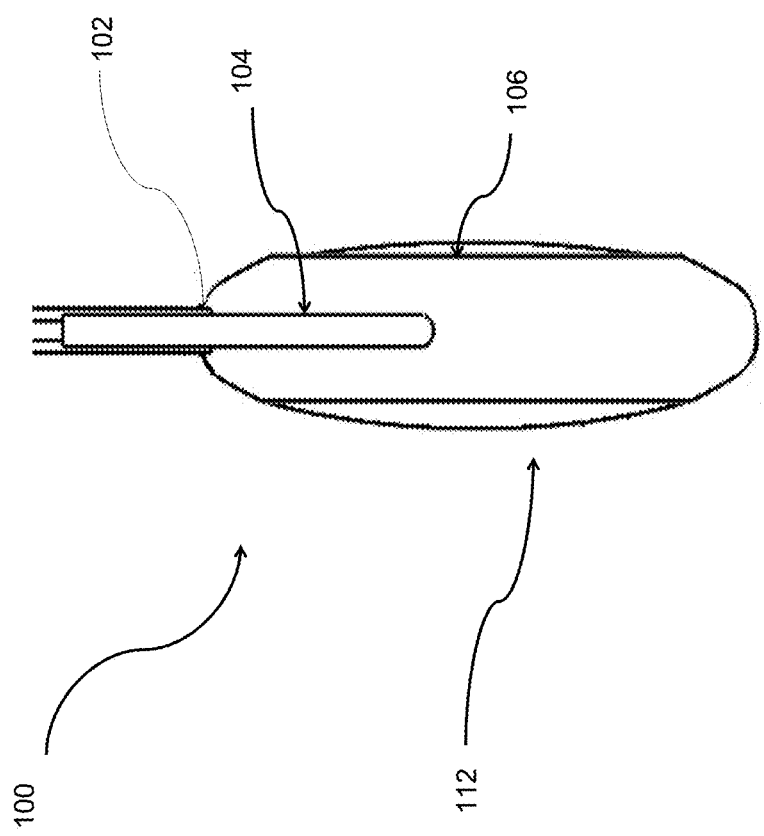
FIG. 1C illustrates a contracted view of the balloon 100, in accordance with at least one embodiment.

The present invention provides a minimally invasive device a balloon 100 intended for diagnostic and therapeutic purposes such as weight loss. Such gastrointestinal balloon device 100 when allowed to reside within the gastric lumen can decrease oral intake and induce satiety by various mechanism; by occupying space in the stomach, it creates a dead space which cannot be utilized for food storage, balloon 100 also stretches the stomach which sends signals to the brain via vagus nerve to inhibit hunger center and thus decreasing appetite. The device 100 can also decrease gastric motility and alter the hormones mainly leptin and ghrelin which results in partially sustained suppression of appetite after removal or passage of the device from the stomach. The present invention discloses a system and method for treating obesity. Moreover, the devices, methods, and systems described herein are not limited to treatment of obesity and can even be applied to a diagnostic and therapeutic area outside of obesity The balloon 100 comprises a thin flexible polymeric skin 106 enclosing an interior volume; the balloon 100 is capable of transitioning between an expanded state 110 (FIG. 1A) and a contracted state 112 (FIG. 1C). FIG. 1A illustrates an expanded view of the balloon 100, in accordance with at least one embodiment. FIG. 1B illustrates a cross-sectional view of the expanded balloon 100. FIG. 1C illustrates a contracted view of the balloon 100, in accordance with at least one embodiment. The skin 106 is ultra-thin, flexible to allow a small contracted state 112. A regulator 104 is embedded within the skin 106 of the balloon. Regulator 104 controls the transition of the balloon 100 to expanded state and again to contracted state.

Skin 106 has highly elastic and flexural properties to allow for elongation and recovery; it easily transitions to a large expanded state 112. The skin 106 in a contracted state can be easily folded to a small diameter safe for ingestion. The skin 106 of the balloon is extremely lightweight, smooth and non-traumatic to avoid any mechanical complications.

The inner side of the skin 106 of the balloon 100 in the expanded state 110 is in contact with the pressurized gases or fluid used for expansion of the balloon while the outer side of the skin of the balloon is exposed to the stomach environment. The skin 106 of the balloon is strong and stable; chemical, abrasion & impact resistant and non-degradable to survive in the stomach environment. The skin 106 has properties for easy sterilization and biocompatibility. In one example skin, 106 of the balloon is made of a variety of polymeric materials such as polyurethane, silicone, and pellethane, etc.

Figure 2A:
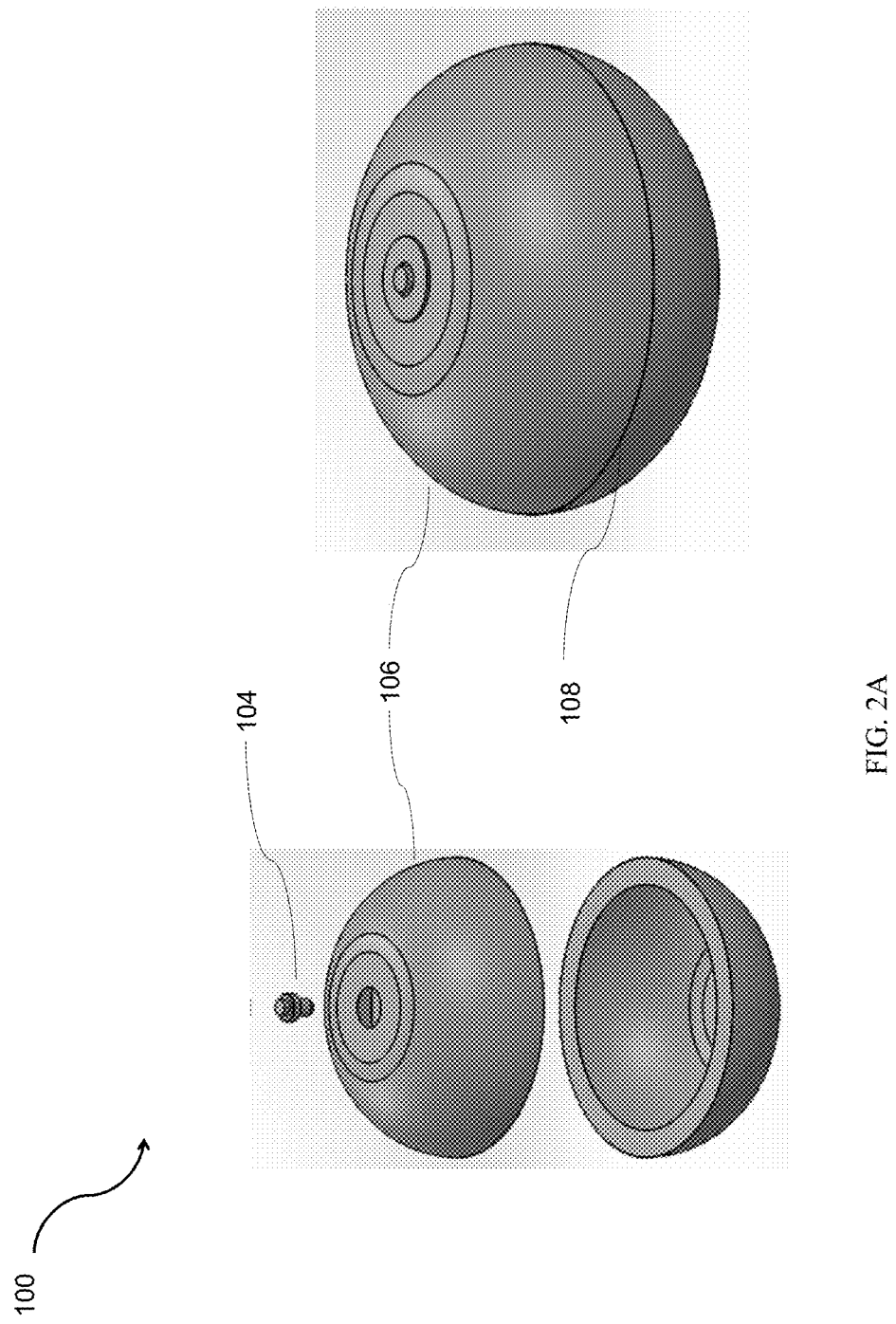
FIG. 2A illustrates an example of a balloon 100 formed by bonding 108 of two units of skin 106.
Figure 2B:
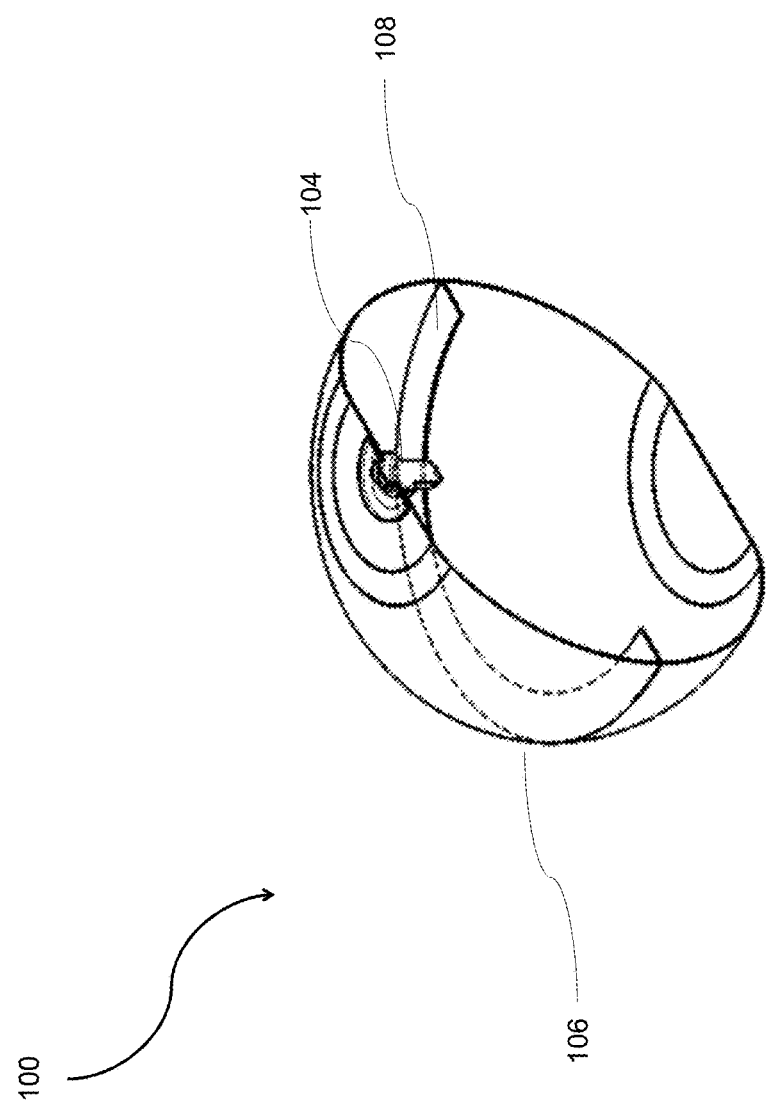
FIG. 2B illustrates a cross-sectional view of the balloon 100 as shown in FIG. 2a with the bonding region 108.
Figure 2C:
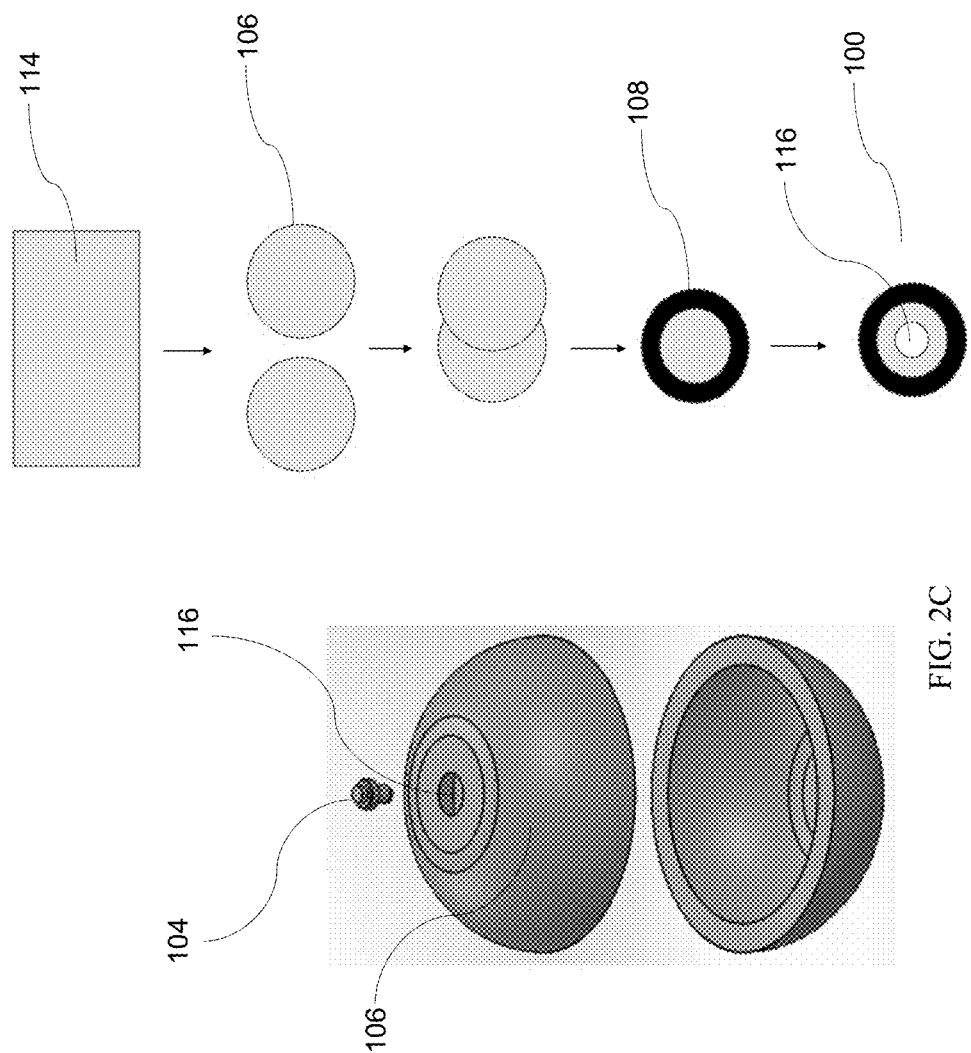
FIG. 2C illustrates an example of the process of balloon 100 by bonding 108 of two halves of skin 106.

The skin 106 either comprises a single unit of polymeric material or it can be formed by bonding or adhesion of two or more units. FIG. 1A illustrates a balloon 100 comprises a single unit of polymeric skin 106 with a neck, the regulator 104 is embedded in the neck 102. In one example the balloon 100 is formed by bonding 108 of two units of skin 106. FIG. 2A illustrates an example of a balloon 100 formed by bonding 108 of two units of skin 106. FIG. 2B illustrates a cross-sectional view of the balloon 100 as shown in FIG. 2a with the bonding region 108. FIG. 2C illustrates an example of the process of making a balloon 100 by bonding 108 of two halves of skin 106. The skin 106 comprises two circles formed by cutting or molding a thin polymeric sheet 114 in a circular shape. The two circular halves of the skin 106 are aligned together and bonded 108 or sealed off together in the periphery. Small hole 116 is made in one of the circular halves of the skin 106; the regulator 104 is tightly embedded in the hole 116 (FIG. 2C).

Figure 1D:
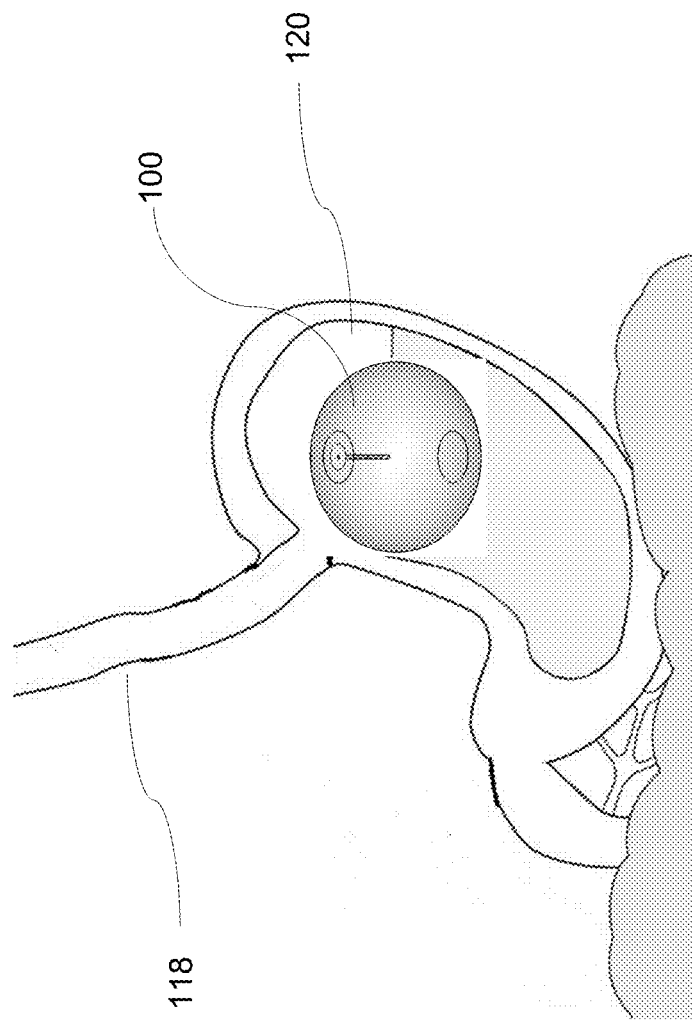
FIG. 1D illustrates an exemplary view of an expanded balloon 100 in the stomach 120 of a patient, in accordance with at least one embodiment.

The balloon 100 in the first stage is configured in a contracted state (FIG. 1C) for ingestion and passage in the gastrointestinal system starting from the esophagus 118 of a patient. After ingestion by a patient, in the second stage the balloon 100 is configured in an expanded state (FIG. 1B) to reside in the gastrointestinal system. In an embodiment, the balloon 100 can only reside in the stomach 120 in an expanded state. FIG. 1D illustrates an exemplary view of an expanded balloon 100 in the stomach 120 of a patient. Stomach is a highly expandable largest diameter space in the gastrointestinal system, while the other parts of the gastrointestinal system are narrower tubular structures. The dimensions of the balloon 100 are configured such that the volume of the balloon 100 can only be accommodated in the stomach. Therefore the balloon 100 in an expanded state resides in the stomach. In one example, the balloon 100 when used in the stomach have an expanded dimension of diameter at least greater than 2.5 cm or an interior volume at least greater than 300 milliliters, therefore can only reside in the stomach in the expanded state. In other examples for the use of the device in other parts of the gastrointestinal system, smaller expanded volumes can be used.

The present balloon 100 (in the expanded state), is configured to occupy the stomach volume 120 and reduce the stomach space availability for food intake. This expanded state balloon 100 is capable of inducing a satiety feeling so that the patient limits his/her food intake. The present balloon 100 slows down the movement of the food and liquid passing through the stomach thus induces the feeling of satiety sooner and reduces the amount of food intake further. The present balloon device 100 can also instigate hormonal changes to assist in weight loss.

Figure 1E:
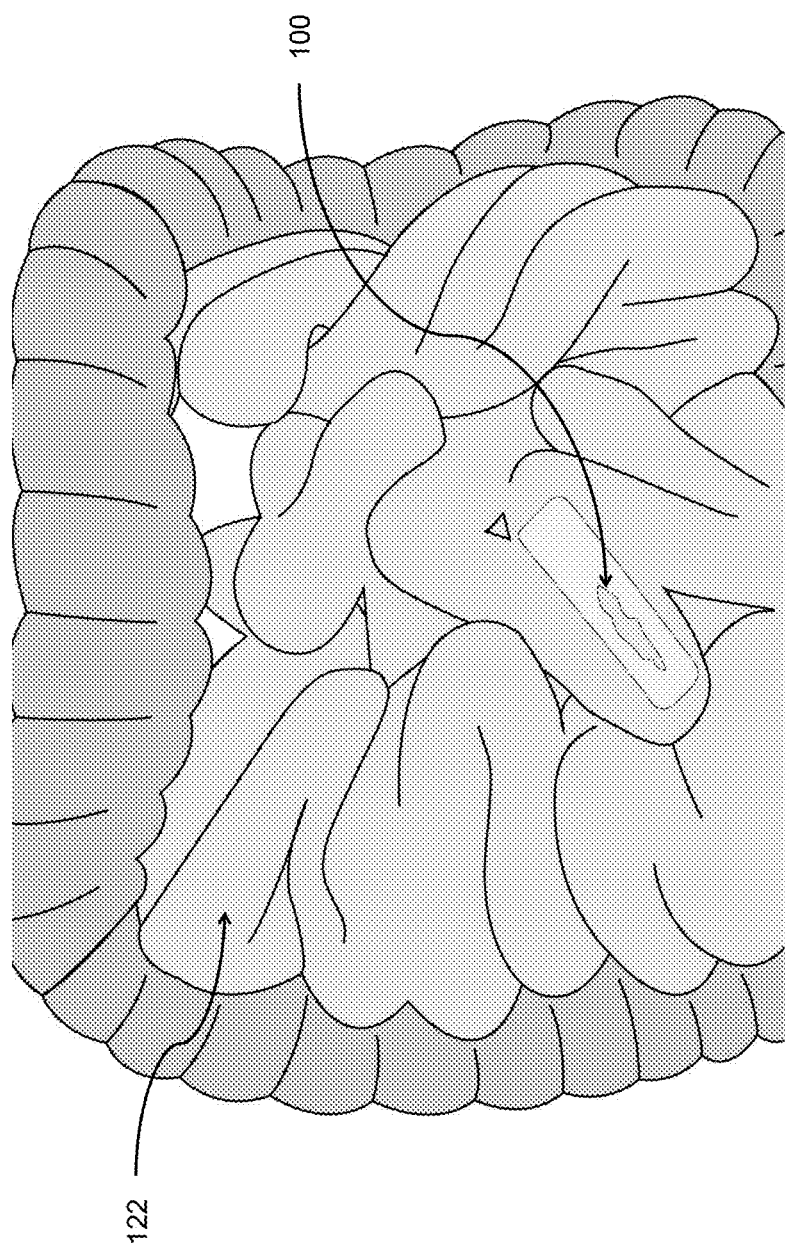
FIG. 1E illustrates an exemplary view of a contracted balloon 100 passing the intestine 122 of a patient.

The balloon 100 in the third stage is configured to undergo spontaneously contraction and passage in a contracted stage through the gastrointestinal system from the stomach, past the patient's pyloric sphincter, into the intestine and out of the anus of a patient. FIG. 1E illustrates an exemplary view of a contracted balloon 100 passing the intestine 122 of a patient. In an embodiment, the balloon 100 has a contracted state dimensions of less than 2 centimeters diameter and less than 5 centimeters in length, and configured so that in the contracted state, the balloon 100 can pass from a stomach 120 of a patient completely through a gastrointestinal tract of a patient. The physiological narrowing within the gastrointestinal tract from stomach to anus are pylorus (pyloric sphincter) and ileocecal valve and duodenal sweep is a physiological angulation. Usually, ingested material greater than 2 cm in diameter will not pass through the pylorus, or ileocecal valve and material longer than 5 cm will not pass through the duodenal sweep. Therefore, if the dimensions of the contracted balloon 100 are less than 2 cm in diameter and less than 5 cm in length they should pass through the intestine into the toilet with peristalsis unless there is there pathological stenosis of the gastrointestinal tract.

The regulator 104 is embedded in the skin 106 spanning from interior to an exterior of the balloon 100 as shown in FIG. 1A. The regulator 104 comprises an outer opening 128 in the exterior portion for entry of fluid or gas, hollow stem 130, an inner opening 132 in the circumference wall of the hollow tube's hollow stem for passage of gas and fluid into the interior of the balloon and a closed end 134 with a covering 136. The regulator 104 functionally is a combination of an expansion valve 124 or the flow regulator unit and the timing valve 126 or the timing regulator unit forming an adjustable one-way valve. FIG. 3A illustrates a view of the regulator 104 comprising the expansion valve 124 and timing valve 126, in accordance with at least one embodiment.

The expansion valve portion 124 is configured to in a first open mode, permit any of outside pressurized gas and fluid to enter balloon 100 and cause the balloon 100 to transition from a contracted state to the expanded state and in a second closed mode, prevent any of internal pressurized gas and fluid from using the regulator to exit the balloon 100. The expansion valve 124 in the first open mode only allows gas and fluids to enter the balloon 100 when they are injected specifically in the opening 128 in the outer portion of the regulator at a pressure higher than the intragastric pressure. The injected gas or the fluid enters the regulator 104 from the opening 128 and then passes through the hollow stem 130 and exits the regulator from the inner opening 132 to enter the interior of the balloon resulting in transition of the balloon to an expanded state. After the expansion of the balloon, the opening 132 closes to prevent exit of gas and fluid from the expanded balloon to the outside. In the first and second closed mode of the expansion valve, the end 134 remains closed to prevent any of internal pressurized gas and fluid from using the closed end 134 to exit the balloon. Expansion valve 124 in any mode at any time will not allow entry of gastric contents in the interior of the balloon 100.

In one example, the expansion valve in the first open mode allows entry of gases or fluid up to a specified volume e.g. 700 ml (700 milliliters) If volume of more than 700 ml is injected than expansion valve automatically switches into the second closed mode. The second closed mode in this example not only prevents any internal gas and fluid to exit the balloon 100 but also prevents further entry of any fluid and gases thus preventing over-expansion and bursting of the balloon 100. In another example to avoid over expansion of the balloon 100 with more than the desired volume e.g. 700 ml, the opening 128 in the outer portion of the regulator 104 disconnects from the expansion pin. The expansion pin is temporarily connected to the regulator 104, when the pressure in the interior of the balloon 100 rises above the maximum point of expansion, applying more pressure to fill the balloon disconnects the temporary connection between the expansion pin and the regulator 104. In another example expansion valve 124 in the second closed mode prevents internal pressurized gas and fluid to exit the balloon 100 only up to the intended limit e.g. 700 ml, volume more than 700 ml can exit the balloon 100 thus keeping the volume constant at 700 ml.

In one example regulator 104 comprises a hollow cylindrical tube 138 spanning from an interior to an exterior of the balloon 100, closed end 134 of the hollow cylindrical tube towards the interior of the balloon, outer opening 128, hollow stem 130 and inner opening 132 in the lateral wall of the cylindrical tube. FIG. 3b illustrates an example of a hollow cylindrical regulator 104, in accordance with at least one embodiment. The expansion valve portion 124 of the regulator comprises inner openings 132 in the tube 138 and an elastic polymeric sheath 140. This is a hollow sheath, and this hollow sheath can often be configured in the form of a hollow cylinder. The cylindrical tube 138 comprises opening 132 in the lateral wall located in the interior of the balloon 100. The openings 132 can be of any shapes such as round, oval, triangle, rectangle etc. The cylindrical tube 138 is covered circumferentially with a elastic non degradable polymeric sheath 140 for e.g polyurethane or silicone along its entire length and extending few millimeters beyond the cylindrical tube 138 into the interior of the balloon 100. Most of the inner surface of the sheath 140 is in contact with the outer surface of the cylindrical tube 138, while the outer surface of the sheath 140 is in contact with the interior gas or fluid. The space 142 between the outer surface of cylindrical tube 138 and the inner surface of the sheath 140 is dynamic which opens and closes based on the differential pressure applied on the inner surface by the injection of gas or fluid and outer surface of the sheath 140 by the interior gas and fluid. In the first open mode of expansion valve, the space 142 is open and permits pressurized gas and fluid when injected at the outer opening 128 to enter the balloon 100 through the inner opening 132. In the first open mode higher pressure is exerted from injected gases and fluid on the inner surface of the sheath 140 than the outer surface, therefore the sheath 140 separates from walls of the cylindrical tube 138 and forms a narrow passage to permit gas or fluid to pass from inner opening 132 into the interior to cause expansion of the balloon 100. The pressure required for injection of gas or fluid to enter the balloon is in part dependent on the space 142. Properties of the space 142 are determined by the properties such as flexibility, elasticity etc of the material of the sheath 140. In one example the sheath 140 is highly elastic and separates from the walls of the tube 138 with small pressure from injected gas or fluid, so that the balloon can be easily expanded. After the complete expansion of the balloon 100 when the injection of pressurized gases and fluid are stopped, the expansion valve switches to the second closed mode. In the second closed mode this space 142 is closed, and this prevent any internal pressurized gas and fluid from using the inner opening to exit the balloon. In the second closed mode more pressure is exerted on the outer surface of the sheath 140 by the pressurized gases or liquids in the interior of the balloon and no or smaller pressure is exerted on the inner surface of the sheath 140, thus sheath tightly approximates to the cylindrical tube 138 to close space 142 and the pathway along the opening 132 and prevents passage of any substances. The cylindrical tube with inner opening 132 and the polymeric sheath 140 forms a one-way valve system and allows passage of fluid or gases injected into the opening 128 of the regulator 104 but prevents exit out of the balloon 100.

Figure 3C:
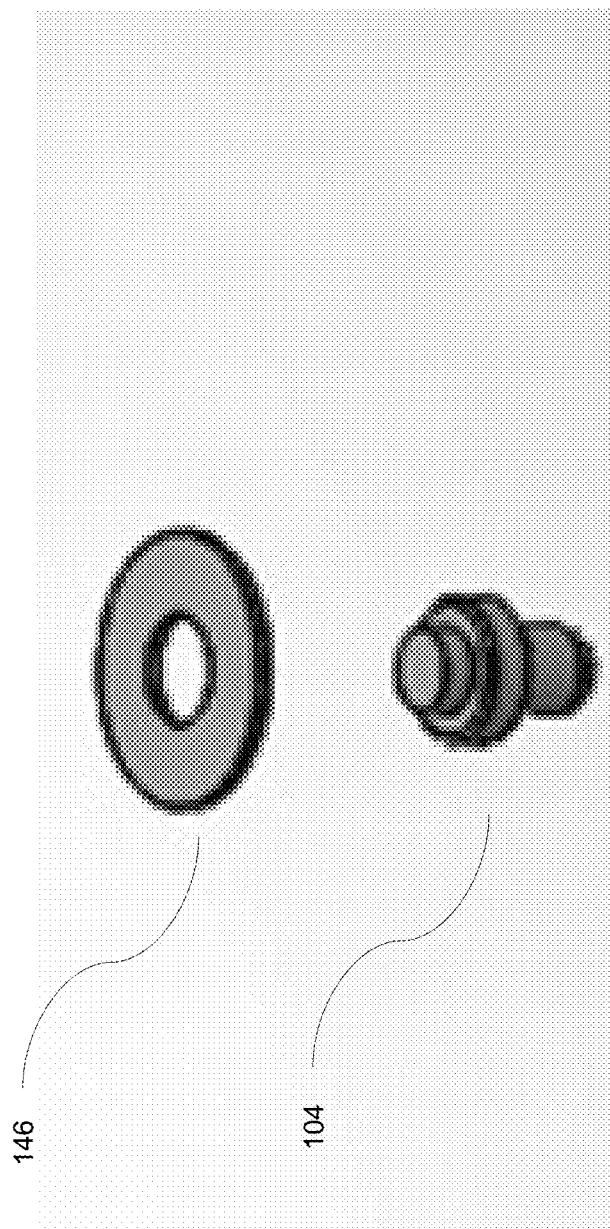
FIG. 3C illustrates an example of flap 146 along with the regulator 104.

The outer opening 128 of the regulator 104 is located on the exterior of the balloon 100 and forms a smooth continuous surface with the skin 106 of the balloon 100. Skin 106 is permanently attached to the lateral portion of the opening 128; the skin 106 keeps opening 128 fixed in place and provides support and stability. In another variation, the lateral wall of the outer opening 128 is attached to a ring or flap like support 146, the flap 146 configured to attach to the skin of the balloon. FIG. 3c illustrates an example of flap 146 along with the regulator 104. The closed end 134 of the cylindrical tube is freely suspended from the open end 128 into the interior of the balloon 100.

The regulator 104 may further comprise a timing valve portion 126 comprising a gas and fluid impermeable degradable element 144 (FIG. 3A). While the degradable element 144 is intact, it prevents any internal pressurized gas and fluid from using the regulator 104 to exit the balloon 100, thus maintaining the balloon in the state of expansion. After the degradable element 134 has degraded, it allows any internal pressurized gas and fluid to use the regulator 104 to exit the balloon 100 and thus to transition the balloon to a contracted state again.

In the above example of a hollow cylindrical regulator comprising the expansion 124 and timing valve 126 as shown in FIG. 3B, the timing valve portion comprises a biodegradable element or retainer 144 towards the interior end of the cylindrical tube 138. The interior end of the hollow cylindrical tube 138 towards the balloon 100 is closed or plugged by a biodegradable retainer plug 144 and does not allow entry of any pressurized fluid or gas into the balloon 100 from the closed end 134. The degradable retainer plug 144 is located below the inner opening 132 towards the interior of the balloon 100 within the cylindrical tube 138. The innermost surface of the retainer 144 is in contact with the interior of the balloon 100 pressurized gas or fluid; the lateral surface is in contact with the inner surface of the cylindrical tube 138 while the outermost surface lies towards the opening 132. The degradable retainer plug 144 remains intact until balloon 100 starts expanding with pressurized gas and fluid, after that, the degradation of the retainer will be triggered. The complete degradation of the retainer creates a direct pathway between the interior of the balloon 100 to the exterior stomach leading to leakage of the pressurized gas and fluid into the stomach and eventually leading to contraction of the balloon 100.

The time that the balloon remains in the expanded state, and the time until the balloon contracts, is a function of the properties of the degradation element or the retainer. These properties can include the physical dimensions and the nature of the degradable material and the environment to which degradation element is exposed. The degradation element can be configured so that it starts degrading after it comes in contact with the desired gases or fluids. The degradation can begin at the surface of the degradation element, once this surface comes into contact with desired fluids or gases.

In the above example shown in FIG. 3B, the degradable retainer plug 144 can be of a cylindrical or similar aspect, with dimensions of length and diameter. This plug can be fitted longitudinally inside a cylindrical tube 138. The retainer 144 can have an appropriate diameter to tightly fit in the cylindrical tube, but can have a variable length. The surface at the two ends of the retainer being in direct contact with fluid or gases, degradation process will start at the ends and move towards the center of the retainer until it has completely degraded. The larger the length of the retainer more time will be required to complete the degradation process, therefore the length of the retainer is directly proportional to the time for complete degradation and the expanded state of the balloon 100 when material and environment are constant. Thus, the time of the expanded state of the balloon 100 can be controlled from hours to years by changing the length of the retainer. Since the entire surface area of the degradable retainer plug in contact with the liquid or gases will start degrading irrespective of the diameter. Therefore in the above example of a cylindrical retainer, the degradation time will be partially or fully independent of the total surface area exposed or the diameter of the retainer. By contrast, keeping the length constant, but changing the diameter of the degradable retainer plug, will tend to have a minimal effect on the degradation time.

The timing valve can be configured with variable degradation times, and thus the balloon can have an extended state ranging from a hours to year. This controllable degradation timer can be utilized to individualize treatment according to patient needs. For example, one patient may desire or require a balloon duration of 3 months, while the other patient may require a balloon for 12 months. Two different balloons, one with an extended state of 3 months, and the other with 12 months, can be created by setting length of the degradable element/retainer in the timing valve portion, while keeping the other parts the same. Very short extended state timing is sometimes desirable, because balloons with an extended state of only hours to days can be utilized for diagnostic testing and collection of data from the gastrointestinal tract.

Assuming that other factors, such as the dimensions and environment are constant, the degradation rate and time of the timing valve will generally be directly dependent on the degradable element material. The degradable material utilized in the present invention is typically chosen to be biocompatible. Various materials, such as miscible, semi-miscible or immiscible materials can be used to "buy" or control the degradation time. The degradation rate for the miscible materials will generally be triggered upon contact with the desired degradation agent like water, saline, or nitrogen, etc. By contrast, the degradation rate for the semi-miscible materials may remains static upon contact with degradation agent.

Various degradable polymers can be utilized in the present invention, these polymers can be either natural or synthetic, but synthetic polymers having advantages of an extensive range of properties and uniformity than the natural biodegradable materials, are preferred for this application. The biodegradable material can be hydrolytically degradable polymers or enzymatically degradable polymers. Hydrolytically degradable polymers are materials that possess hydrolytically labile chemical bonds in their backbone and can be broken down without secondary influence into one part with a hydrogen atom and the other part with a hydroxyl group. Some degradable polymers possess bonds that are susceptible to hydrolysis including esters, anhydrides, acetals, carbonates, amides, urethanes and phosphates. Some of the biodegradable material suitable for the present invention includes polymers of L-lactide, D lactide, DL-lactide, glycolide, c-caprolactone, a-esters, hydroxyalkanoates, propylene fumarate, etc. Co-polymerization of these two or more monomers can also create a suitable material with desired glass transition point, melting point, and a tensile modulus of elasticity, tensile strength, and elongation and degradation time. For example Polyglycolide (PGA) is the simplest linear aliphatic polyester which is highly crystalline (45-55%), with a high melting point (220-225° C.) and a glass-transition temperature of 35-40° C.; material form PGA lose about 50% of their strength after 2 weeks and 100% at 4 weeks, and are completely absorbed in 4-6 months. Poly(c-caprolactone) a polymer of ε-caprolactone yields a semicrystalline polymer with a melting point of 59-64° C., glass-transition temperature of −60° C. and a degradation time in the order of 2 years. Another degradable material Polylactide (PLA) is the cyclic dimer of lactic acid isomers, d, and l. l-lactide is the naturally occurring isomer, and dl-lactide is the synthetic blend of d-lactide and l-lactide. Poly(dl-lactide) (DLPLA) is an amorphous polymer with a random distribution of d-lactide and l-lactide is unable to arrange into an organized crystalline structure, has lower tensile strength, higher elongation, and a much more rapid degradation time, making it more attractive for a shorter degradation time applications. The homopolymer of l-lactide (LPLA) is about 37% crystalline, with a melting point of 175-178° C. and a glass-transition temperature of 60-65° C., degradation time is much slower than that of DLPLA, requiring more than two years to be completely absorbed. Copolymers of l-lactide and dl-lactide have also been made to disturb the crystallinity of l-lactide and accelerate the degradation rate. Two monomers can also be copolymerized to extend the range and optimize the properties of a homopolymer. For example, Poly(lactide-co-glycolide), a copolymer of polyglycolide and poly(l-lactide) can have different properties depending on the proportion of each homopolymer. For example, a copolymer of 50% glycolide and 50% dl-lactide degrades faster in 1-2 months and a copolymer of 90% glycolide and 10% l-lactide within 3-4 months.

Figure 3D:
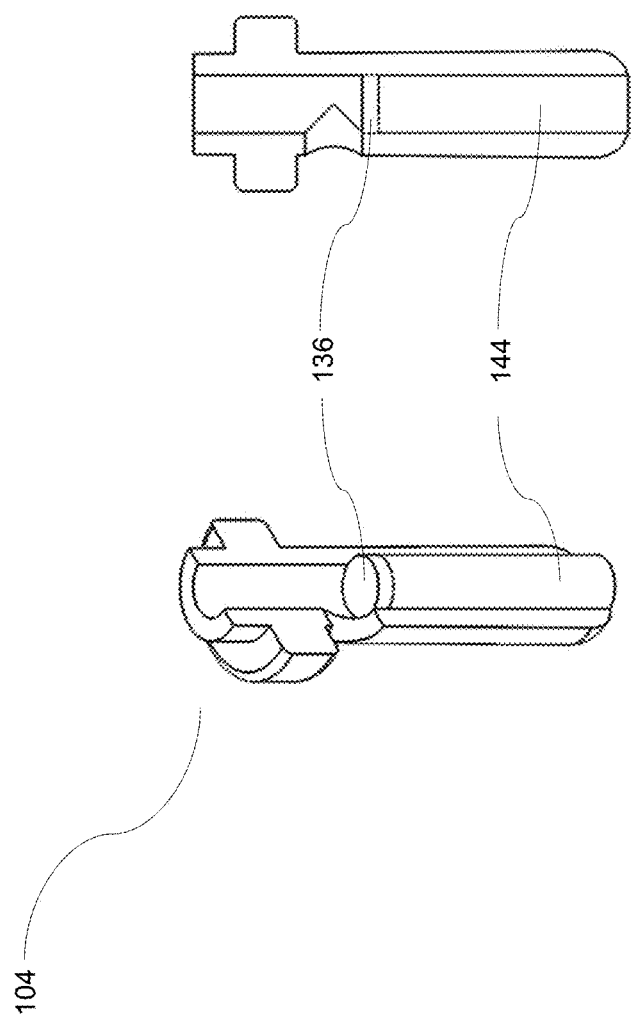
FIG. 3D illustrates an example of a regulator 104 comprising of degradable retainer plug 144 covered by a non-degradable film 136.

Degradation time and rate of the degradable element in the timing valve will also depend on the environment the degradation element is exposed. The stomach is a highly acidic environment with constant physical and biochemical changes; the degradation of the degradation element can be very unpredictable if it is in contact with the stomach environment. The environment in the interior of the balloon can be constant and easily controlled and can consist of fluid such as water, normal saline, etc. or gases such as nitrogen, etc. at the body temperature and desired Ph. In one example the exterior end of the degradable element or retainer 144 is covered with a non-degradable polymeric film 136. FIG. 3D illustrates an example of a regulator 104 comprising of degradable retainer plug 144 covered by a non-degradable film 136. In this example, the degradation process starts from the inner end of the retainer 144 which is in contact with the interior of the balloon fluid or gases. The film 136 completely covers the retainer preventing any exposure of to the outside stomach environment and allowing degradation in a controlled environment within the interior of the balloon 100. The innermost portion of the retainer 144 is in contact with contents of the balloon 100 starts degradation first, while the external part covered by the film 136 degrades last. After the degradable retainer plug 144 degrades completely the film 136 is displaced or opens up and allow pressurized fluid or gases to exit the balloon 100. The film 136 supported by the degradable retainer plug 144 remains in a stable, fixed position until the degradable retainer plug 144 completely degrades. After that, the thin film 136 is unable to withstand the pressure from the fluid or gases in the interior of the balloon 100 and is displaced out the regulator 104 to allow fluid or gases to exit the balloon 100. The shape of the film 136 depends on the retainer 144, for example if the degradable retainer plug 144 is cylindrical, the film 136 can be of circular dimension covering the entire outer end of the retainer.

Figure 3E:
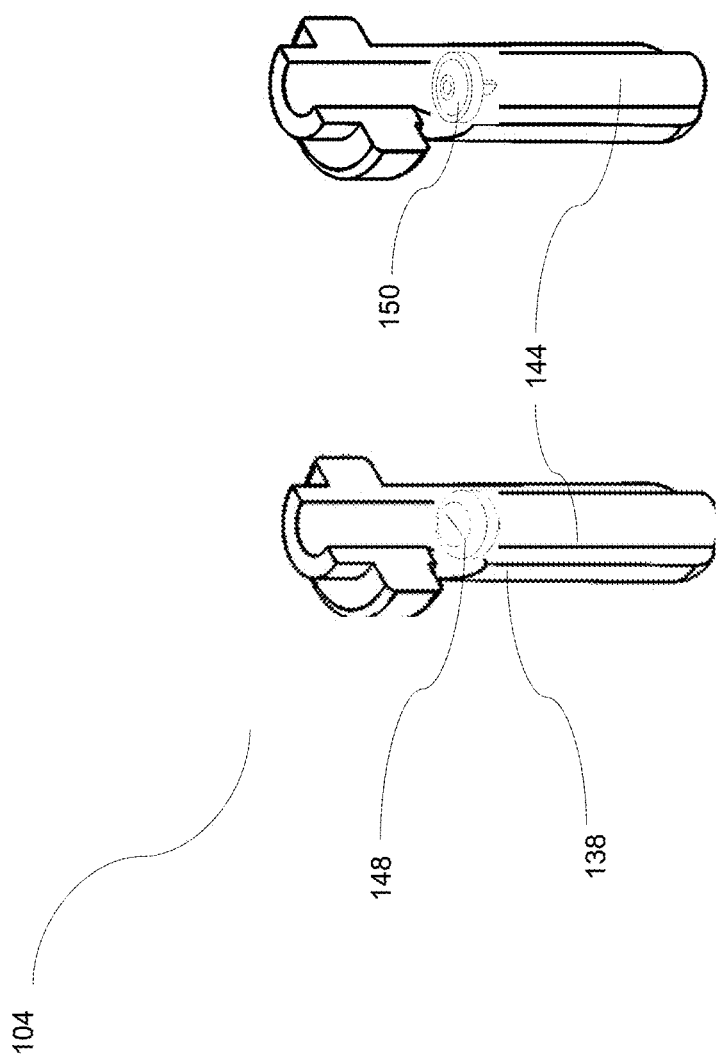
FIG. 3E illustrates an example of a regulator 104 comprising of degradable retainer plug 144 covered by a non-degradable membrane valve 148 or a non-degradable duckbill valve 150.

In another example, the film 136 is replaced by a simple one-way valve system, for example, a membrane valve 148 comprising of two semi-circular films overlapping in the middle while the semicircular portion is loosely attached to the walls of the cylindrical tube 138. FIG. 3E illustrates an example of a regulator 104 comprising of degradable retainer plug 144 covered by a non-degradable membrane valve 148. Both the membranes are supported by the outer end of the retainer 144 from below. The membrane valve system 428 prevents gastric contents to enter and come in contact with the retainer 144 until the retainer is intact. After the retainer 144 is fully degraded the membrane valve system 148 loses the support and opens up, thus allowing the gases or fluids to exit the balloon 100.

In other examples, the outer portion of retainer 144 is fully covered by one-way valves such as duckbill valve 150 or an umbrella valve or a combination of two; the one-way valve is in direct contact with gastric contents on outer side and the retainer 144 on the other side; the one way valve is configured to prevent gastric contents from entering the balloon through the valve system but allows the gases or fluid to exit the balloon but only after the retainer 144 is fully degraded. FIG. 3E illustrates an example of a regulator 104 comprising of degradable retainer plug 144 covered by a non-degradable duckbill valve 150.

Once the balloon 100 is inflated with the desired gas or liquid, the degradable element 144 starts out in an intact state. After inflation, however, degradation of degradable element 144 will typically begin (or will be triggered). The degradable element 144 can comprise hydrolytically or enzymatically degradable polymers. In some embodiments, the interior of balloon 100 can further comprise a biocompatible chemical or enzymatic material configured to degrade the degradable element 408 into a biocompatible degraded material over a time range between hours to years when balloon 100 is stored at approximately 37 degrees centigrade.

Figure 3F:
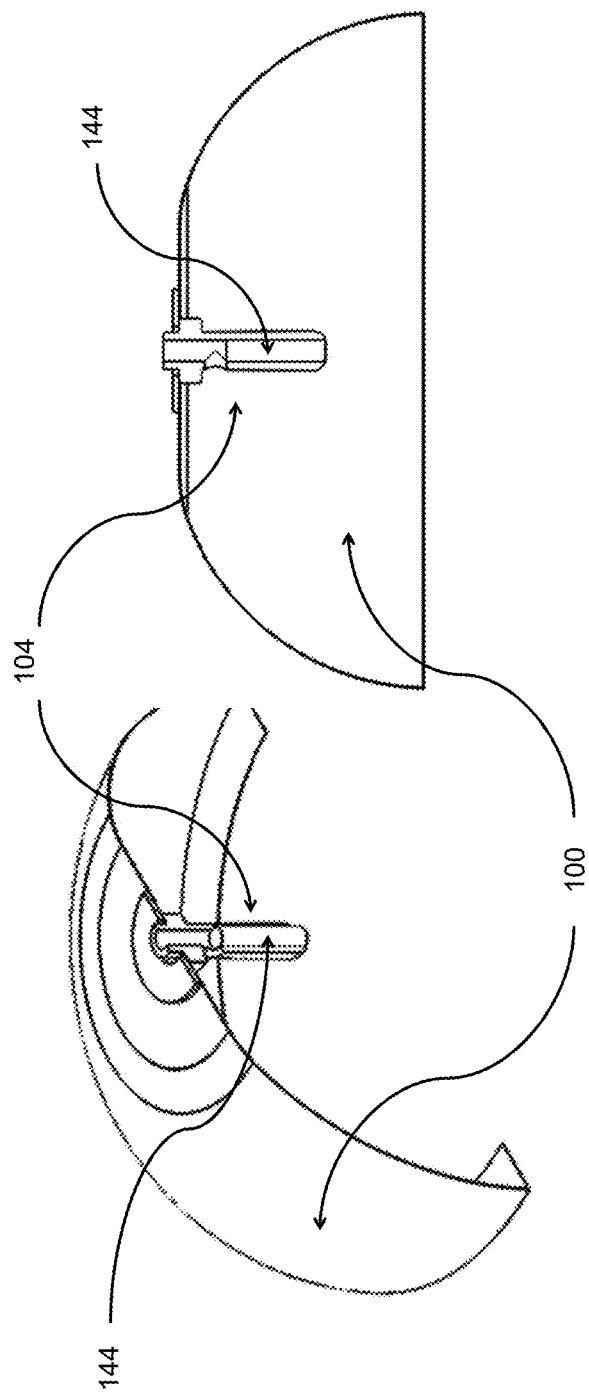
FIG. 3F, FIG. 3G and FIG. 3H illustrate the degradation process of the degradation element 144 in the regulator 104, in accordance with at least one embodiment. The degradable element 144 is intact shown as in FIG. 3F. The degradable element 144 has degraded halfway through the designated length, shown as in FIG. 3G. The degradable element has wholly degraded through the entire designated length, demonstrated in FIG. 3H.
Figure 3G:
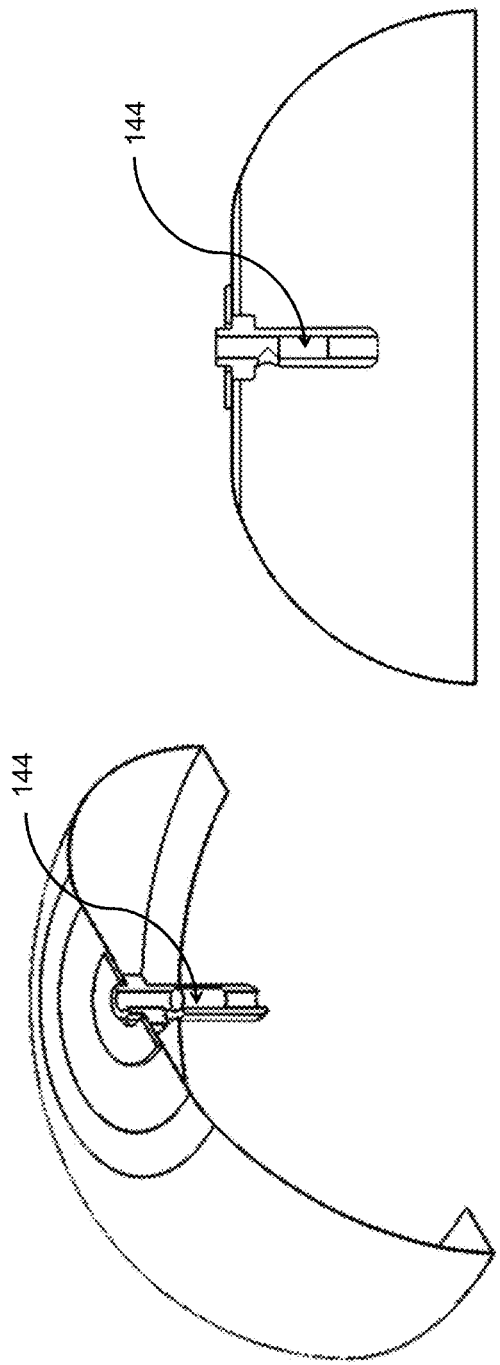
Figure 3H:
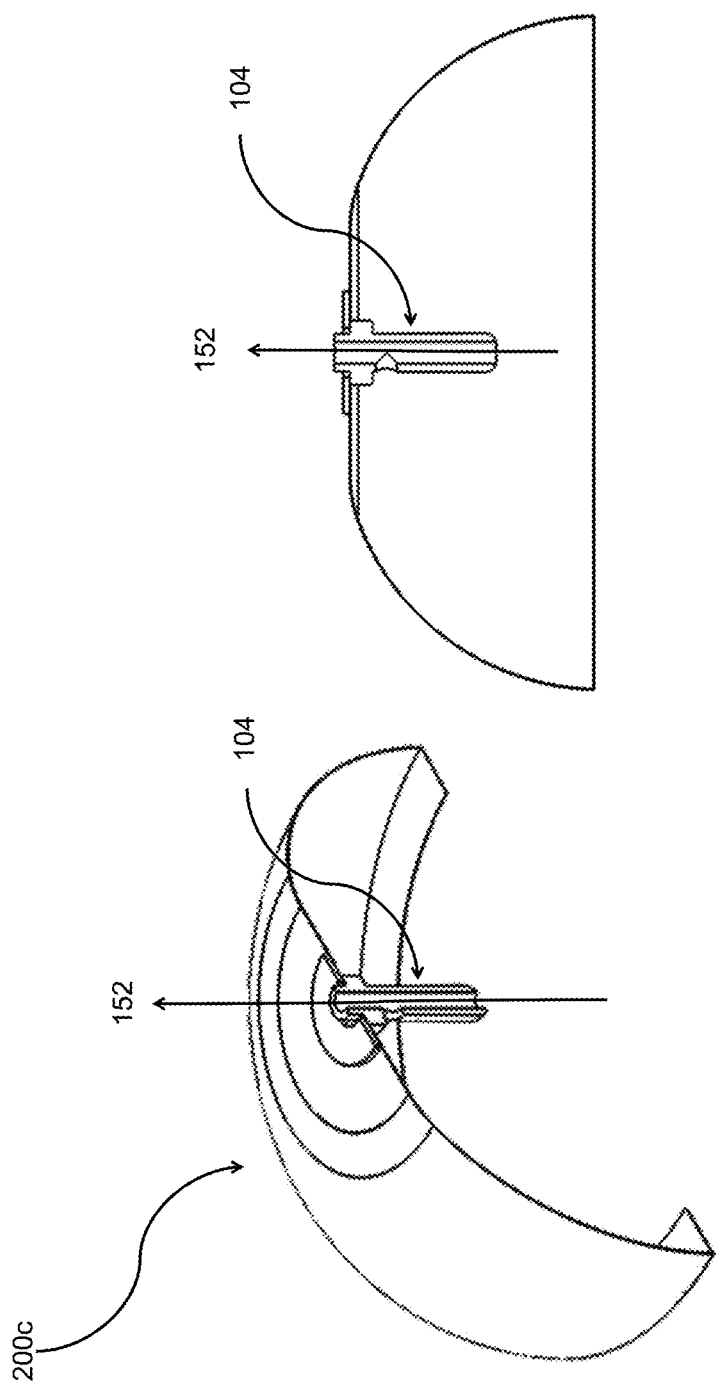

FIGS. 3F, 3G and 3H illustrate the degradation process of the degradation element 144 in the regulator 104, in accordance with at least one embodiment. In FIG. 3F, the degradable element 144 is intact. In FIG. 3G, the degradable element 144 has degraded halfway through the designated length. In FIG. 3H, the degradable element has wholly degraded through the entire designated length. When this happens (FIG. 3H) the regulator 104 now has a direct pathway 152 between the interior and exterior of the balloon 100. This allows the fluid or gas within the balloon to now exit the balloon.

Figure 3I:
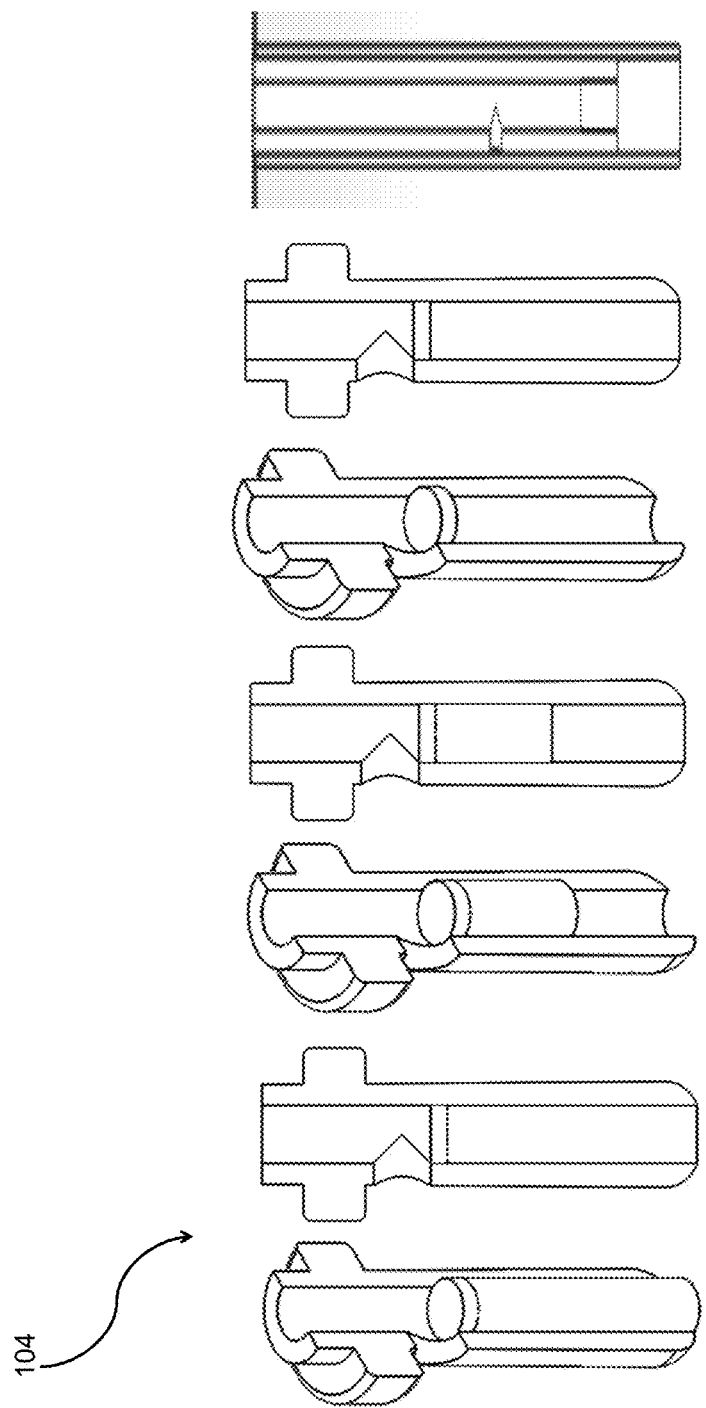
FIG. 3I illustrates an exemplary view of the various configurations of a cylindrical or similar dimension regulator 104, in accordance with at least one embodiment.

FIG. 3I illustrates an exemplary view of the various configurations of a cylindrical or similar dimension regulator 104, in accordance with at least one embodiment. There are many variations of the regulator 104 comprising the expansion and the timing valve.

Figure 3J:
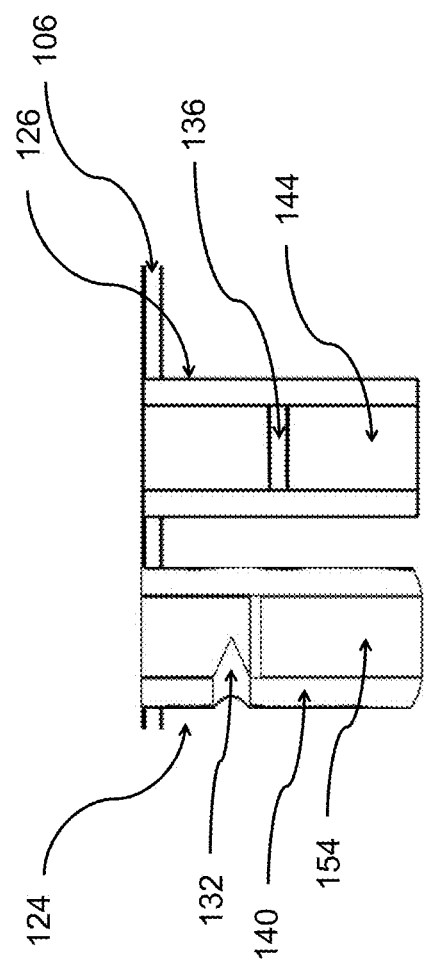
FIG. 3J illustrates an example where the timing valve 126 is separate from the expansion valve 124 and is embedded in different locations on the skin of the balloon.

FIG. 3J illustrates an example where the timing valve 126 is separate from the expansion valve 124 and is embedded in different locations in the skin 106. The expansion valve portion 124 is a one-way valve comprising a non-degradable closed end or a plug 154 towards the interior of the balloon 100, one or more inner openings 132, and sheath 140 entirely covering the expansion valve 124. The timing valve 126 portion can be separate from the other portions, and in some embodiments can be located in different location on the skin 106; and can comprise a degradable element 144 with a non-degradable covering 136. The expansion valve and timing valve can be cylindrical or any other shaped tube attached to the skin 106 of the balloon 100.

FIG. 3K illustrates another example of an alternative embodiment of regulator 104, in which the expansion valve 124 and timing valve 126 are separate valves, but are attached together to form one unit embedded in a same location in skin 106. In this example, the cylindrical tube 138 is longitudinally divided into two compartments by a wall 156. Here one compartment contains the expansion valve 124 comprising non-degradable closed end or a plug 154 towards the interior end and opening 132, whereas the other compartment contains the timing valve portion 126 comprising a degradable element 144 with covering 136. The lateral walls of the entire cylindrical tube 138 are here covered with a non-degradable sheath 140.

In some embodiments, the timing valve portion can be completely made of degradable material so that when it is fully degraded, gas and fluid are able to exit the balloon 100. In another embodiment the timing valve separates or falls off when the biodegradable material is fully degraded, and gas and fluid can exit the balloon 100.

In one example, the regulator 104 can exclude the timing valve portion and only consist of the expansion valve. The timing valve can be simply eliminated from the regulator 104 if the degradable element or retainer 144 is non-degradable material, such as a sealing gel, and thus permanently prevents any internal pressurized gas and fluid from exiting the balloon 100. The balloon 100 in this example will not be able to automatically pass through the stomach and therefore will need to be manually removed from the stomach with endoscopy at the end of the desired time period.

The regulator 104 can have several other different design features depending on the needs. For example, the regulator 104 can have a duckbill design, umbrella design, combination duck umbrella valve, diaphragm design, slit valve design or another type of design.

Figure 3L:
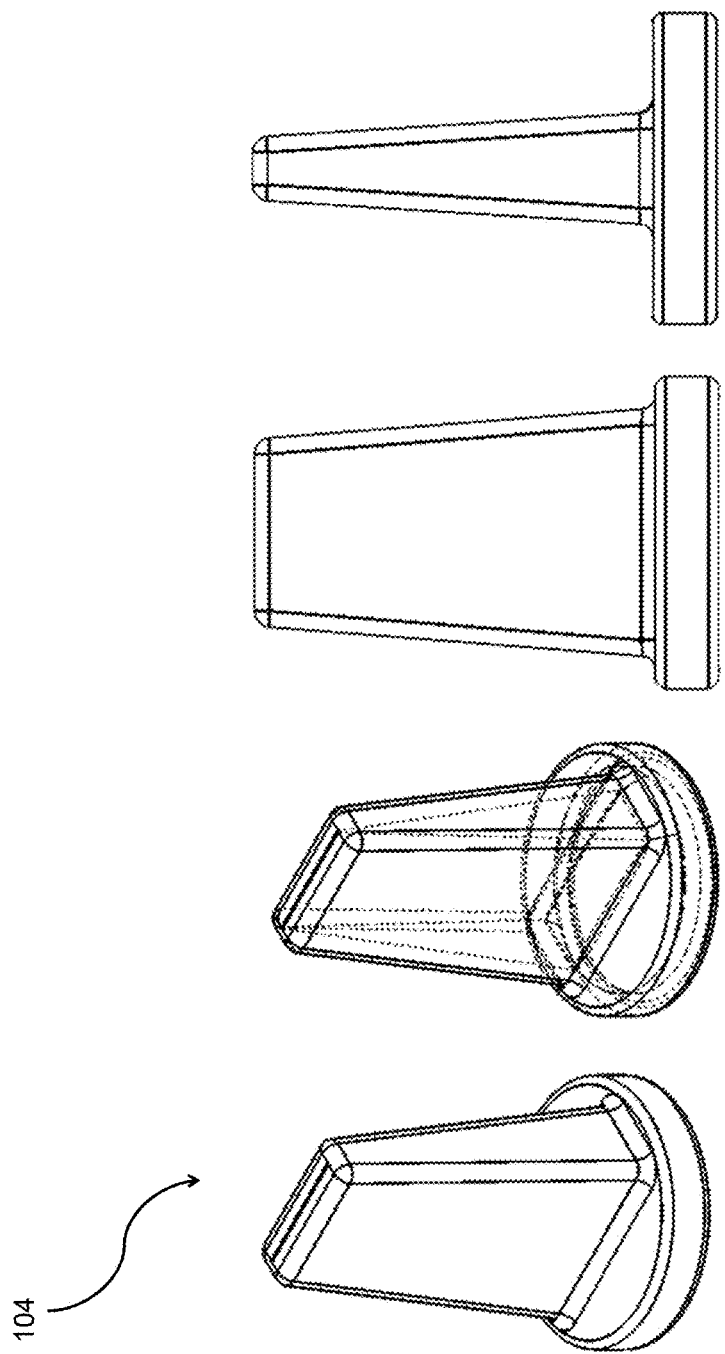
FIG. 3L illustrates a duckbill design view of the regulator 104, in accordance with at least one embodiment.
Figure 3M:
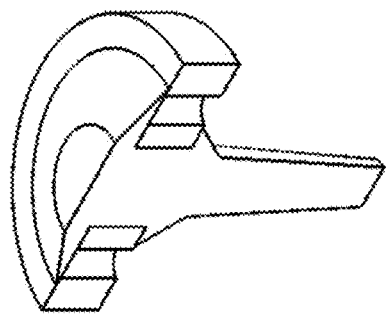
FIG. 3M illustrates a closed state view of an umbrella design of the regulator 104, in accordance with at least one embodiment.
Figure 3M:
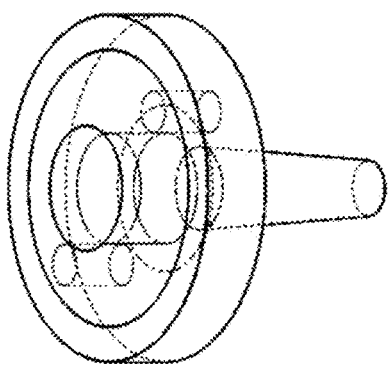
Figure 3M:
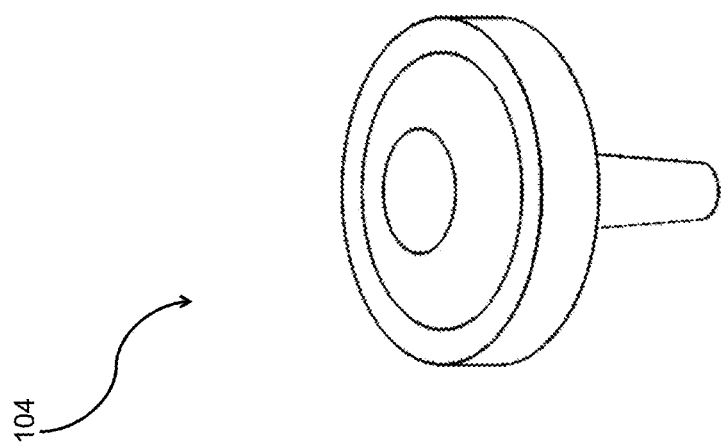
Figure 3N:
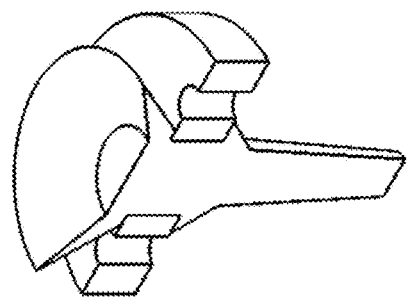
FIG. 3N illustrates an opened state view of an umbrella design of the regulator 104, in accordance with at least one embodiment.
Figure 3N:
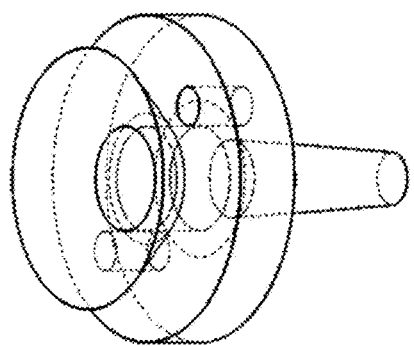
Figure 3N:
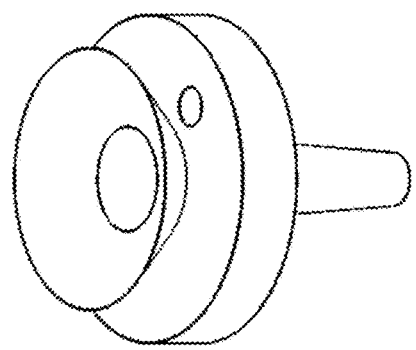
Figure 3O:
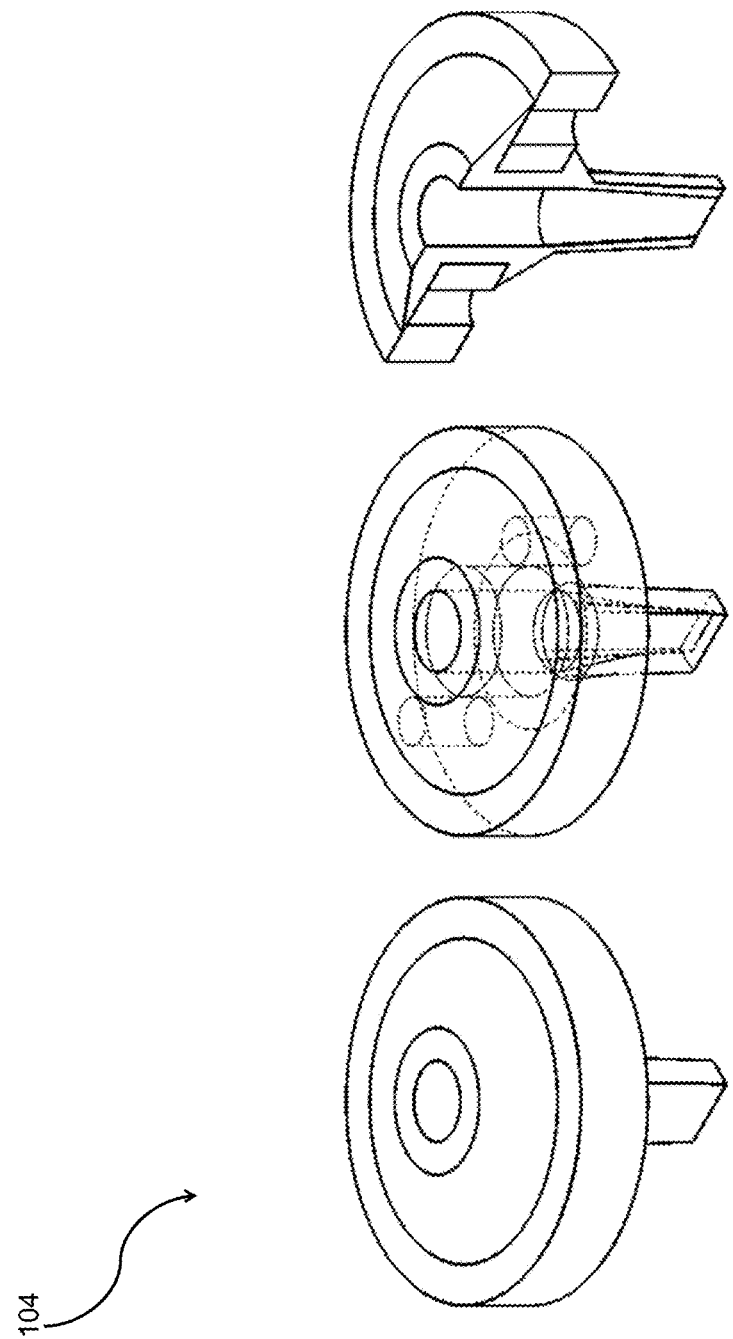
FIG. 3O illustrates a closed state view of a combination duck umbrella of the regulator 104, in accordance with at least one embodiment.
Figure 3P:
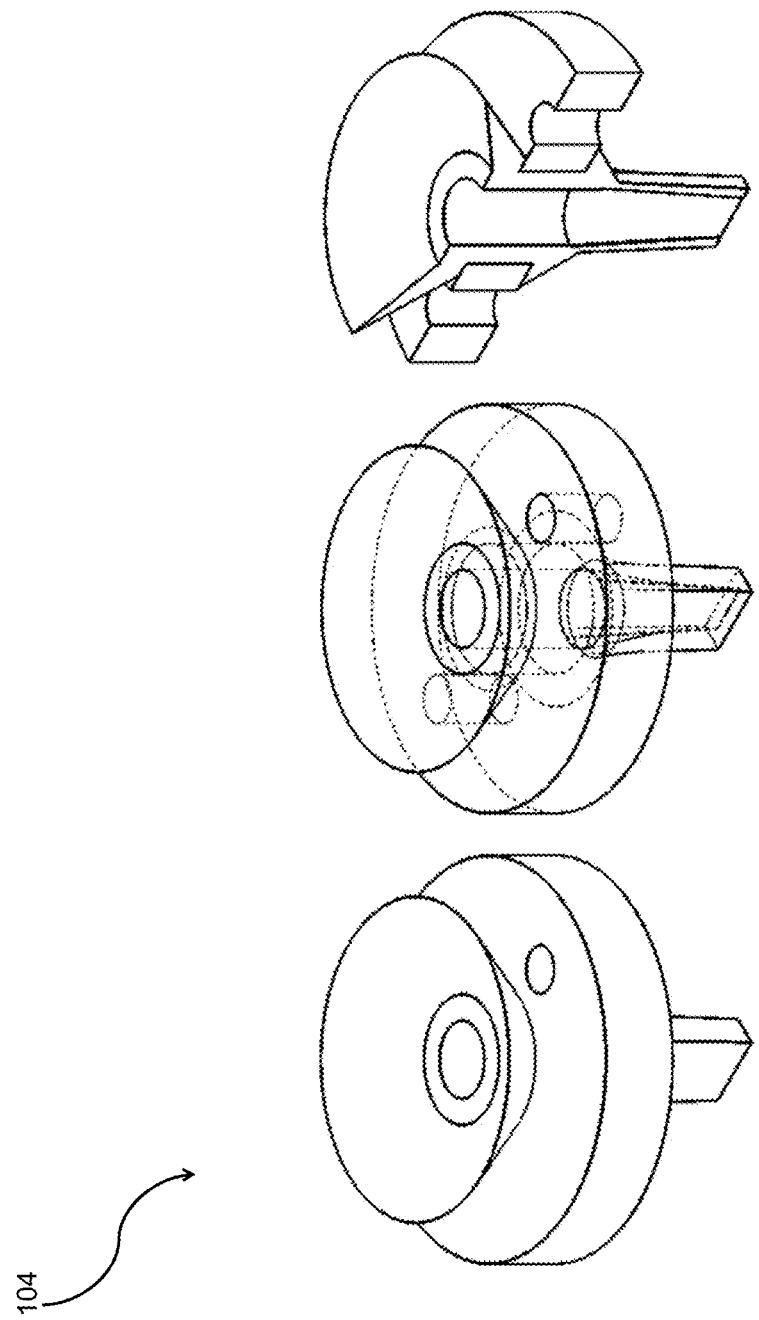
FIG. 3P illustrates an opened state view of a combination duck umbrella of the regulator 104, in accordance with at least one embodiment.
Figure 3Q:
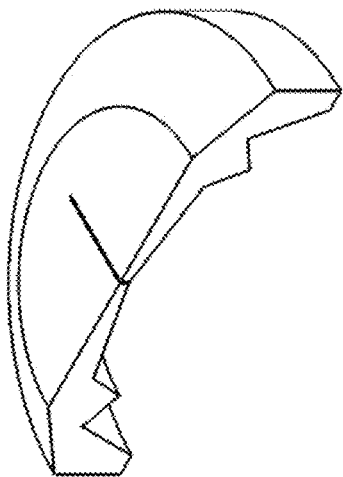
FIG. 3Q illustrates a closed state view of a diaphragm design of the regulator 104, in accordance with at least one embodiment.
Figure 3Q:
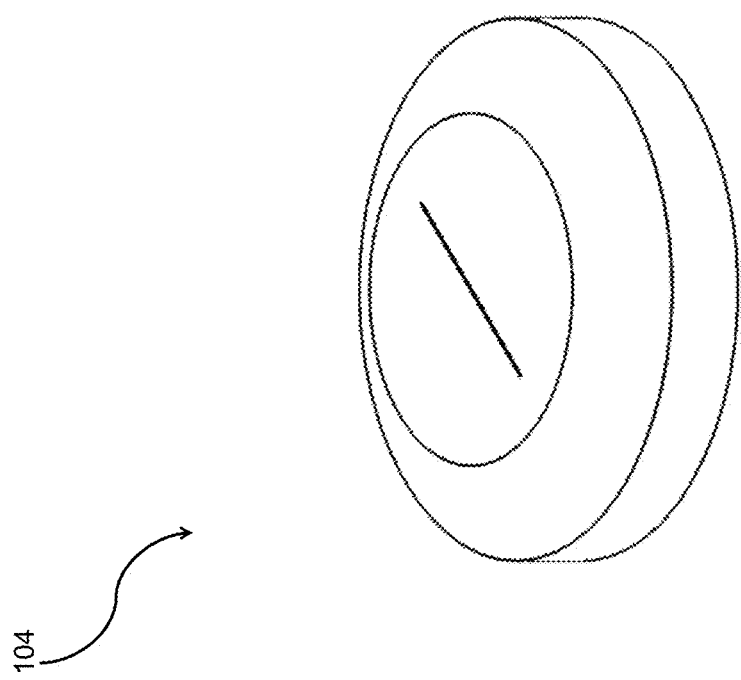
Figure 3R:
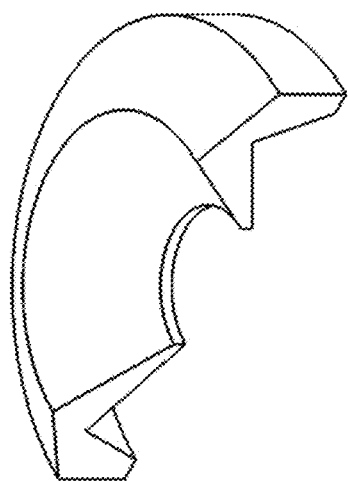
FIG. 3R illustrates an opened state view of a combination duck umbrella of the regulator 104, in accordance with at least one embodiment.
Figure 3R:
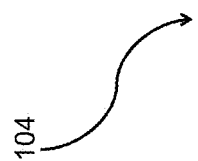
Figure 3R:
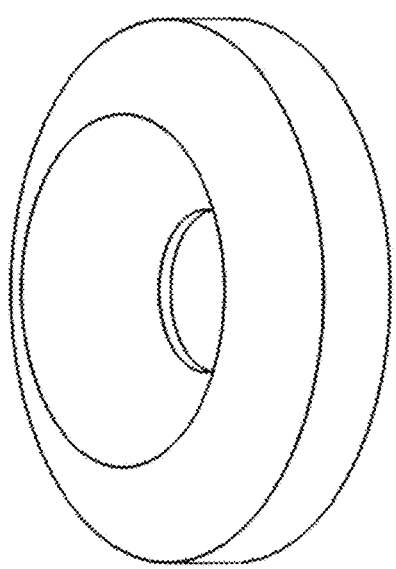

FIG. 3L illustrates a duckbill design view of the regulator 104, in accordance with at least one embodiment. FIG. 3M illustrates a closed state view of an umbrella design of the regulator 104, in accordance with at least one embodiment. FIG. 3N illustrates an opened state view of an umbrella design of the regulator 104, in accordance with at least one embodiment. FIG. 3O illustrates a closed state view of a combination duck umbrella of the regulator 104, in accordance with at least one embodiment. FIG. 3P illustrates an opened state view of a combination duck umbrella of the regulator 104, in accordance with at least one embodiment. FIG. 3Q illustrates a closed state view of a diaphragm design of the regulator 104, in accordance with at least one embodiment. FIG. 3R illustrates an opened state view of a combination duck umbrella of the regulator 104, in accordance with at least one embodiment.

When the balloon 100 is in an expanded state in the gastrointestinal tract, contraction of the balloon into a collapsed state can be achieved by several other design features. In one aspect the entire skin 106 of the balloon 100 or the parts of the skin 106 can further comprise degradable materials configured to dissolve, causing the balloon to burst or contract, over a time range between hours and year, when the balloon is in contact with gastrointestinal digestive fluids. In another aspect the entire regulator 104 or components of the regulator 104 can be degradable.

Figure 4A:
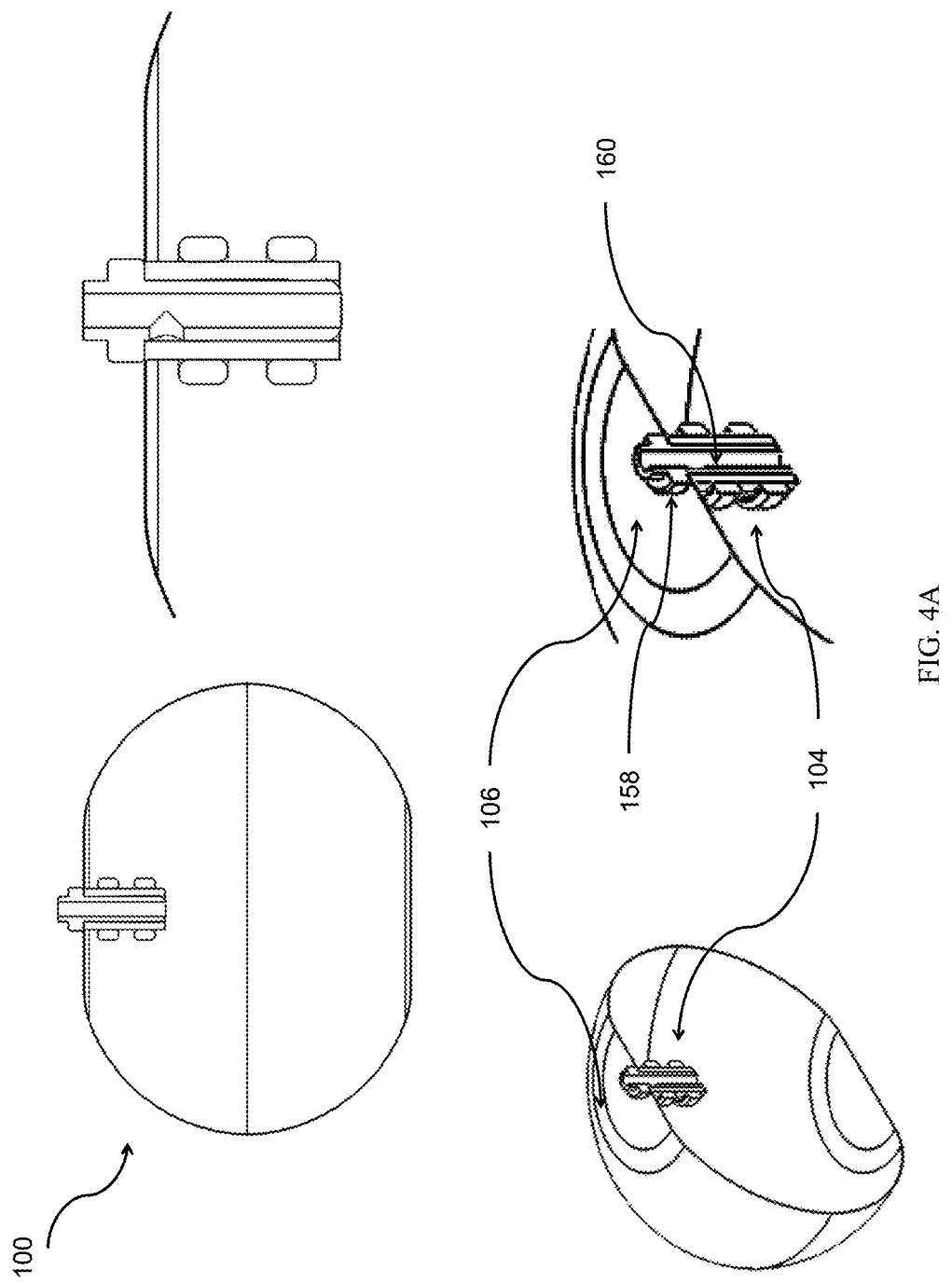
FIG. 4A illustrates an example wherein the valve 160 is attached to the skin 106 with one or more degradable bands 158.

There are various other methods for including the degradable material within the balloon device 100. These are shown in FIGS. 4A-4F. FIG. 4A illustrates an example wherein the valve 160 is attached to the skin 106 with one or more degradable bands 158. The valve comprises a one-way expansion valve 160, covered on the outside with a degradable band 158. Here this degradable band 158 functions as its own type of timing valve or timer, because when the degradable band is intact, any internal pressurized gas and fluid is unable to exit the balloon 100. However after the degradable band 158 has degraded, the valve 160 is no longer attached to the skin 106. Once the valve 160 is released, any internal pressurized gas and fluid can then exit the balloon 100.

Figure 4C:
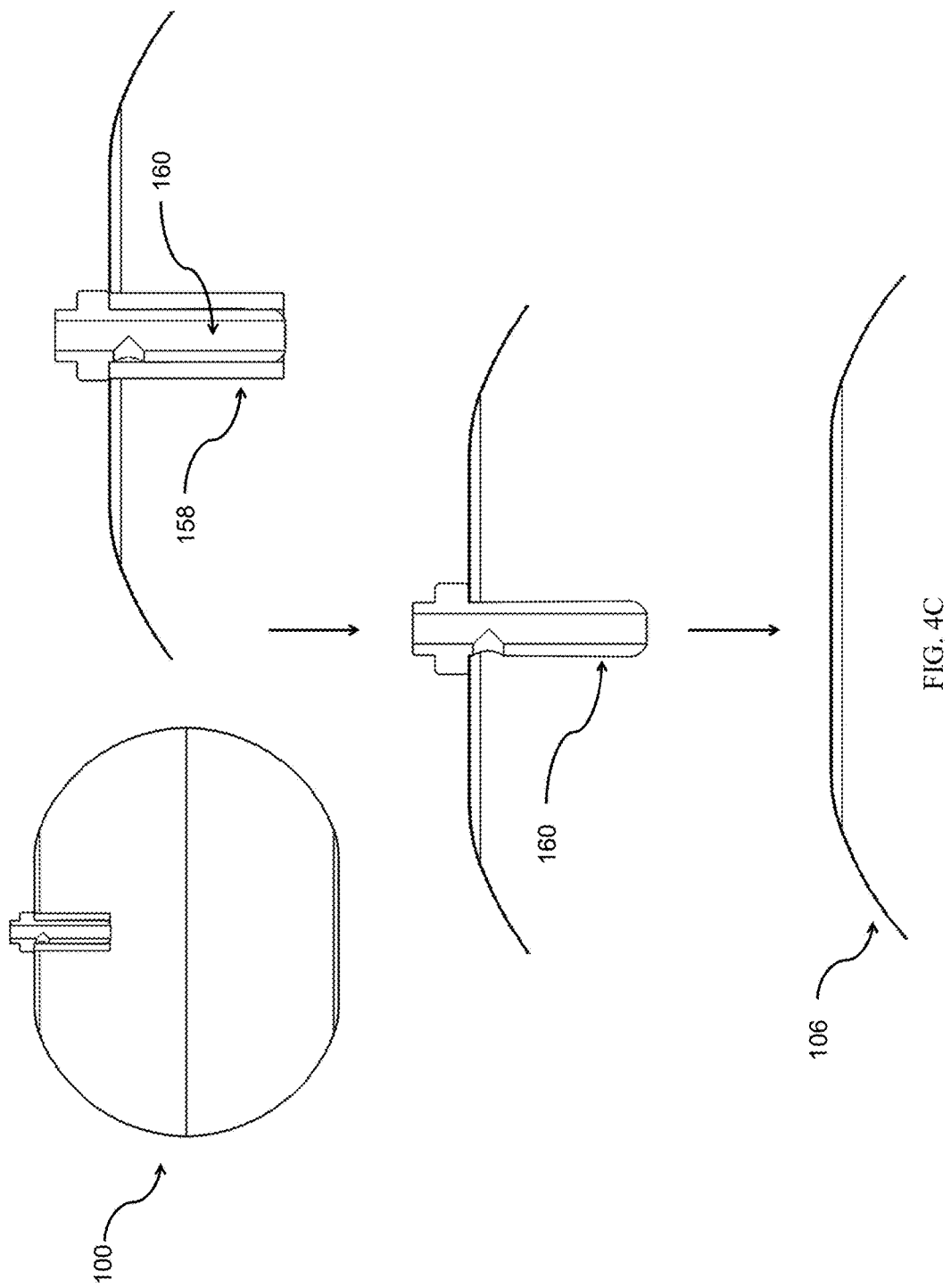
FIG. 4C illustrates an example wherein the band 158 degrades completely, detaching and then releasing the valve 160 from the skin 106.

FIG. 4B illustrates an example of degradable band 158 attached to the skin 106, the expansion valve 160 is embedded in the band 158. FIG. 4C illustrates an example wherein the band 158 degrades completely, detaching and then releasing the expansion valve 160 from the skin 106. After the expansion valve is released from the skin the pressurized gas and fluid exit the balloon from the opening or defect in the balloon at the site of the valve.

Figure 4D:
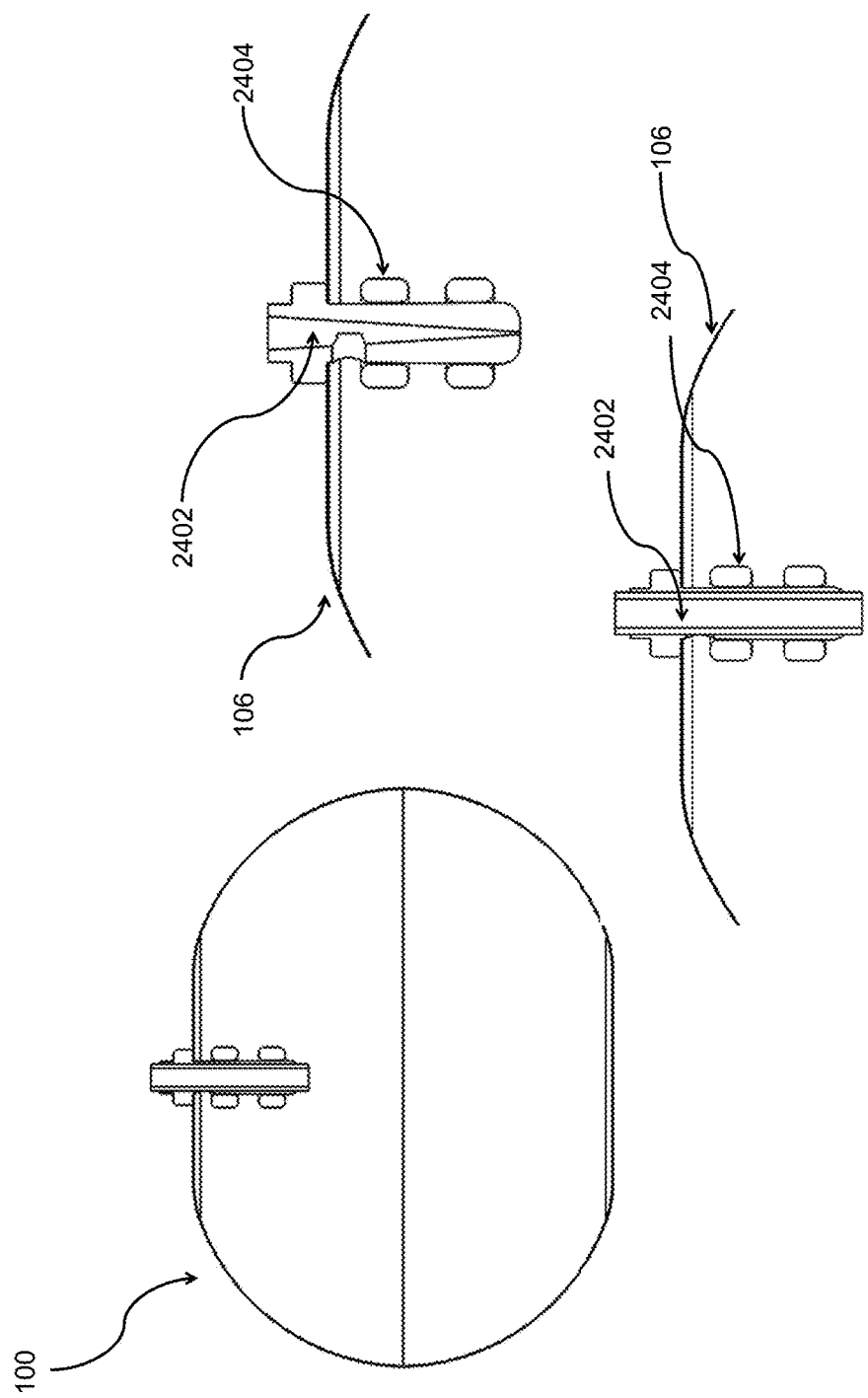
FIG. 4D illustrates an example where the expansion valve 160 is attached to the skin 106, while degradable element 158 is only attached on the outside of valve 160.

FIG. 4D illustrates an example where the expansion valve 160 is attached to the skin 106, while degradable element 158 is only attached on the outside of valve 160. When the band 160 is intact, it provides support to the valve 160, and prevents any internal pressurized gas and fluid from exiting the balloon 100. However, after the band 158 has degraded completely, the valve 160 attachment becomes loose, and the valve is released. This allows any internal pressurized gas and fluid to exit balloon 100.

Figure 4E:
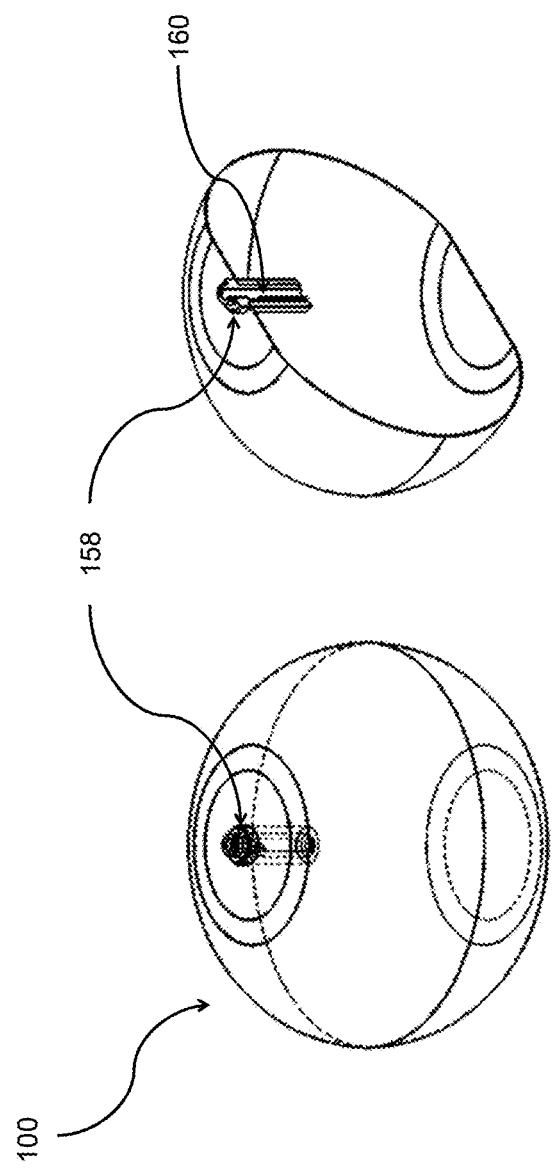
FIG. 4E illustrates a single degradable band integrated with the valve 160, in accordance with at least one embodiment.
Figure 4F:
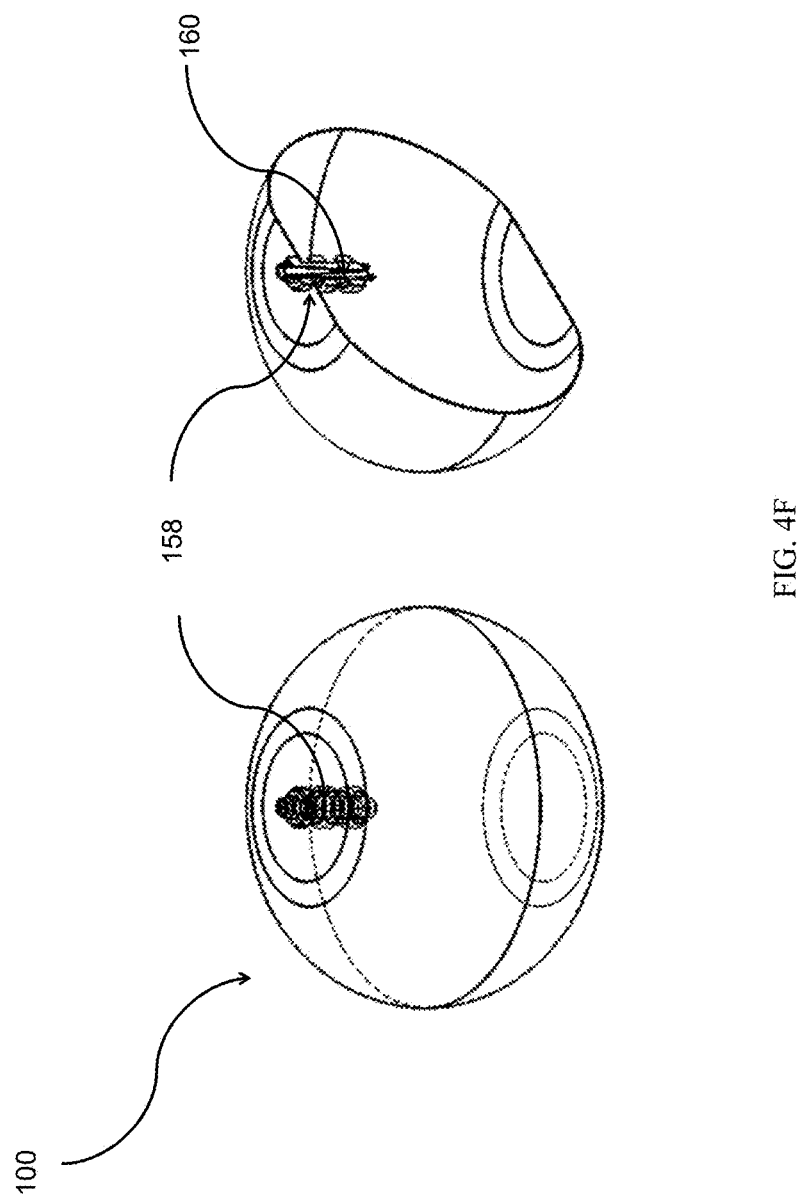
FIG. 4F illustrates multiple bands 158 integrated with the valve, in accordance with at least one embodiment.

Degradable band 158 is at least one band, and can be one or multiple bands. FIG. 4E illustrates a single band integrated in the balloon 100 while FIG. 4F illustrates multiple bands 158 integrated into the balloon 100, in accordance with another embodiment.

Figure 5:
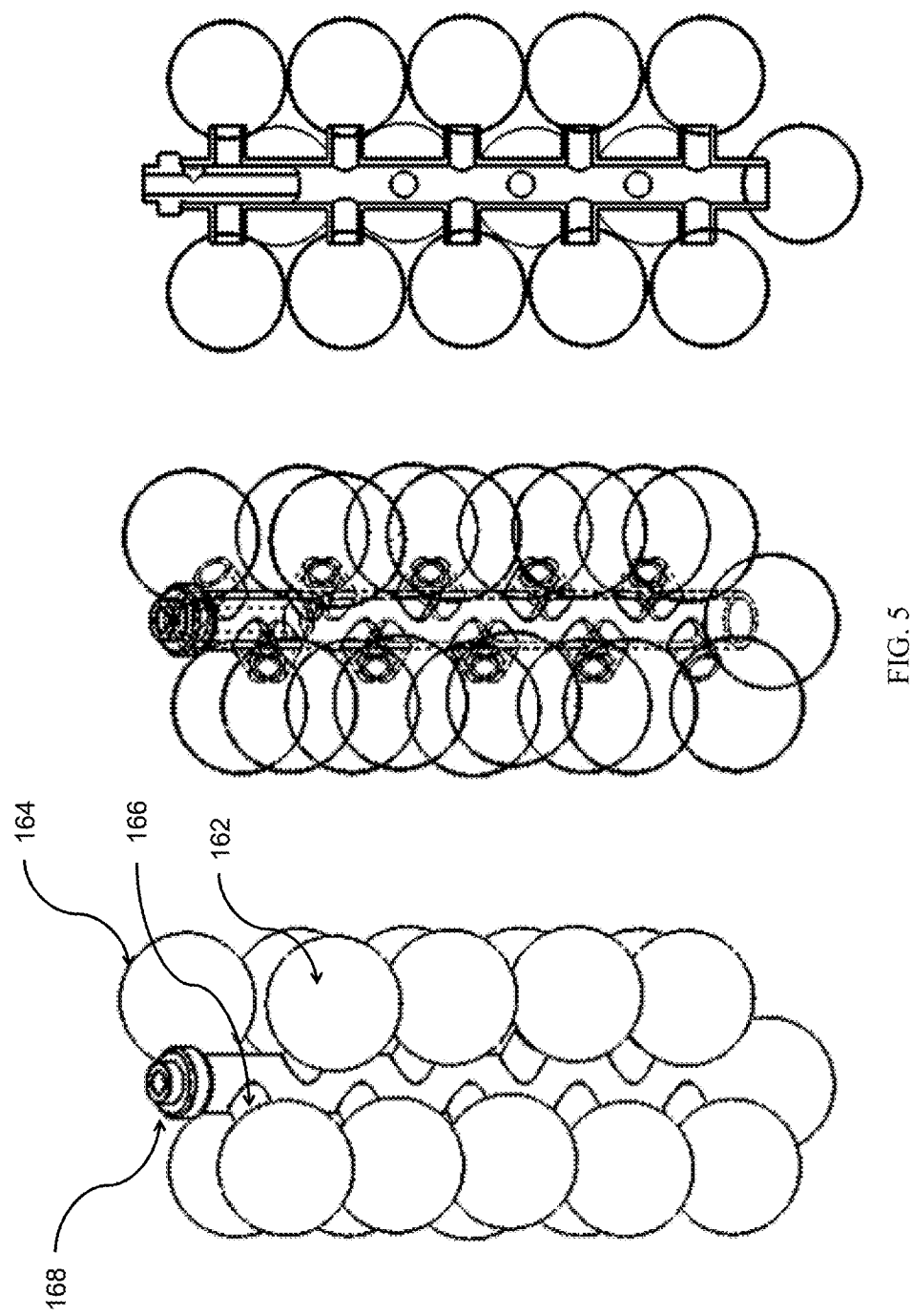
FIG. 5 illustrates an example of multiple small balloons 162 with the degradable skin 164 and or regulators 166 are attached to a catheter 168, described as the grape design.

In another aspect, multiple small balloons 162 with degradable skin 164 or regulators 166 are attached to a catheter 168. This configuration can be described as the "grape design", and is shown in FIG. 5. The advantage of this "grape" design is that each balloon 162 can be made small enough to more easily pass through the gastrointestinal tract. The balloon deflation, along with degradation and disintegration of the balloon, components eventually causes this device to break into smaller parts. The disintegrated smaller parts pass through the intestine into the toilet with peristalsis.

Figure 6:
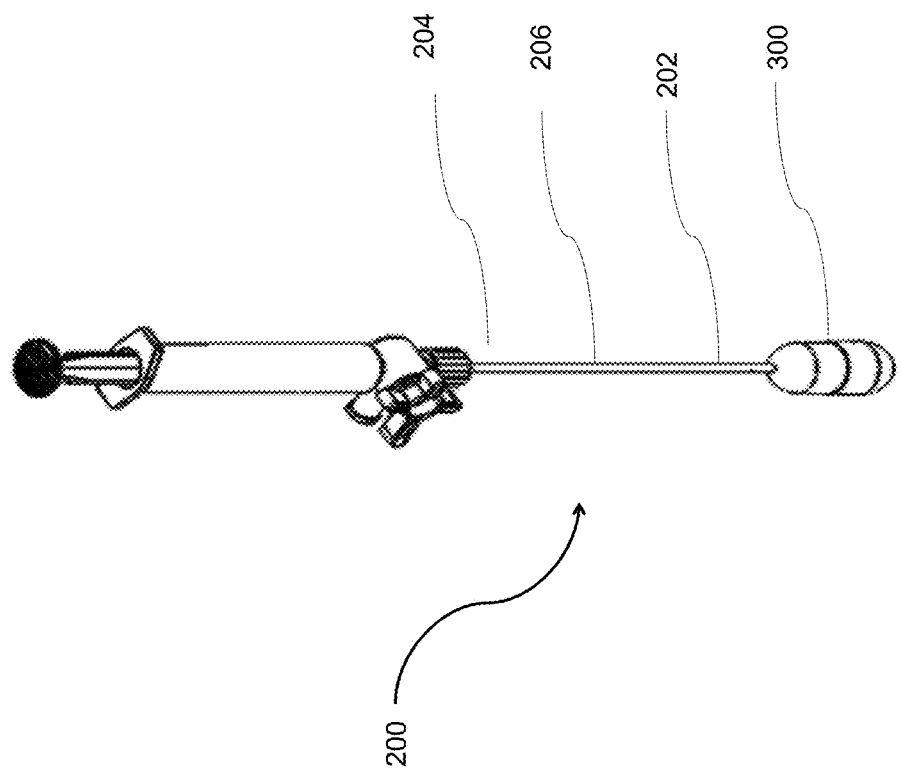
FIG. 6 illustrates a perspective view of the intermedium catheter 200, in accordance with at least one embodiment.

The balloon 100 is often temporarily attached to an intermedium catheter 200. FIG. 6 illustrates a perspective view of the intermedium catheter 200, in accordance with at least one embodiment. The intermedium catheter 200 will typically have a proximal end 204, a medial portion 206 and a distal end 202. This catheter is typically is a hollow tubular thin structure which facilitates placement and then the expansion of the balloon 100.

FIG. 7A illustrates a schematic view of the expansion pin 210 with or without side holes 208, in accordance with at least one embodiment. The distal end of the expansion pin 210 can be either in rounded shape or a tapered shape. The expansion pin 210 can include a plurality of side hole(s) 208 to allow the injected fluid to fill up the balloon 100. The basic side hole 208 will be singular or one-sided (e.g. may only be on one side of the pin). In an embodiment, the expansion pin 210 may include a two-sided configuration (holes on both sides of the pin). In an embodiment, the expansion pin 210 comprises a plurality of parallel holes 208 on one-sided or two-sided. In an embodiment, the expansion pin contains a zig-zag hole configuration on both sides as well.

The outer hollow expansion valve portion of the regulator 104, towards the exterior of the balloon 100, further comprises an opening 128 to accommodate a hollow expansion pin 210. Here the expansion pin 210 is configured to fit inside the opening 128. This places the expansion valve in the first open mode, thus permitting passage of any fluid or gas into the balloon 100 from the distal end of the intermedium catheter 200. FIG. 7B, on the left side, illustrates the regulator 104 comprising opening 128 in the expansion valve, while on the right side FIG. 7B shows a hollow expansion pin 210 filling this opening. The expansion pin 210 can be detachably attached to the regulator 104 as illustrated in FIG. 7C in accordance with at least one embodiment.

The distal end of the intermedium catheter 200 is attached to the hollow expansion pin 210 which is further connected to the opening 128 in the first open mode and thus configured so that when intermedium catheter 200 is attached to opening 128, any outside pressurized gas and fluid is delivered to balloon 100 through the hollow expansion pin 210. The intermedium catheter 200, expansion pin 210 and opening 128 can be further configured so that when expansion pin is at least partially withdrawn from opening 128, the expansion valve portion operates in the second closed mode, thus preventing passage of any fluid or gas out of balloon 100.

In an embodiment, at least a portion of a proximal end of opening 128 can be exterior to the balloon 100, and can be detachably connected to distal end of intermedium catheter 200; and the timing valve portion is attached to this expansion valve portion, and at least a portion of a distal end of the timing valve portion is located on an interior of the balloon 100.

Figure 8A:
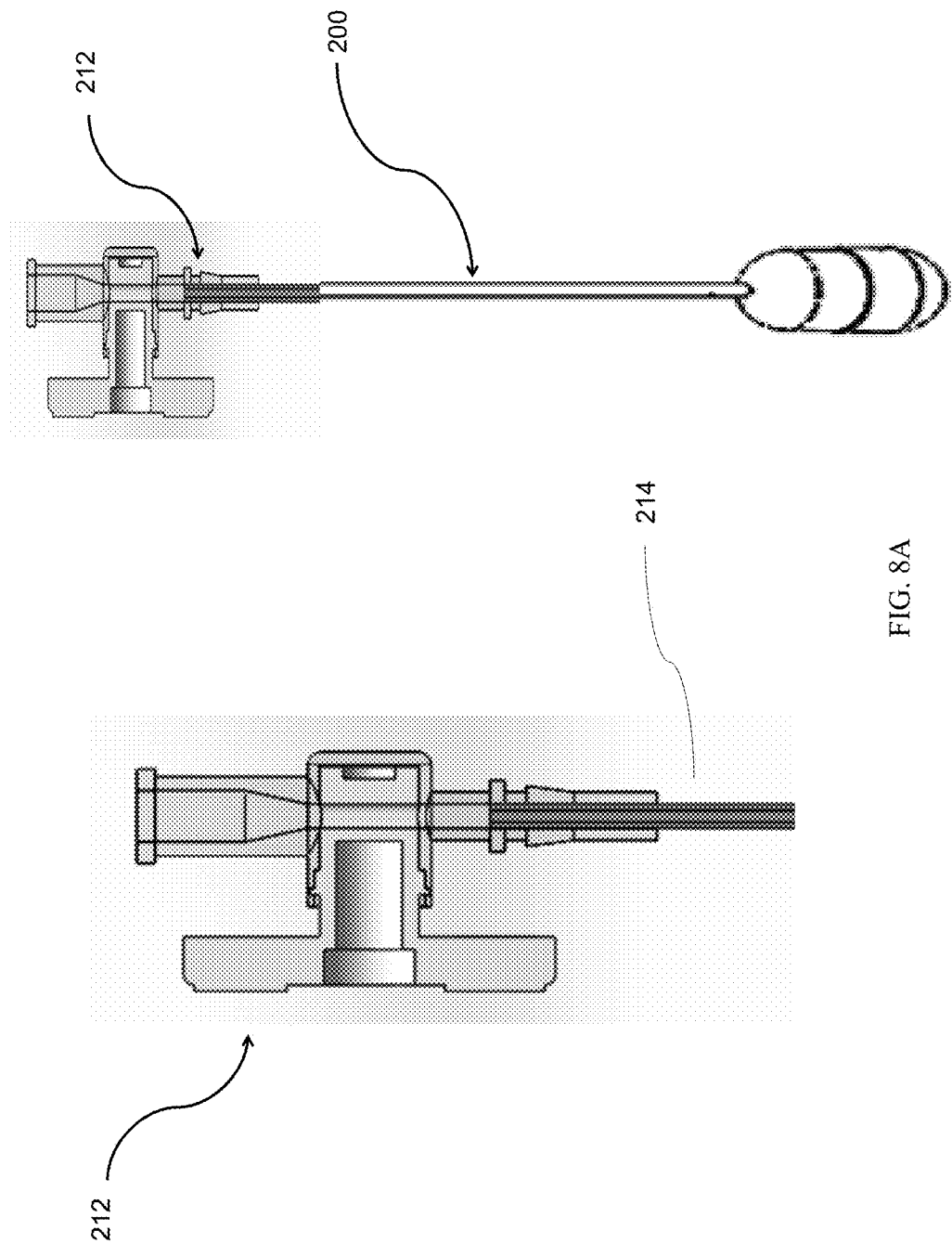
FIG. 8A illustrates a perspective view of the stopcock 212 and its bonding region 214 configured with the proximal end of the intermedium catheter 200, in accordance with at least one embodiment.
Figure 8B:
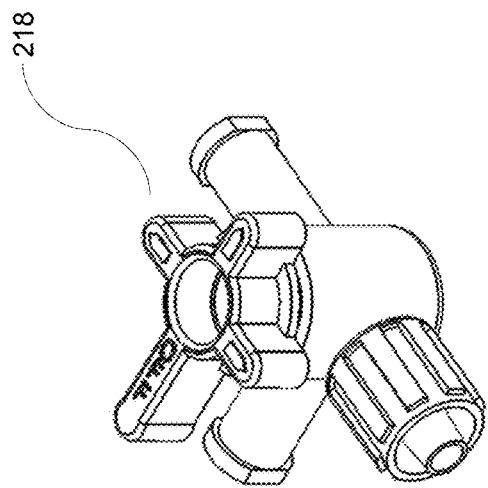
FIG. 8B illustrates a perspective view of the two-way and a three-way stopcock.
Figure 8B:
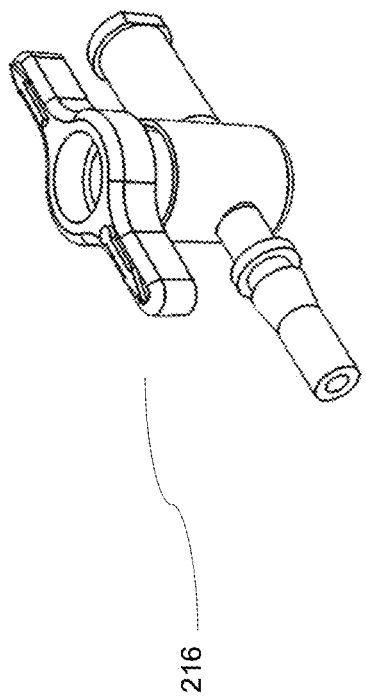

FIG. 8A also illustrates a perspective view of a stopcock 212 and its bonding region 214, in accordance with at least one embodiment. In some embodiments, a three-way stopcock 900 is configured with the proximal end of the intermedium catheter 200 as shown in FIG. 8A. The three-way stopcock 212 allows the medical practitioner/doctor to connect the various accessories such as syringes, adapters etc. to the intermedium catheter 200. Further, the three-way stopcock enables the doctor to insert accessories such as guidewires, small catheters, etc. to the intermedium catheter. FIG. 8B illustrates a perspective view of the various types 216, and 218 of the stopcock. In an embodiment, a different kind of stopcock such as two-way, four-way stopcock can also be utilized to configure with the intermedium catheter. The proximal end of the intermedium catheter remains outside the patient' mouth. The syringes can also be attached to the stopcock through luer locks, such as luer locks governed by ISO 594-1/2 standard. Further, the intermedium catheter can be directly attached to the stopcocks or through an adaptor (proximal end compliance to the ISO 594-1/2 standard, and distal end compliance to the catheter diameter).

Figure 8C:
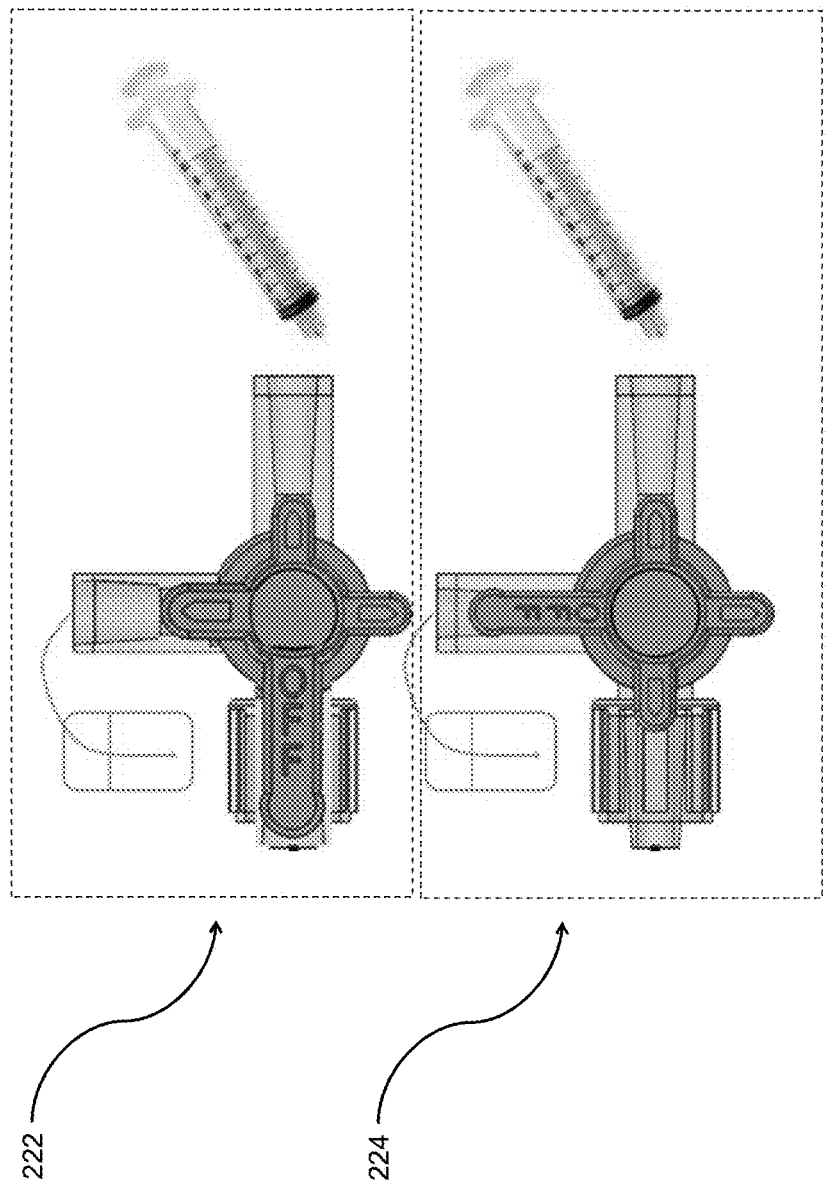
FIG. 8C illustrates an exemplary view of the balloon expansion procedures 222 and 224 through the proximal end of the intermedium catheter 200, in accordance with at least one embodiment.

FIG. 8C illustrates an exemplary view of the balloon expansion procedures 222 and 224 through the proximal end of the intermedium catheter, in accordance with at least one embodiment. In the expansion procedure 222, the medical practitioner turns OFF the path that bonds to the intermedium catheter and withdraws the syringe proximally to draw liquid into the beaker. In the delivery procedure 224, the medical practitioner turns OFF the path that connects to the beaker and pushes the syringe distally. Then the liquid fills the intermedium catheter as well as the balloon 100 in further distance. The medical practitioner repeats the procedures 222 and 224 subsequently until the balloon on 100 expanded entirely with the intended volume.

The medial portion of the intermedium catheter 200 has a length chosen to be longer than the length of the patient's upper gastrointestinal tract (mouth to the distal end of the stomach). This medial portion can be made of polymeric or metallic materials. The distal end of the intermedium catheter 200 is attached to the expansion valve portion of the regulator through the expansion pin. The expansion pin inflates the balloon 100 with gas or fluid. The attachment of the expansion pin with the intermedium catheter can be accomplished through heat adhesion or adhesives (light cure, cyanoacrylate or solvent based). In an embodiment, the expansion pin is a modified extension of the distal end of the intermedium catheter.

It is often useful to enclose the balloon in a protective capsule to facilitate placement of the balloon onto the patient's stomach. FIG. 9A illustrates a perspective view of such a capsule 300, in accordance with at least one embodiment. The capsule 300 can include a top unit 302, and bottom unit 304. The top unit 302 of and the bottom unit 304 of the capsule 300 can be a separate two units or a single unit depending on the process. The top unit 302 of the capsule 300 can be longer than the bottom unit 304 of the capsule 300 i.e. about ⅔ of the overall length of the capsule 300. The capsule units 302 and 304 can be degradable. In an embodiment, the top unit 302 is non-degradable, rigid, but smooth material, configured to cover the expansion pin and to protect the patient's esophagus region from the potential trauma that can be caused by scraping of the expansion pin against the esophagus during the retrieval process.

The balloon 100, typically made from a thinner and lighter material, and is generally disposed within the capsule 300 in a contracted state to facilitate oral ingestion without difficulty and safely. The capsule 300 is typically configured to traverse the patient's esophagus (e.g. from the patient's mouth to the stomach), and then to release balloon 100 into the patient's stomach 100 upon application of either mechanical force or chemical action of stomach digestive fluids. In some embodiments, capsule 300 can comprise a vegetarian material or gelatin to allow for rapid degradation in the stomach and release of the balloon 100.

In some embodiments, a folding mechanism is required to ensure the fitting of the balloon 100 in the capsule 300.

Figure 9D:
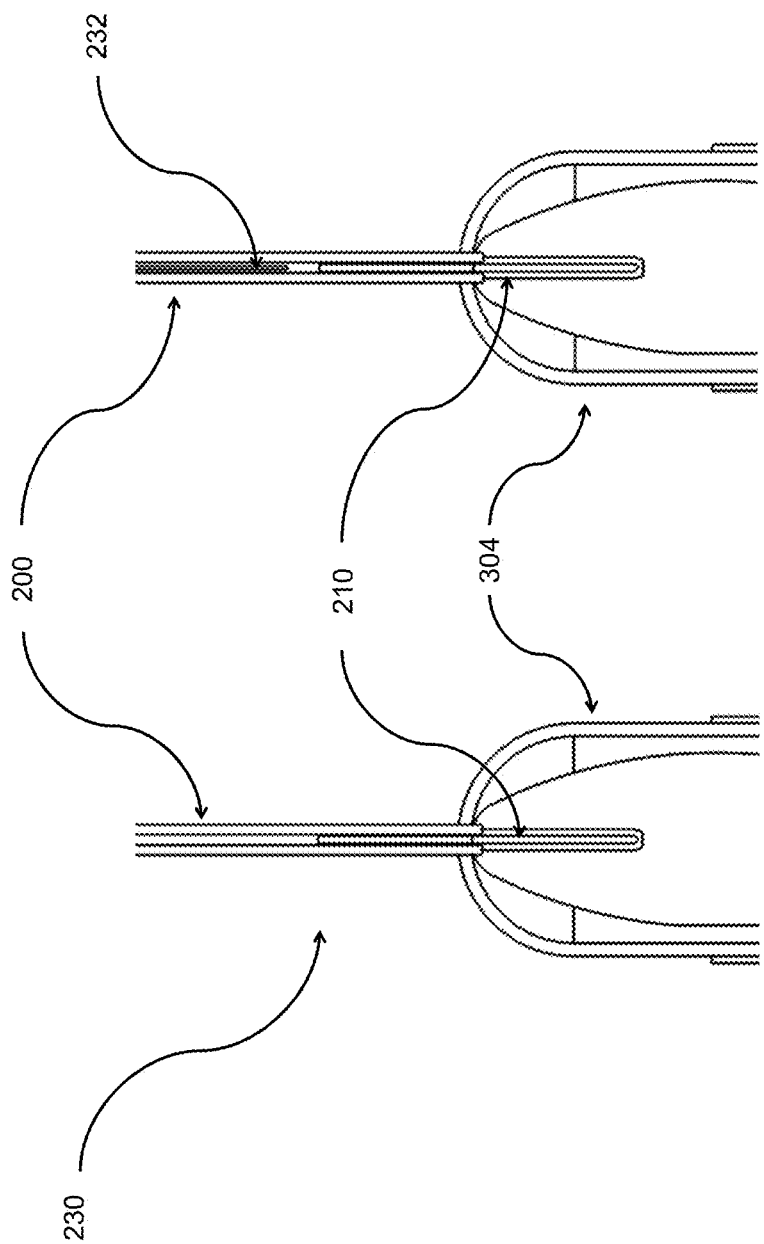
FIG. 9D illustrates the capsule sub-system without the accessories 230 and the capsule sub-system with the accessories 232.

FIG. 9B illustrate a perspective view of the capsule sub-system, in accordance with at least one embodiment. The top unit 302 of the capsule 300 receives the expansion pin 210 connected to intermedium catheter 200 on the distal end, and attached to the contracted balloon 100 through the regulator 104 on the proximal end. The bottom unit 304 mainly contains the folded contracted balloon 100. The capsule 300 may optionally disintegrate upon contact with the patient's gastrointestinal environment or upon expansion of the balloon 100, or both. FIG. 9C and FIG. 9D shows the capsule sub-system without the accessories 230, and the capsule sub-system with the accessories 232. In an embodiment, the accessories 232 may be a simplistic as a guidewire, or as complicated as an imaging system such as an electromagnetic catheter.

In an embodiment, the intermedium catheter along with the expansion pin is permanently attached to the capsule. Upon inflation of the balloon 100, the capsule may be retrieved from the patient's stomach along with the intermedium catheter and expansion pin. In an alternative embodiment, the intermedium catheter is semi-permanently attached to the capsule. The capsule detaches from the intermedium catheter upon expansion of the balloon 100 and remains in the stomach. In another alternative embodiment, the capsule 300 is biodegradable and dissolves in the stomach. In another alternative embodiment, the capsule 300 is non-biodegradable and able to pass through the intestine and pass out in the toilet.

Figure 10A:
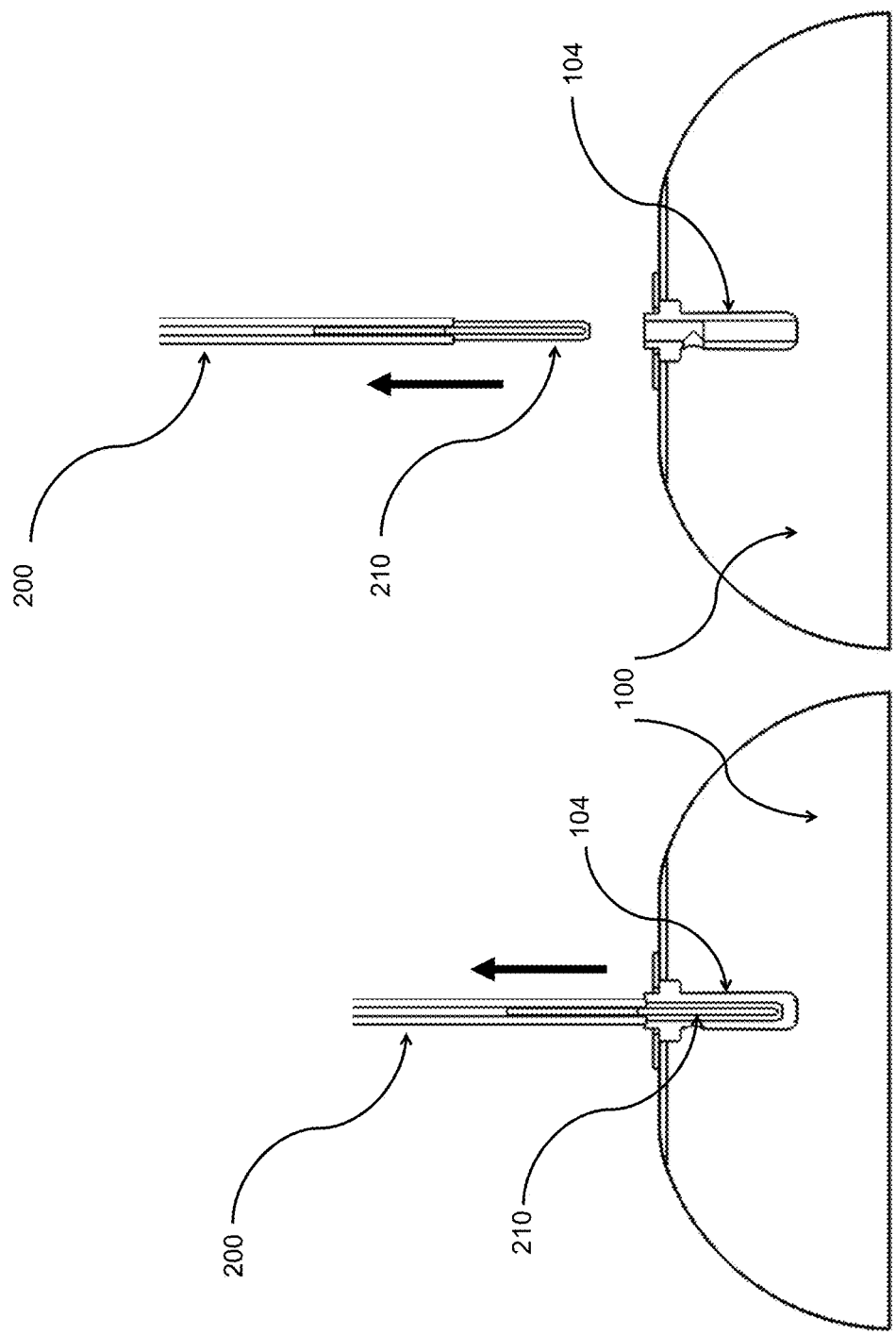
FIG. 10A illustrates a perspective view showing detachment of the expansion pin 210 and the intermedium catheter 200 from the balloon 100.

The intermedium catheter 200 can be further configured to apply mechanical force on the regulator 104 to detach the intermedium catheter from the balloon 100. FIG. 10A illustrates a perspective view showing detachment of the expansion pin 210 and the intermedium catheter 200 from the balloon 100. When the intermedium catheter 200 is pulled on the proximal end away from the patient body, this force is transmitted to the expansion pin 210 to detach it from the regulator 104. This force is a reverse vector force, which is further facilitated by inward pressure from the expanded balloon and hydrostatic pressure of the liquid within the balloon 100.

Here, pulling off the intermedium catheter brings the balloon proximally in the stomach against the gastroesophageal junction. This junction provides a counterforce to detach the expansion pin from the regulator 104. Detachment of the expansion pin from the regulator 104 results in separation of the intermedium catheter from the balloon 100 resulting placement of the balloon in the stomach. After placement of balloon 100 in the stomach, the expansion pin and intermedium catheter are further pulled out and retrieved out the patient's mouth.

Figure 10B:
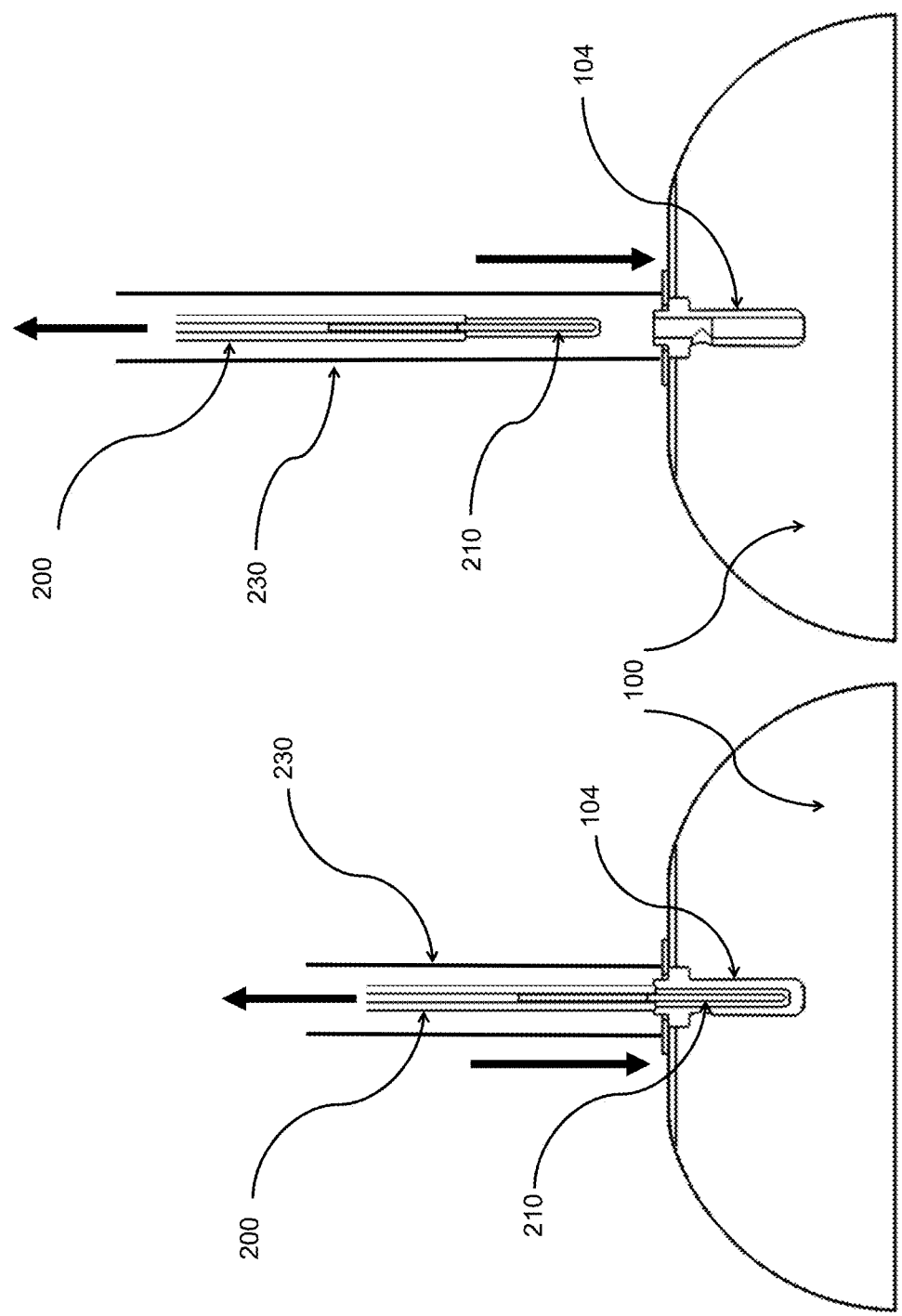
FIG. 10B illustrates an example of the intermedium catheter 200 with outer sheath 230 configured to apply a counter force towards the balloon 100 resulting in detachment of expansion pin 210 form the regulator 104.

In another and potentially preferable embodiment, intermedium catheter 200 can have a freely moveable outer sheath 230 configured to apply a counter force towards the balloon 100 while pulling the intermedium catheter 200 away from the patient body. This creates a mechanical force on the regulator 104 to detach it from the expansion pin 210, resulting in detachment of the balloon 100 from the intermedium catheter 200. FIG. 10B illustrates an example of the intermedium catheter 200 with outer sheath 230 configured to apply a counter force towards the balloon 100, resulting in detachment of expansion pin 210 from the regulator 104.

The benefit of this alternative design and method for deployment is that it does not use the patient's gastroesophageal junction 232 to provide counterforce while pulling out the intermedium catheter. This alternative design and method therefore helps avoid any injury to the patient's gastroesophageal junction 232 (FIG. 8C).

Figure 10C:
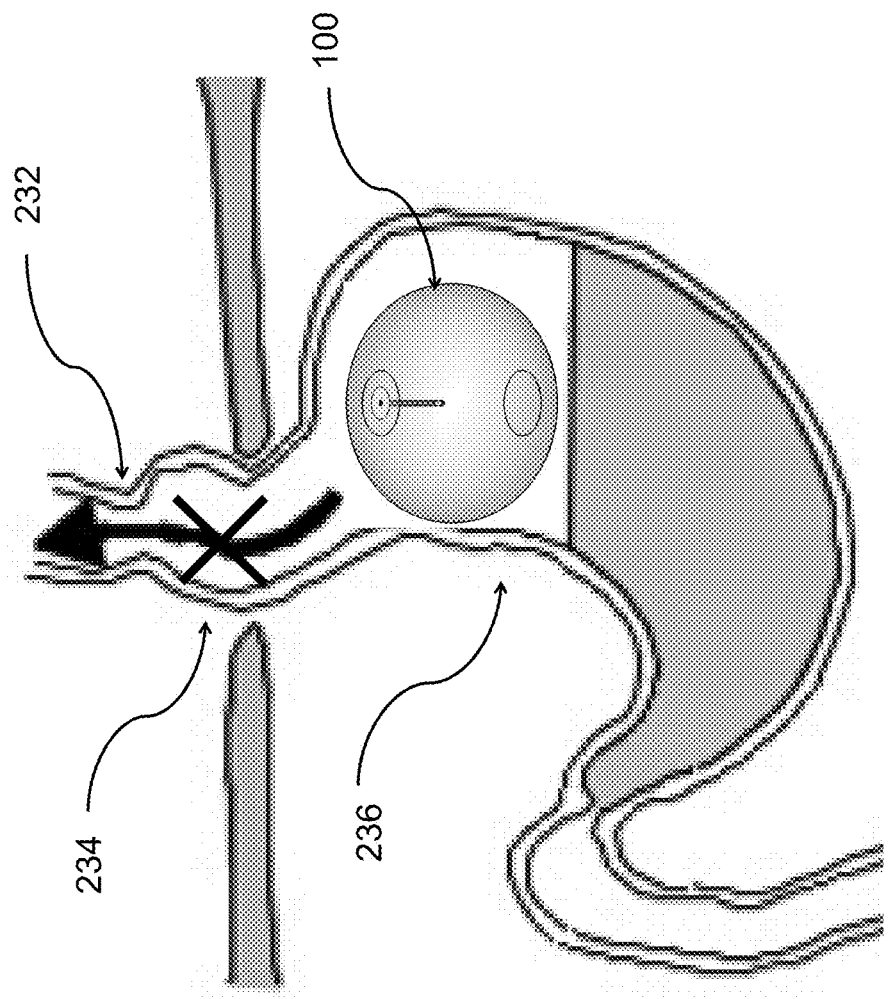
FIG. 10C illustrates a method for deployment of balloon 100 in a patient with a hiatal hernia 234.

This method is also beneficial for patients with hiatal hernia 234 as illustrated in FIG. 10C. In FIG. 10C, in a patient with hiatal hernia 234, the upper part of the patient's stomach 236 migrates in the patient's chest and the gastroesophageal junction. The status of the patient's gastroesophageal junction 232 can be weak. In this situation, pulling the intermedium catheter 700 against the gastroesophageal junction (232) to detach the balloon can lead to the deployment of balloon 100 in the hiatal hernia 234 and cause complications. By contrast, by using the freely moveable sheath 230 to detach the balloon 100, the risk of pulling the balloon 100 with the intermedium catheter 200 proximally all the way close to the hiatal hernia 234 and gastroesophageal junction 232 is reduced. Instead, balloon 100 can be detached from the intermedium catheter 200 in the stomach area 236 distal to the hiatal hernia 234, by using the counterforce exerted by the sheath 230 instead of the gastroesophageal junction 232.

In another embodiment, the intermedium catheter can be attached to the regulator 104 or balloon 100 with a suture which can be untied or detached from outside by pulling off the intermedium catheter or sheath.

Verifying Placement:

Generally balloon 100 should only be expanded in the stomach; expansion in any other part of the gastrointestinal system can lead to perforation and additional complications. Therefore it is essential to confirm the balloon's location and placement in the stomach. Once the capsule 300 is degraded or separated, the placement of the balloon in the stomach, can be verified by traditional methods such as direct vision under endoscopy, or imaging techniques such as X-ray, fluoroscopy, or ultrasound, etc. To facilitate this, in some embodiments, part of the balloon and or the regulator of the present invention are made of radiopaque material which can be detected by X-ray imaging methods, and can be used to confirm placement in the stomach or any part of the gastrointestinal system.

Figure 11A:
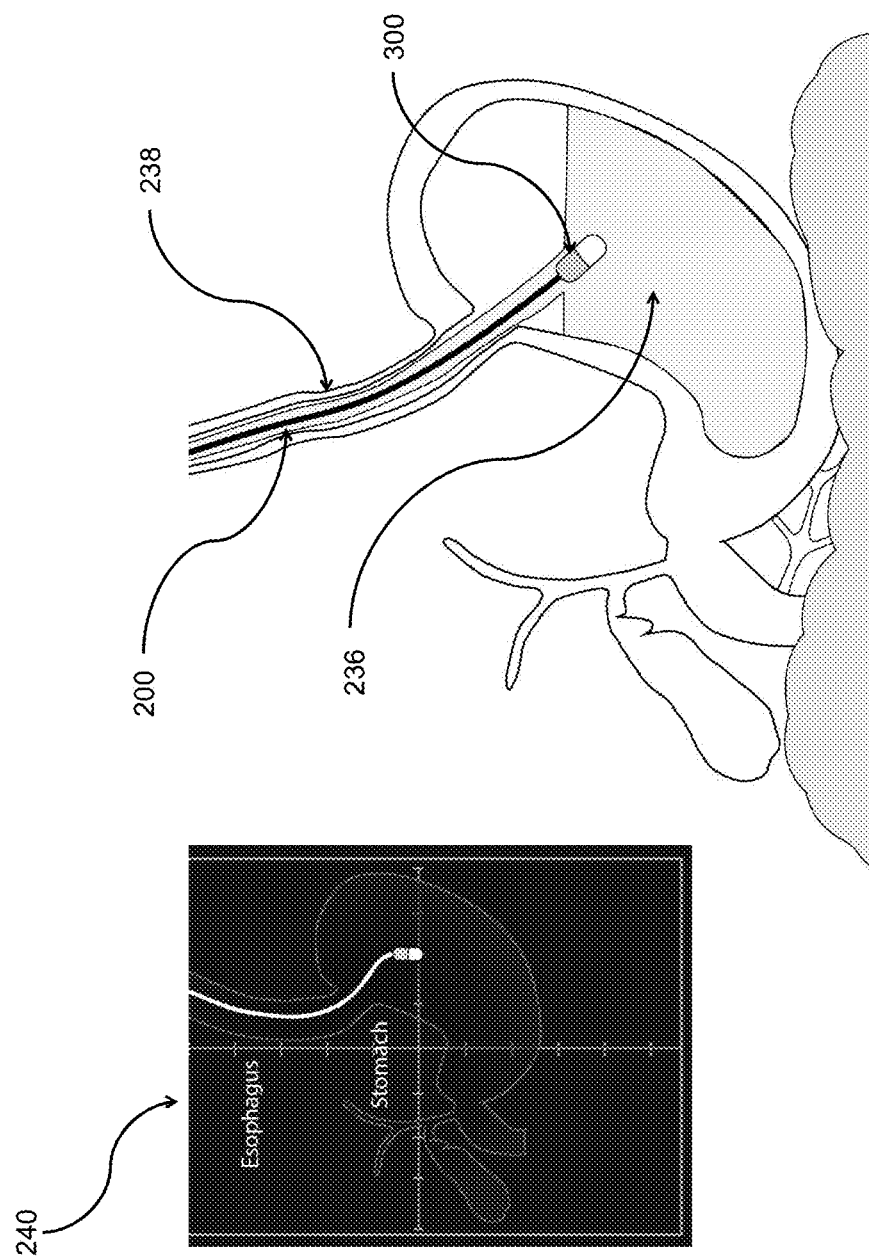
FIG. 11A illustrates an exemplary view of the electromagnetic tracking and placement of the device in the patient's stomach 236, in accordance with at least one embodiment.

In some embodiments, the present device may have various tracking mechanisms, such as an electromagnetic tracking system, to track the pathway and location of the device in the gastrointestinal system. FIG. 11A illustrates an exemplary view of one such electromagnetic tracking system, showing tracking and placement of the device in the patients stomach 236, in accordance with at least one embodiment. The capsule 300 and the intermedium catheter 200 is configured to traverse an esophagus 238 of a patient from a mouth of a patient to a stomach 236 of a patient, and then to release balloon 100 into the stomach. The passage of the intermedium catheter 200 and capsule 300 are shown on an external recording unit 240, and the final placement and confirmation of the capsule in the stomach are recorded.

Figure 11B:
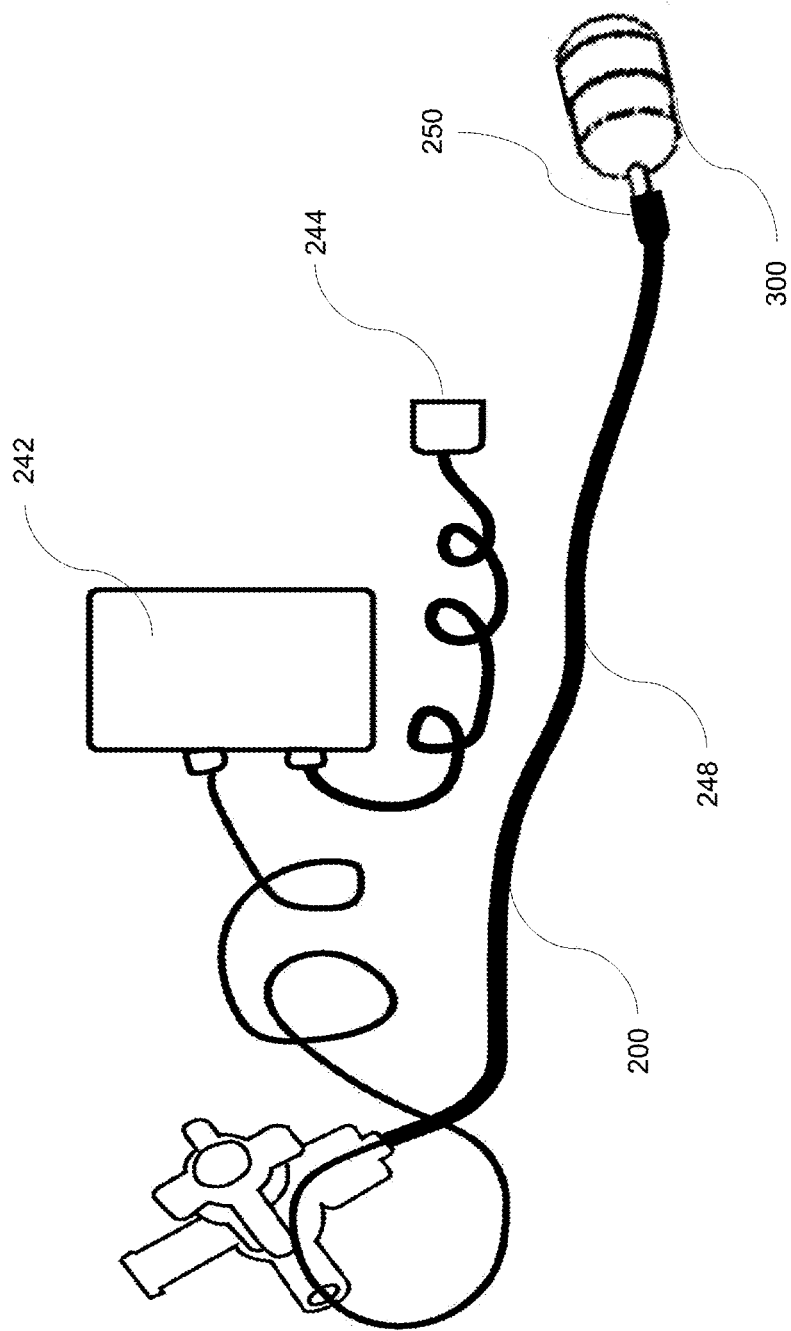
FIG. 11B illustrates an example of the electromagnetic system consists of an electromagnetic external unit with or without a recorder and screen 242, transmitters 244 which emits an electromagnetic field, single or multiple magnets or sensors 250 coupled to an external electromagnetic unit 242 by a connector or wire 248.

FIG. 11B illustrates an example of such an electromagnetic tracking system, here comprising an electromagnetic external unit (with or without a recorder) and screen 242, transmitters 244 which emit an electromagnetic field, and/or single or multiple magnets or sensors 250 coupled to an external electromagnetic unit 242 by a connector or wire 248. The sensor 250 and the wire 248 will typically have a diameter less than the intermedium catheter 200 and can be located inside the catheter. The sensor 250 can be attached to the wire 248, which emerges from the proximal end of the intermedium catheter 700 and three-way stopcock, and can be configured to connect with the external unit. This wire can be configured to transmit electromagnetic signals from the sensor 250 to the external unit 242 (FIG. 11B).

The sensors 250 can be configured to track the movement of the intermedium catheter and capsule by monitoring the position and orientation in the patient's three-dimensional gastrointestinal space. These electromagnetic sensors 250 can be located in various locations, such as within the capsule 300 or regulator 104, or balloon 100 or the intermedium catheter 200, and can provide real-time tracking and feedback of the location and advancement of the system. FIG. 12A illustrates an exemplary view of capsule 300 and the intermedium catheter 200 with sensors 250.

Figure 12B:
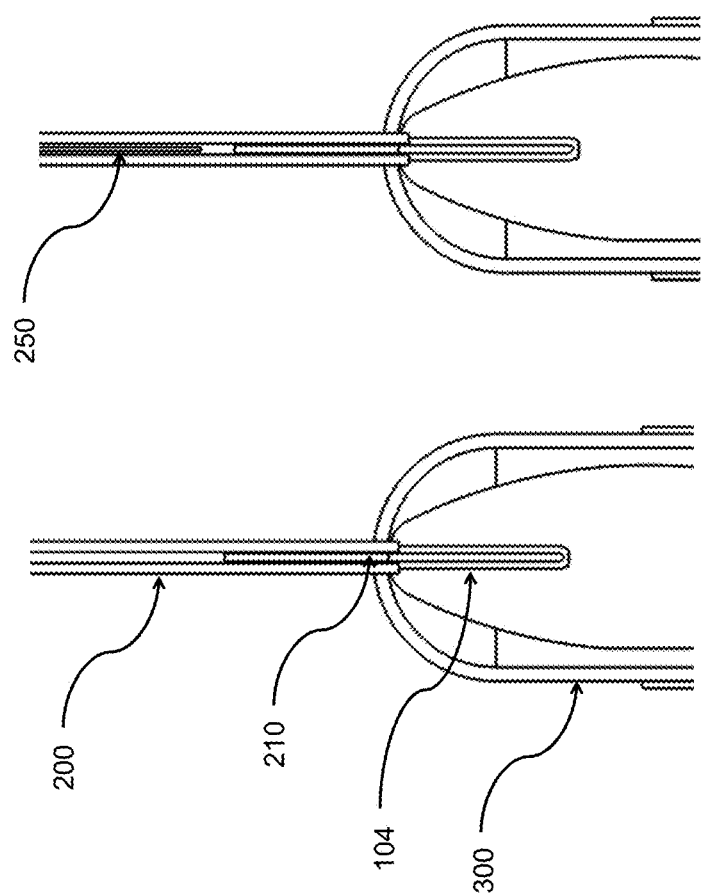
FIG. 12B illustrates an exemplary view of the distal end of the intermedium catheter 200 fitted with and without an electromagnetic system sensor 250.

FIG. 12B illustrates an exemplary view of the distal end of the intermedium catheter 200 fitted with (right side) and without (left side) an electromagnetic system sensor 250. FIG. 12C illustrates multiple sensors 250 on the distal and or medial intermedium catheter 200 and a coupled guiding system 260 outside the patient's body to enable the user to guide the capsule 300 and intermedium catheter 200 advancement within the patient's GI tract. The electromagnetic sensors 250 can alternatively or additionally be located within the regulator 104 or balloon 100, and can also be configured to provide real-time feedback on the balloon's 100 expansion and volume.

The volume of the expanded balloon 100 can also be estimated by alternative methods, such as measuring the amount of gas or fluid delivered to the balloon 100, or by measuring the pressure inside the balloon. The passage of the regulator and attached components through the patient can also be tracked via an electromagnetic sensor in the regulator or balloon. Since one of the possible complications of gastric balloon methods is potential bowel obstruction and perforation, tracking of the balloon can detect the passage of the balloon's through the patient's small bowel (small intestines) is important in order to detect or predict obstruction, and prevent perforation.

In some embodiments, one or more other types of sensors such as pH, pressure, or temperature sensors can also be used to track the device and confirm placement. Here one or more such sensors and types of sensors can be used. These sensors can be wired or wirelessly connected to recorders depending on the function and needs. These sensors can be located at the distal end or medial region of the intermedium catheter. These sensors can track at 360 degrees or at least 180 degrees circumferentially.

Figure 12D:
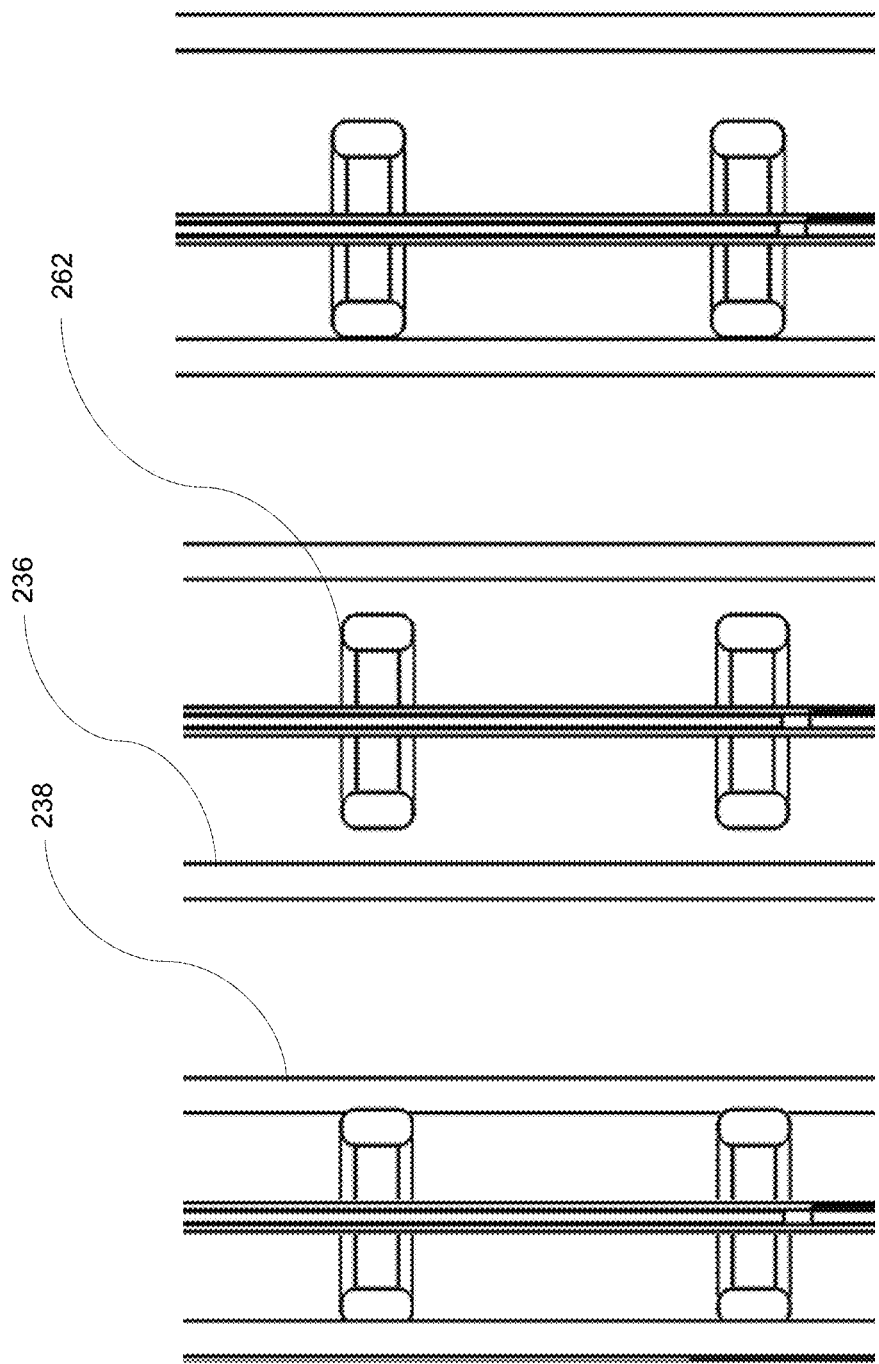
FIG. 12D illustrates an exemplary view of the proximity or pressure sensors 262 in the lumen of the esophagus 238 or the stomach 236.

Proximity sensors can be used to help track placement as well. The esophagus is a narrow part (smaller diameter) of the gastrointestinal tract, will have high pressure or a closer distance to any such sensors. By contrast the stomach is a wider open part of the GI tract, with correspondingly lower pressures and larger distances. To help prevent sensor results from being distorted due to detecting only pressure on one side of the sensor, sensors to sense pressure or distances around the sensor (e.g. circularity, 360-degree sensing) can be preferable. Such sensors will still be able to indicate that the device is in the stomach region. FIG. 12D illustrates an exemplary view of the proximity or pressure sensors 262 in the lumen of the patient's esophagus 238 or stomach 236.

Thus, depending upon what sensors are employed, changes in observed sensor temperature can signify ingestion of the device. A sensor observed decrease in pH to baseline stomach pH can indicates that the device has reached the patient's stomach. Sensor observed pressure changes, such as a change from a high pressure observed in the patient's esophagus and gastroesophageal junction, down to a lower pressure observed when the device passes into the larger and lower-pressure stomach region, can indicate that the device has now reached the patient's stomach. Further, an observed increase in pH from the low acidic pH in the stomach region, to a higher pH often found in the patient's small intestine (small bowel) can suggests that the device has passed from the patient's stomach to the patient's small bowel.

Figure 12E:
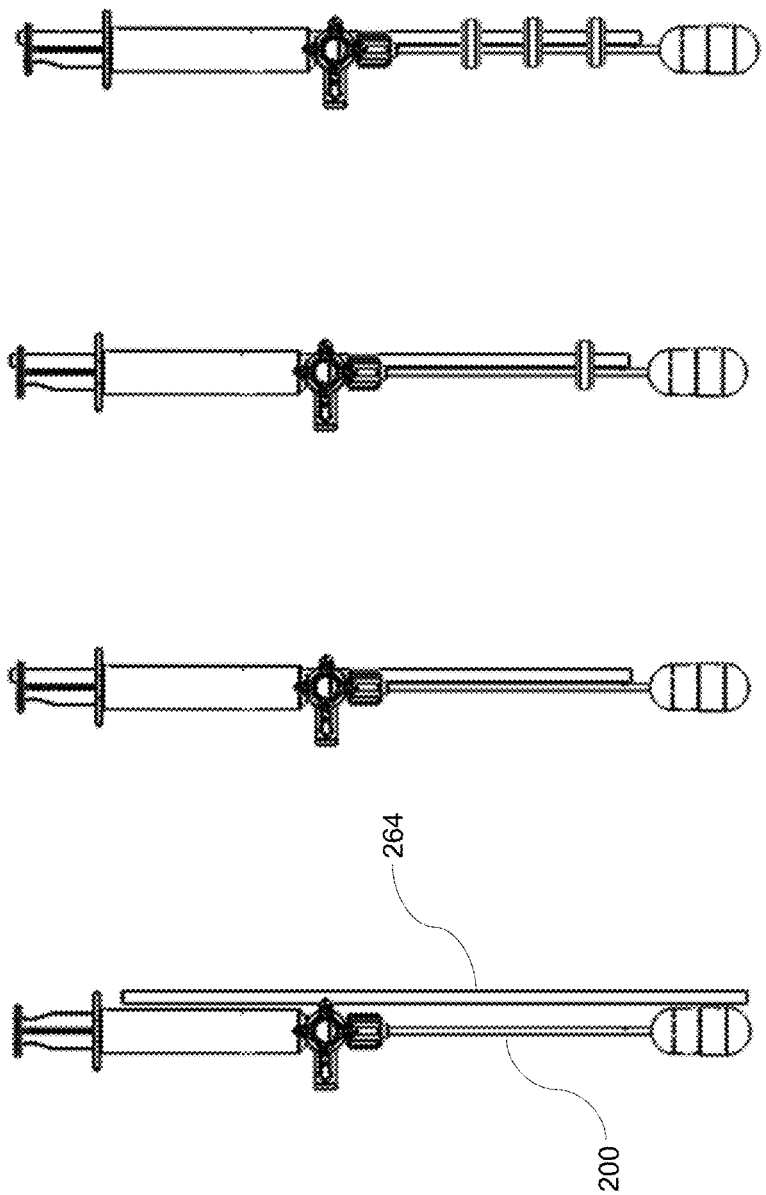
FIG. 12E illustrates an example of thin endoscopes 264 attached to the intermedium catheter 200.

In other embodiments, one or more small cameras, such as capsule endoscopy or thin endoscope 264 cameras, can be attached to the intermedium catheter 200 or the capsule to track and confirm placement, as shown in FIG. 12E. Direct visualization with such camera(s) can help confirm location. For example, endoscopy cameras can observe the mucosal surface appearance of the various regions, and these can be easily identified by a trained professional. The camera(s) may be connected with a thin wire to various external monitors, thus allowing the physician or technician user to better visualize placement.

Cameras in other locations, such as on the wall intermedium catheter, or the surface of the capsule with the connecting wire inside the intermedium catheter, can also be used. Cameras or camera fittings or sensor fittings may also be configured as a separate system attached to the intermedium catheter outside the patient. The attachment method for camera or sensors can comprise mechanical techniques such adhesives, an additional locking mechanism or even wrapping methods such as heat shrink, rubber band, etc., shown in FIG. 12E.

As previously discussed, once the conveyance in the stomach is confirmed, the balloon 100 can be inflated with the gas (such as air, nitrogen) or fluid (such as water or normal saline). The gas or fluid can be delivered to the balloon 100 using the port of the intermedium catheter. In some embodiments, the volume of the inflated balloon 100 is between 400 ml to 700 ml.

Through such sensor mechanisms located within the device, are often mostly just used to monitor correct device placement, in alternative embodiments, the device and methods described herein can also be used for a primary purpose of measuring patient status such as gastrointestinal pH, temperature, pressures and the like, as well. Thus although in this disclosure, use of such sensors for device placement is emphasized, use for such sensors and methods for purely diagnostic purposes is not disclaimed.

Returning to the sensor discussion, in some embodiments, sensors can be placed in the balloon 100; these sensors can measure data like pressure, motility, and pH for a predetermined duration in the stomach and then pass through the intestine. This data can be used for various diagnostic purposes, such a studying motility for patients with gastroparesis, pH in patients with peptic ulcers or gastroesophageal reflux changes, and the like.

The device and method described herein has the additional advantage that the system's timing capability allows the time of diagnostic or therapeutic duration to be controlled easily. In one example the device and the system can be used for a more extended period of data collection for more accurate assessment of motility and pH changes, relative to the prior art capsule devices which transit through the stomach into the small bowel. This can allow for more detailed providing one-time motility and pH measurements.

For short term observerations, such as for purely diagnostic applications, the duration for which the balloon resides in the stomach can be reduced to a short time, such as hours, by decreasing the length of the degradable element or retainer in the timing valve portion of the regulator. After the predetermined diagnostic duration, this device can naturally pass into the intestine, as similar to other prior art capsule devices without such timing regulators.

The device and system described herein can also be used for sustained delivery of drugs, medications, or other therapeutic material. Here, for example, such therapeutic agent or material can be delivered on the skin of the balloon, or can filled within the balloon. The rate and timing of the release of the therapeutic agent from the interior of the balloon in the gastrointestinal tract can be controlled by controlling the degradation of the degradation element within the timing valve of the regulator.

In some embodiments, the devices and methods described herein can also be used for developing other medical devices for gastroenterology, urology and cardiology devices. In some embodiments, the devices and methods described herein may be configured to wirelessly report data to patient carried handheld devices, such as smartphones. These devices may in turn provide software or mobile apps that can optionally wirelessly interface with the various balloon device sensors. Such systems can enable the patient to monitor his/her weight, diet and activity to optimize the benefits of the present balloon device, as well as in some embodiments receive balloon sensor data to help further optimize weight loss progress and/or detect and prevent complications.

Thus, the present invention provides a balloon device 100 which does not require endoscopy for both insertion and removal. The balloon optionally can utilize sensors such as the various electromagnetic sensors described herein, to confirm placement in the stomach and avoid imaging techniques such as potentially harmful X-ray imaging methods.

The present balloon 100 can be quickly (e.g. less than 10 minutes) placed by relevant technicians or doctors.

Further, the current balloon includes a unique timing regulator (e.g. the expansion and timing valves). The timing valve allows the inflated balloon, after the time has expired, to spontaneously contract to a deflated state and subsequently pass outside of the patient's gastrointestinal tract.

The desired therapeutic duration of the balloon can be varied, according to patient's needs, by simple changes in the properties or dimensions of the timing valve. The balloon device disclosed herein provides a complete solution for weight loss, with no additional procedures and/or X-ray imaging required. This increases patient acceptance of these techniques, and decreases overall cost. The present invention also discloses various systems and method to minimize complications.

Further limitations and disadvantages of conventional and traditional approaches will become apparent to one of skill in the art, through comparison of described systems with some aspects of the present disclosure, as outlined in the remainder of the present application and with reference to the drawings. Moreover, the devices, methods, and systems described herein are not limited to treatment of obesity and can even be applied to a diagnostic and therapeutic area outside of obesity.

While the present disclosure has been described with reference to certain embodiments, it will be understood by those skilled in the art that various changes may be made, and equivalents may be substituted without departing from the scope of the present disclosure. Also, many modifications may be made to adapt a particular situation or material to the teachings of the present disclosure without departing from its scope. Therefore, it is intended that the present disclosure not is limited to the particular embodiment disclosed, but that the present disclosure will include all embodiments falling within the scope of the appended claims.

The invention claimed is:

1. A gastrointestinal device comprising:
   a balloon comprising a thin flexible polymeric skin enclosing an interior volume, said balloon capable of transitioning between a contracted state and an expanded state;
   a regulator comprising a combination flow regulator expansion valve and timing valve embedded in said skin and spanning from an interior to an exterior of said balloon, forming an adjustable one-way valve, said combination flow regulator expansion valve and timing valve comprising a flow regulator expansion valve portion comprising a hollow tube with at least one tube opening that opens into the interior of said balloon, an elastic polymeric sheath sealing said at least one tube opening, said hollow tube configured to accommodate a hollow expansion pin with a rounded bottom, said hollow expansion pin configured to transport any of outside pressurized gas and fluid, said elastic polymeric sheath configured to be displaced from said at least one tube opening by any of said outside pressurized gas and fluid, said flow regulator expansion valve portion configured to:
   a) in a first open mode, permit any of outside pressurized gas and fluid to enter said balloon and cause said balloon to transition from said contracted state to said expanded state;
   b) in a second closed mode, prevent any of internal pressurized gas and fluid from using said expansion valve portion to exit said balloon;
   said combination flow regulator expansion valve and timing valve further comprising a timing valve portion comprising a gas and fluid impermeable timing regulator degradable element, said timing valve portion configured to:
   c) while said degradable element is intact, said degradable element prevents any of internal pressurized gas and fluid from using said combination flow regulator expansion valve and timing valve to exit said balloon;
   d) after said degradable element has degraded, allow any of internal pressurized gas and fluid to use said combination flow regulator expansion valve and timing valve to exit said balloon;
   said balloon having expanded state dimensions with an interior volume at least greater than 50 milliliters, and contracted state dimensions of less than 2 centimeters diameter and less than 5 centimeters in length, and configured so that in said contracted state, said balloon can pass from a stomach of a human patient completely through a gastrointestinal tract of said human patient;
   wherein the hollow tube comprises an interior balloon side end and an exterior balloon side end;
   said interior balloon side end, oriented towards said interior volume, being a closed end;
   wherein:
   a) said at least one tube opening comprises one or more openings in sides of a circumference of said hollow tube;
   b) said elastic polymeric sheath extends a few millimeters into the interior of the balloon, said elastic polymeric sheath having an inner sheath surface oriented towards said hollow tube, and an outer sheath surface oriented towards said interior volume;
   c) said expansion valve portion is formed between an outer surface of said hollow tube, and said inner sheath surface of said elastic polymeric sheath, said expansion valve portion configured to open and close based on a differential pressure between a hollow portion of said hollow tube, and said interior volume;
   wherein said expansion valve portion is configured to:
   i) in the first open mode, when outside pressurized gas or fluid are injected into said hollow tube, said expansion valve portion opens due to separation of said inner sheath surface of said elastic polymeric sheath from said outer surface of said hollow tube, thus permitting injected gas or fluid to flow through said one or more openings and enter said interior volume;
   ii) in the second closed mode, when a pressure of pressurized gas and fluid in said interior volume is greater than a pressure of gas or fluid in said hollow tube, said expansion valve portion closes due to said elastic polymeric sheath covering said one or more openings, thus preventing any of internal pressurized gas or fluid from using said one or more openings to exit said balloon;
   wherein said closed end comprises an exterior closed end facing towards said interior volume, and an interior closed end facing towards an interior of said hollow tube;
   wherein said interior closed end of said hollow tube is formed by a degradable retainer plug of said degradable element, and said timing valve portion is configured to:
   d) while said degradable retainer plug is intact, prevent any of internal pressurized gas and fluid from using said hollow tube to exit said balloon;
   e) after said degradable retainer plug has degraded, allow any of internal pressurized gas and fluid to use said hollow tube to exit said balloon.

2. The device of claim 1, wherein the interior of said balloon further comprises an enzymatic material configured to degrade said degradable element into a biocompatible degraded material over a time range between hours to years when said balloon is stored at approximately 37 degrees centigrade.

3. The device of claim 1, wherein the degradable retainer plug is substantially cylindrical with length and diameter dimensions;
and wherein a time that said degradable retainer plug remains intact is at least partially determined by said dimensions of said degradable retainer plug;
and the length of said degradable retainer plug is chosen to be directly proportional to the time required for said degradable retainer plug to degrade.

4. The device of the claim 1, wherein a surface of said degradable retainer plug that is oriented towards the balloon's exterior further comprises a plug covering configured to:
a) while said degradable retainer plug is intact, prevent any gastrointestinal contents or fluid from contacting said degradable retainer plug
b) after said degradable retainer plug has degraded, allow any of internal pressurized gas and fluid to use said combination flow regulator expansion valve and timing valve to exit said balloon.

5. The device of claim 1, wherein said balloon is temporarily attached to an intermedium catheter by a detachable link comprising said expansion pin;
said intermedium catheter comprising a proximal end, a medial portion, and a distal end;
said detachable link connecting to said distal end of said intermedium catheter and said expansion valve portion;
said intermedium catheter configured, when attached to said expansion valve portion, to deliver any of outside pressurized gas and fluid to said balloon;
said intermedium catheter further configured to apply mechanical force to said expansion valve portion to detach said intermedium catheter from said balloon.

6. The device of claim 5, wherein said expansion valve portion further comprises an outside opening configured to accommodate the hollow expansion pin, the hollow expansion pin further comprising at least one side hole, said pin configured to fit inside said outside opening and to use displacement of said elastic polymeric sheath to place said expansion valve portion in said first open mode, thus permitting passage of any of fluid or gas into said balloon;
said distal end of said intermedium catheter is attached to said hollow expansion pin;
said intermedium catheter and said expansion valve portion further configured so that when said intermedium catheter is attached to said expansion valve portion, any of outside pressurized gas and fluid is delivered to said balloon through said hollow expansion pin; and
said expansion pin and said expansion valve portion further configured so that when said expansion pin is at least partially withdrawn from said outside opening, said expansion valve portion operates in said second closed mode, thus preventing passage of any of fluid or gas out of said balloon.

7. The device of claim 5, wherein any of said balloon, said intermedium catheter, said regulator or said distal end further comprises any of sensors or transmitters configured to help provide information pertaining to a present location of said distal end relative to a gastrointestinal system of a patient when said distal end of said intermedium catheter is inside a patient.

8. The device of claim 5, wherein at least a portion of a proximal end of said expansion valve portion is exterior to said balloon, and is detachably connected to said distal end of said intermedium catheter; and
at least a portion of a distal end of said timing valve portion is located on an interior of said balloon.

9. The device of claim 1, wherein at least portions of said skin further comprise biodegradable material configured to dissolve, causing said balloon to burst, over a time range between at least one hour and less than a year after said balloon contacts gastrointestinal digestive fluids; and/or
said degradable element further comprises biodegradable material configured to dissolve, causing said balloon to burst, over a time range between at least one hour and less than a year after said balloon contacts gastrointestinal digestive fluids.

10. The device of claim 1, wherein said balloon, in said contracted state, is further disposed within a capsule comprising a top capsule unit and a bottom capsule unit, at least said top capsule unit being nondegradable, and said bottom capsule unit configured to enclose said contracted state of said balloon;
said capsule configured to traverse an esophagus of a patient from a mouth of said patient to a stomach of said patient, and then to release said balloon into said stomach upon application of either mechanical force or chemical action of stomach digestive fluids.

11. The device of claim 1, wherein said expansion valve portion and said timing valve portion occupy different parts of a same said hollow tube.

12. A gastrointestinal device comprising:
a balloon comprising a thin flexible polymeric skin enclosing an interior volume, said balloon capable of transitioning between a contracted state and an expanded state;
a regulator comprising a combination flow regulator expansion valve and timing valve embedded in said skin and spanning from an interior to an exterior of said balloon, forming an adjustable one-way valve, said combination flow regulator expansion valve and timing valve comprising a flow regulator expansion valve portion comprising a hollow tube with at least one tube opening that opens into the interior of said balloon, an elastic polymeric sheath sealing said at least one tube opening, said hollow tube configured to accommodate a hollow expansion pin with a rounded bottom, said hollow expansion pin configured to transport any of outside pressurized gas and fluid, said elastic polymeric sheath configured to be displaced from said at least one tube opening by any of said outside pressurized gas and fluid, said flow regulator expansion valve portion configured to:
a) in a first open mode, permit any of outside pressurized gas and fluid to enter said balloon and cause said balloon to transition from said contracted state to said expanded state;
b) in a second closed mode, prevent any of internal pressurized gas and fluid from using said expansion valve portion to exit said balloon;
said combination flow regulator expansion valve and timing valve further comprising a timing valve portion comprising a gas and fluid impermeable timing regulator degradable element, said timing valve portion configured to:
c) while said degradable element is intact, said degradable element prevents any of internal pressurized gas and fluid from using said combination flow regulator expansion valve and timing valve to exit said balloon;

d) after said degradable element has degraded, allow any of internal pressurized gas and fluid to use said combination flow regulator expansion valve and timing valve to exit said balloon;

said balloon having expanded state dimensions with an interior volume at least greater than 50 milliliters, and contracted state dimensions of less than 2 centimeters diameter and less than 5 centimeters in length, and configured so that in said contracted state, said balloon can pass from a stomach of a human patient completely through a gastrointestinal tract of said human patient;

wherein said balloon, in said contracted state, is further disposed within a capsule comprising a top capsule unit and a bottom capsule unit, at least said top capsule unit being nondegradable, and said bottom capsule unit configured to enclose said contracted state of said balloon;

said capsule configured to traverse an esophagus of a patient from a mouth of said patient to a stomach of said patient, and then to release said balloon into said stomach upon application of either mechanical force or chemical action of stomach digestive fluids;

wherein said balloon and said bottom capsule unit of said capsule are temporarily attached to an intermedium catheter by a detachable link comprising said expansion pin;

said intermedium catheter comprising a proximal end, a medial portion, and a distal end;

said detachable link connecting said distal end of said intermedium catheter with a proximal end of said expansion valve portion;

said intermedium catheter configured, when attached to said expansion valve portion, to deliver any of pressurized gas and fluid to said balloon;

said intermedium catheter further configured to apply mechanical force to said expansion valve portion to detach said intermedium catheter from at least said balloon.

13. The device of claim 12, wherein said intermedium catheter further comprises a freely movable outer sheath configured to apply said mechanical force to at least one of said balloon at said expansion valve portion, and said top capsule unit by applying a counter force towards said balloon while pulling said intermedium catheter away from a patient's body.

14. The device of claim 12, wherein said capsule further comprises any of sensors or transmitters configured to provide information pertaining to a present location of said distal end relative to a gastrointestinal system of a patient when said distal end of said intermedium catheter is inside a patient.

15. The device of claim 14, wherein said sensors comprise any of optical fiber imagers, video sensors, pH sensors, chemical sensors, pressure sensors, temperature sensors, infrared sensors, magnetic sensors, proximity sensors, force sensors, or radiofrequency sensors connected to outside readout devices by a wired link over said catheter.

16. The device of claim 12, wherein any of said top capsule unit comprises a nondegradable material, and said bottom capsule unit comprises biodegradable materials configured to dissolve in contact with gastrointestinal digestive fluids.

17. The device of claim 12, wherein said top capsule unit comprises soft, non-traumatic nondegradable material configured to be permanently attached to a distal end of said intermedium catheter; or said top capsule unit is configured to protect a gastroesophageal junction of a patient from trauma while mechanical force is applied to said intermedium catheter and said balloon.

18. The device of claim 12, wherein said balloon is further configured for sustained delivery of therapeutic material.

19. The device of claim 12, wherein the hollow tube comprises an interior balloon side end and an exterior balloon side end;

said interior balloon side end, oriented towards said interior volume, being a closed end;

wherein:

a) said at least one tube opening comprises one or more openings in sides of a circumference of said hollow tube;

b) said elastic polymeric sheath extends a few millimeters into the interior of the balloon, said elastic polymeric sheath having an inner sheath surface oriented towards said hollow tube, and an outer sheath surface oriented towards said interior volume;

c) said expansion valve portion is formed between an outer surface of said hollow tube, and said inner sheath surface of said elastic polymeric sheath, said expansion valve portion configured to open and close based on a differential pressure between a hollow portion of said hollow tube, and said interior volume;

wherein said expansion valve portion is configured to:

i) in the first open mode, when outside pressurized gas or fluid are injected into said hollow tube, said expansion valve portion opens due to separation of said inner sheath surface of said elastic polymeric sheath from said outer surface of said hollow tube, thus permitting injected gas or fluid to flow through said one or more openings and enter said interior volume;

ii) in the second closed mode, when a pressure of pressurized gas and fluid in said interior volume is greater than a pressure of gas or fluid in said hollow tube, said expansion valve portion closes due to said elastic polymeric sheath covering said one or more openings, thus preventing any of internal pressurized gas or fluid from using said one or more openings to exit said balloon;

wherein said closed end comprises an exterior closed end facing towards said interior volume, and an interior closed end facing towards an interior of said hollow tube;

wherein said interior closed end of said hollow tube is formed by a degradable retainer plug of said degradable element, and said timing valve portion is configured to:

d) while said degradable retainer plug is intact, prevent any of internal pressurized gas and fluid from using said hollow tube to exit said balloon;

e) after said degradable retainer plug has degraded, allow any of internal pressurized gas and fluid to use said hollow tube to exit said balloon.

20. A gastrointestinal device comprising:

at least one balloon comprising a thin flexible polymeric skin enclosing an interior volume, said at least one balloon capable of transitioning between a contracted state and an expanded state;

a regulator comprising a combination flow regulator expansion valve and timing valve embedded in said skin and spanning from an interior to an exterior of said at least one balloon, forming an adjustable one-way valve, said combination flow regulator expansion valve and timing valve comprising a flow regulator expansion valve portion comprising a hollow tube with at least one tube opening that opens into the interior of said balloon, an elastic polymeric sheath sealing said at least one tube opening, said hollow tube configured to accommodate a hollow expansion pin with a rounded bottom, said hollow expansion pin configured to transport any of outside pressurized gas and fluid, said elastic polymeric sheath configured to be displaced from said at least one tube opening by any of said outside pressurized gas and fluid, said flow regulator expansion valve portion configured to:
a) in a first open mode, permit any of outside pressurized gas and fluid to enter said at least one balloon and cause said at least one balloon to transition from said contracted state to said expanded state;
b) in a second closed mode, prevent any of internal pressurized gas and fluid from using said expansion valve portion to exit said at least one balloon;
said combination flow regulator expansion valve and timing valve further comprising a timing valve portion comprising a gas and fluid impermeable timing regulator degradable element, said timing valve portion configured to:
c) while said degradable element is intact, said degradable element prevents any of internal pressurized gas and fluid from using said combination flow regulator expansion valve and timing valve to exit said at least one balloon;
d) after said degradable element has degraded, allow any of internal pressurized gas and fluid to use said combination flow regulator expansion valve and timing valve to exit said at least one balloon;
wherein for each said at least one balloon, the hollow tube comprises an interior balloon side end and an exterior balloon side end;
said interior balloon side end, oriented towards said interior volume, being a closed end;
wherein:
a) said at least one tube opening comprises one or more openings in sides of a circumference of said hollow tube;
b) said elastic polymeric sheath extends a few millimeters into the interior of the said at least one balloon, said elastic polymeric sheath having an inner sheath surface oriented towards said hollow tube, and an outer sheath surface oriented towards said interior volume;
c) said expansion valve portion is formed between an outer surface of said hollow tube, and said inner sheath surface of said elastic polymeric sheath, said expansion valve portion configured to open and close based on a differential pressure between a hollow portion of said hollow tube, and said interior volume;
wherein said expansion valve portion is configured to:
i) in the first open mode, when outside pressurized gas or fluid are injected into said hollow tube, said expansion valve portion opens due to separation of said inner sheath surface of said elastic polymeric sheath from said outer surface of said hollow tube, thus permitting injected gas or fluid to flow through said one or more openings and enter said interior volume;
ii) in the second closed mode, when a pressure of pressurized gas and fluid in said interior volume is greater than a pressure of gas or fluid in said hollow tube, said expansion valve portion closes due to said elastic polymeric sheath covering said one or more openings, thus preventing any of internal pressurized gas or fluid from using said one or more openings to exit said at least one balloon;
wherein said closed end comprises an exterior closed end facing towards said interior volume, and an interior closed end facing towards an interior of said hollow tube;
wherein said interior closed end of said hollow tube is formed by a degradable retainer plug of said degradable element, and said timing valve portion is configured to:
d) while said degradable retainer plug is intact, prevent any of internal pressurized gas and fluid from using said hollow tube to exit said at least one balloon;
e) after said degradable retainer plug has degraded, allow any of internal pressurized gas and fluid to use said hollow tube to exit said at least one balloon;
wherein said device comprises a plurality of regulator attached balloons attached to each other by said regulators, said plurality of regulator attached balloons having extended state dimensions so that a sum of the interior volume of said plurality of regulator attached balloons is at least greater than 50 ml, and contracted state dimensions so that a sum of said plurality of regulator attached balloons attached to each other by said regulators are less than 2 centimeters diameter and less than 5 centimeters in length, said plurality of regulator attached balloons configured so that in said contracted state, said plurality of regulator attached balloons can pass from a stomach of a human patient completely through a gastrointestinal tract of said human patient.

* * * * *